(12) United States Patent
Brenzel et al.

(10) Patent No.: US 8,287,538 B2
(45) Date of Patent: Oct. 16, 2012

(54) APPARATUS AND METHODS FOR FRACTURE REPAIR

(75) Inventors: Michael P. Brenzel, St. Paul, MN (US); Paul Hindrichs, Plymouth, MN (US)

(73) Assignee: Conventus Orthopaedics, Inc., Maple Grove, MN (US)

( * ) Notice: Subject to any disclaimer, the term of this patent is extended or adjusted under 35 U.S.C. 154(b) by 613 days.

(21) Appl. No.: 12/353,855

(22) Filed: Jan. 14, 2009

(65) Prior Publication Data

US 2009/0182336 A1    Jul. 16, 2009

Related U.S. Application Data

(60) Provisional application No. 61/020,778, filed on Jan. 14, 2008, provisional application No. 61/090,999, filed on Aug. 22, 2008.

(51) Int. Cl.
*A61B 17/56* (2006.01)
*A61B 17/58* (2006.01)
*A61F 2/30* (2006.01)

(52) U.S. Cl. ............................. 606/62; 606/63; 606/64

(58) Field of Classification Search ............. 606/62–64, 606/300–321
See application file for complete search history.

(56) References Cited

U.S. PATENT DOCUMENTS

| | | | |
|---|---|---|---|
| 1,493,240 A | 5/1924 | Bohn | |
| 2,485,531 A | 1/1948 | Dzus et al. | |
| 2,493,598 A | 1/1950 | Rozek | |
| 2,537,070 A | 1/1951 | Longfellow | |
| 2,580,821 A | 1/1952 | Nicola | |
| 2,780,223 A | 2/1957 | Haggland | |
| 3,143,915 A | 8/1964 | Tendler | |
| 3,143,916 A | 8/1964 | Rice | |
| 3,623,164 A | 11/1971 | Bokros | |
| 3,702,611 A | 11/1972 | Fishbein | |
| 3,710,789 A | 1/1973 | Ersek | |
| 3,744,488 A | 7/1973 | Cox | |
| 3,759,257 A | 9/1973 | Fischer et al. | |

(Continued)

FOREIGN PATENT DOCUMENTS

CA    2007210 A1    11/1990

(Continued)

OTHER PUBLICATIONS

App No. PCT/US 09/30971 International Search Report, Mar. 2009.

(Continued)

*Primary Examiner* — Eduardo C Robert
*Assistant Examiner* — Christina Negrelli
(74) *Attorney, Agent, or Firm* — Weiss & Arons LLP

(57) ABSTRACT

Apparatus and methods for bone fracture repair. The apparatus may include a structural support for positioning a first bone segment relative to a second bone segment. The apparatus may include an anchoring substrate. The anchoring substrate may be configured to compress the first bone segment to the second bone segment. The anchoring substrate may transmit tension from a distal bone segment anchor in the first bone segment to a proximal bone segment anchor in the second bone segment. The apparatus may be configured to be deployed percutaneously in an inner cavity of a bone. The apparatus may be installed in an open fracture. The apparatus may be expanded, self-expanding or configured for mechanically actuation. Some embodiments of the apparatus may include a central axis member that may be used in conjunction with expansion of one or both of the structural support and the anchoring substrate to configure the apparatus.

6 Claims, 54 Drawing Sheets

U.S. PATENT DOCUMENTS

| | | |
|---|---|---|
| 3,760,802 A | 9/1973 | Fischer et al. |
| 3,779,239 A | 12/1973 | Fischer et al. |
| 3,805,775 A | 4/1974 | Fischer et al. |
| 3,917,249 A | 11/1975 | Constantine |
| 3,970,075 A | 7/1976 | Sindelar et al. |
| 3,986,504 A | 10/1976 | Avila |
| 4,036,107 A | 7/1977 | Constantine |
| 4,091,806 A | 5/1978 | Aginsky |
| 4,124,026 A | 11/1978 | Berner et al. |
| 4,180,871 A | 1/1980 | Hamas |
| 4,204,531 A | 5/1980 | Aginsky |
| 4,227,518 A | 10/1980 | Aginsky |
| 4,229,840 A | 10/1980 | Gristina |
| 4,262,665 A | 4/1981 | Roalstad et al. |
| 4,274,398 A | 6/1981 | Scott et al. |
| 4,275,717 A | 6/1981 | Bolesky |
| 4,293,962 A | 10/1981 | Fuson |
| 4,313,434 A | 2/1982 | Segal |
| 4,430,991 A | 2/1984 | Darnell |
| 4,453,539 A | 6/1984 | Raftopoulos et al. |
| 4,473,070 A | 9/1984 | Matthews et al. |
| 4,485,816 A | 12/1984 | Krumme |
| 4,519,100 A | 5/1985 | Wills et al. |
| 4,522,200 A | 6/1985 | Stednitz |
| 4,548,199 A | 10/1985 | Agee |
| 4,590,930 A | 5/1986 | Kurth et al. |
| 4,627,434 A | 12/1986 | Murray |
| 4,643,177 A | 2/1987 | Sheppard et al. |
| 4,655,203 A | 4/1987 | Tormala et al. |
| 4,660,557 A | 4/1987 | Collis |
| 4,665,906 A | 5/1987 | Jervis |
| 4,669,237 A | 6/1987 | Constantine |
| 4,674,488 A | 6/1987 | Nashef et al. |
| 4,705,027 A | 11/1987 | Klaue |
| 4,730,608 A | 3/1988 | Schlein |
| 4,751,922 A | 6/1988 | DiPietropolo |
| 4,777,942 A | 10/1988 | Frey et al. |
| 4,782,833 A | 11/1988 | Einhorn et al. |
| 4,820,305 A | 4/1989 | Harms et al. |
| 4,875,474 A | 10/1989 | Border |
| 4,886,062 A | 12/1989 | Wiktor |
| 4,914,818 A | 4/1990 | Hall et al. |
| 4,941,466 A | 7/1990 | Romano |
| 4,946,459 A | 8/1990 | Bradshaw et al. |
| 4,969,888 A | 11/1990 | Scholten et al. |
| 4,973,257 A | 11/1990 | Lhotak |
| 5,002,546 A | 3/1991 | Romano |
| 5,035,714 A | 7/1991 | Willert et al. |
| 5,053,036 A | 10/1991 | Perren et al. |
| 5,059,193 A | 10/1991 | Kuslich |
| 5,066,296 A | 11/1991 | Chapman et al. |
| 5,067,957 A | 11/1991 | Jervis |
| 5,071,407 A | 12/1991 | Termin et al. |
| 5,084,050 A | 1/1992 | Draenert |
| 5,102,413 A | 4/1992 | Poddar |
| 5,108,435 A | 4/1992 | Gustavson et al. |
| 5,112,333 A | 5/1992 | Fixel |
| 5,116,335 A | 5/1992 | Hannon et al. |
| 5,122,134 A | 6/1992 | Borzone et al. |
| 5,139,497 A | 8/1992 | Tilghman et al. |
| 5,151,103 A | 9/1992 | Tepic et al. |
| 5,169,402 A | 12/1992 | Elloy |
| 5,171,284 A | 12/1992 | Branemark |
| 5,180,382 A | 1/1993 | Frigg et al. |
| 5,190,545 A | 3/1993 | Corsi et al. |
| 5,190,546 A | 3/1993 | Jervis |
| 5,190,548 A | 3/1993 | Davis |
| 5,197,966 A | 3/1993 | Sommerkamp |
| 5,197,967 A | 3/1993 | Wilson |
| 5,197,971 A | 3/1993 | Bonutti |
| 5,203,773 A | 4/1993 | Green |
| 5,221,261 A | 6/1993 | Termin et al. |
| 5,236,431 A | 8/1993 | Gogolewski et al. |
| 5,250,048 A | 10/1993 | Gundolf |
| 5,263,955 A | 11/1993 | Baumgart et al. |
| 5,275,602 A | 1/1994 | Shimizu et al. |
| 5,281,225 A | 1/1994 | Vicenzi |
| 5,281,226 A | 1/1994 | Daydov et al. |
| 5,286,249 A | 2/1994 | Thibodaux |
| 5,307,790 A | 5/1994 | Byrne |
| 5,326,205 A | 7/1994 | Anspach et al. |
| 5,334,184 A | 8/1994 | Bimman |
| 5,358,405 A | 10/1994 | Imai |
| 5,376,097 A | 12/1994 | Phillips |
| 5,378,239 A | 1/1995 | Termin et al. |
| 5,380,328 A | 1/1995 | Morgan |
| 5,415,660 A | 5/1995 | Campbell et al. |
| 5,423,823 A | 6/1995 | Schmieding |
| 5,437,674 A | 8/1995 | Worcel et al. |
| 5,445,639 A | 8/1995 | Kuslich et al. |
| 5,454,365 A | 10/1995 | Bonutti |
| 5,458,599 A | 10/1995 | Adobbati |
| D365,634 S | 12/1995 | Morgan |
| 5,474,557 A | 12/1995 | Mai |
| 5,496,277 A | 3/1996 | Termin et al. |
| 5,501,695 A | 3/1996 | Anspach et al. |
| 5,505,734 A | 4/1996 | Caniggia et al. |
| 5,527,316 A | 6/1996 | Stone et al. |
| 5,531,792 A | 7/1996 | Huene |
| 5,545,162 A | 8/1996 | Huebner |
| 5,582,577 A | 12/1996 | Lund et al. |
| 5,586,983 A | 12/1996 | Sanders et al. |
| 5,586,985 A | 12/1996 | Putnam et al. |
| 5,591,169 A | 1/1997 | Benoist |
| 5,597,378 A | 1/1997 | Jervis |
| 5,602,935 A | 2/1997 | Yoshida et al. |
| 5,620,414 A | 4/1997 | Campbell |
| 5,620,445 A | 4/1997 | Brosnahan et al. |
| 5,624,440 A | 4/1997 | Huebner |
| 5,624,447 A | 4/1997 | Myers |
| 5,626,580 A | 5/1997 | Brosnahan |
| 5,645,589 A | 7/1997 | Li |
| 5,658,283 A | 8/1997 | Huebner |
| 5,660,188 A | 8/1997 | Groiso |
| 5,662,649 A | 9/1997 | Huebner |
| 5,676,545 A | 10/1997 | Jones |
| 5,676,699 A | 10/1997 | Gogolewski et al. |
| 5,681,310 A | 10/1997 | Yuan et al. |
| 5,683,389 A | 11/1997 | Orsak |
| 5,685,826 A | 11/1997 | Bonutti |
| 5,697,981 A | 12/1997 | Ison et al. |
| 5,718,704 A | 2/1998 | Medoff |
| 5,725,541 A | 3/1998 | Anspach, III et al. |
| 5,728,047 A | 3/1998 | Edoga |
| 5,728,098 A | 3/1998 | Sherman et al. |
| 5,741,266 A | 4/1998 | Moran et al. |
| 5,741,282 A | 4/1998 | Anspach et al. |
| 5,758,713 A | 6/1998 | Fallet |
| 5,779,703 A | 7/1998 | Benoist |
| 5,792,106 A | 8/1998 | Mische |
| 5,810,721 A | 9/1998 | Mueller et al. |
| 5,817,098 A | 10/1998 | Albrektsson et al. |
| 5,827,289 A | 10/1998 | Reiley et al. |
| D403,069 S | 12/1998 | Drewry et al. |
| 5,879,352 A | 3/1999 | Filoso et al. |
| 5,879,355 A | 3/1999 | Ullmark |
| 5,885,282 A | 3/1999 | Szabo |
| 5,888,196 A | 3/1999 | Bonutti |
| 5,893,850 A | 4/1999 | Cachia |
| 5,897,556 A | 4/1999 | Drewry et al. |
| 5,908,423 A | 6/1999 | Kashuba et al. |
| 5,915,036 A | 6/1999 | Grunkin et al. |
| 5,919,195 A | 7/1999 | Wilson et al. |
| 5,935,127 A | 8/1999 | Border |
| 5,938,699 A | 8/1999 | Campbell |
| 5,951,467 A | 9/1999 | Picha et al. |
| 5,951,556 A | 9/1999 | Faccioli et al. |
| 5,964,698 A | 10/1999 | Fowle |
| 5,976,134 A | 11/1999 | Huebner |
| 5,980,525 A | 11/1999 | Bryant et al. |
| 5,997,538 A | 12/1999 | Asnis et al. |
| 6,001,099 A | 12/1999 | Huebner |
| 6,019,762 A | 2/2000 | Cole |
| 6,019,947 A | 2/2000 | Kucherov |
| 6,033,412 A | 3/2000 | Losken et al. |
| 6,045,564 A | 4/2000 | Walen |
| 6,048,309 A | 4/2000 | Flom et al. |

| Patent | Date | Inventor |
|---|---|---|
| 6,053,922 A | 4/2000 | Krause et al. |
| 6,056,750 A | 5/2000 | Lob |
| 6,068,648 A | 5/2000 | Cole et al. |
| 6,074,392 A | 6/2000 | Durham |
| 6,096,040 A | 8/2000 | Esser |
| 6,113,603 A | 9/2000 | Medoff |
| 6,120,472 A | 9/2000 | Singer |
| 6,120,504 A | 9/2000 | Brumback et al. |
| 6,123,704 A | 9/2000 | Hajianpour |
| 6,126,662 A | 10/2000 | Carmichael et al. |
| 6,127,597 A | 10/2000 | Beyar et al. |
| 6,129,762 A | 10/2000 | Li |
| 6,142,935 A | 11/2000 | Flom et al. |
| 6,143,012 A | 11/2000 | Gausepohl |
| 6,149,651 A | 11/2000 | Drewry et al. |
| 6,149,689 A | 11/2000 | Grundei |
| 6,156,069 A | 12/2000 | Amstutz |
| 6,162,223 A | 12/2000 | Orsak et al. |
| 6,162,224 A | 12/2000 | Huebner |
| 6,171,309 B1 | 1/2001 | Huebner |
| 6,174,312 B1 | 1/2001 | Laminger |
| 6,197,027 B1 | 3/2001 | Hajianpour |
| 6,200,330 B1 | 3/2001 | Benderev et al. |
| 6,221,074 B1 | 4/2001 | Cole et al. |
| 6,221,102 B1 | 4/2001 | Baker et al. |
| 6,224,600 B1 | 5/2001 | Protogirou |
| 6,231,576 B1 | 5/2001 | Frigg et al. |
| 6,238,417 B1 | 5/2001 | Cole |
| 6,241,734 B1 | 6/2001 | Scribner et al. |
| 6,248,110 B1 | 6/2001 | Reiley et al. |
| 6,261,289 B1 | 7/2001 | Levy |
| 6,280,474 B1 | 8/2001 | Cassidy et al. |
| 6,299,642 B1 | 10/2001 | Chan |
| 6,302,915 B1 | 10/2001 | Cooney et al. |
| 6,306,141 B1 | 10/2001 | Jervis |
| 6,312,467 B1 | 11/2001 | Mcgee |
| 6,319,255 B1 | 11/2001 | Grundei et al. |
| 6,322,591 B1 | 11/2001 | Ahrens |
| 6,332,885 B1 | 12/2001 | Martella |
| 6,332,886 B1 | 12/2001 | Green et al. |
| 6,348,053 B1 | 2/2002 | Cachia |
| 6,364,909 B1 | 4/2002 | Mcgee |
| 6,365,555 B1 | 4/2002 | Moser et al. |
| 6,375,666 B1 | 4/2002 | Mische |
| 6,383,188 B2 | 5/2002 | Kuslich et al. |
| 6,402,753 B1 | 6/2002 | Cole et al. |
| 6,411,729 B1 | 6/2002 | Grunkin |
| 6,416,517 B2 | 7/2002 | Harder et al. |
| 6,423,070 B1 | 7/2002 | Zeppelin |
| 6,447,514 B1 | 9/2002 | Stalcup et al. |
| 6,447,515 B1 | 9/2002 | Meldrum |
| 6,447,518 B1 | 9/2002 | Krause et al. |
| 6,454,810 B1 | 9/2002 | Lob |
| 6,468,207 B1 | 10/2002 | Fowler |
| 6,491,694 B1 | 12/2002 | Orsak |
| 6,511,481 B2 | 1/2003 | von Hoffmann et al. |
| 6,517,541 B2 | 2/2003 | Sesic |
| 6,527,775 B1 | 3/2003 | Warburton |
| 6,540,770 B1 | 4/2003 | Tornier et al. |
| 6,544,267 B1 | 4/2003 | Cole et al. |
| 6,554,833 B2 | 4/2003 | Levy et al. |
| 6,575,973 B1 | 6/2003 | Shekalim |
| 6,582,467 B1 | 6/2003 | Teitelbaum et al. |
| 6,585,736 B2 | 7/2003 | Hajianpour |
| 6,585,770 B1 | 7/2003 | White et al. |
| 6,613,052 B1 | 9/2003 | Kinnett |
| 6,613,054 B2 | 9/2003 | Scribner et al. |
| 6,632,224 B2 | 10/2003 | Cachia et al. |
| 6,641,616 B1 | 11/2003 | Grundei |
| 6,648,890 B2 | 11/2003 | Culbert et al. |
| 6,652,585 B2 | 11/2003 | Lange |
| 6,656,187 B1 | 12/2003 | Camino |
| 6,656,219 B1 | 12/2003 | Wiktor |
| 6,660,009 B1 | 12/2003 | Azar |
| 6,660,041 B1 | 12/2003 | Grundei |
| 6,676,665 B2 | 1/2004 | Foley et al. |
| 6,679,886 B2 | 1/2004 | Weikel et al. |
| 6,685,706 B2 | 2/2004 | Padget et al. |
| 6,689,138 B2 | 2/2004 | Léchot et al. |
| 6,692,496 B1 | 2/2004 | Wardlaw |
| 6,701,174 B1 | 3/2004 | Krause et al. |
| 6,709,433 B1 | 3/2004 | Schoenefeld |
| 6,711,432 B1 | 3/2004 | Weiss et al. |
| 6,712,858 B1 | 3/2004 | Grundei et al. |
| 6,719,793 B2 | 4/2004 | McGee et al. |
| 6,746,451 B2 | 6/2004 | Middleton et al. |
| 6,749,611 B2 | 6/2004 | Venturini et al. |
| 6,755,831 B2 | 6/2004 | Putnam et al. |
| 6,761,722 B2 | 7/2004 | Cole et al. |
| 6,767,350 B1 | 7/2004 | Lob |
| 6,775,401 B2 | 8/2004 | Hwang et al. |
| 6,780,185 B2 | 8/2004 | Frei et al. |
| 6,783,530 B1 | 8/2004 | Levy et al. |
| 6,783,532 B2 | 8/2004 | Steiner et al. |
| 6,783,533 B2 | 8/2004 | Green et al. |
| 6,793,655 B2 | 9/2004 | Orsak |
| 6,793,659 B2 | 9/2004 | Putnam |
| 6,811,568 B2 | 11/2004 | Minamikawa |
| 6,827,723 B2 | 12/2004 | Carson |
| 6,827,743 B2 | 12/2004 | Eisermann et al. |
| 6,849,051 B2 | 2/2005 | Sramek et al. |
| 6,852,128 B2 | 2/2005 | Lange |
| 6,866,665 B2 | 3/2005 | Orbay |
| 6,887,243 B2 | 5/2005 | Culbert |
| 6,890,333 B2 | 5/2005 | von Hoffmann et al. |
| 6,893,444 B2 | 5/2005 | Orbay |
| 6,908,465 B2 | 6/2005 | von Hoffmann et al. |
| 6,911,046 B2 | 6/2005 | Schulter |
| 6,923,813 B2 | 8/2005 | Phillips et al. |
| 6,923,817 B2 | 8/2005 | Carson et al. |
| 6,923,828 B1 | 8/2005 | Wiktor |
| 6,926,720 B2 | 8/2005 | Castañeda |
| 6,932,086 B2 | 8/2005 | Hajianpour |
| 6,942,666 B2 | 9/2005 | Overaker et al. |
| 6,942,668 B2 | 9/2005 | Padget et al. |
| 6,949,101 B2 | 9/2005 | McCleary et al. |
| 6,951,561 B2 | 10/2005 | Warren et al. |
| 6,975,894 B2 | 12/2005 | Wehrli et al. |
| 6,984,248 B2 | 1/2006 | Hyde, Jr. |
| 6,986,771 B2 | 1/2006 | Paul et al. |
| 6,989,011 B2 | 1/2006 | Paul et al. |
| 6,991,656 B2 | 1/2006 | Mears |
| 7,008,425 B2 | 3/2006 | Phillips |
| 7,008,428 B2 | 3/2006 | Cachia et al. |
| 7,008,430 B2 | 3/2006 | Dong et al. |
| 7,011,662 B2 | 3/2006 | Lechot et al. |
| 7,018,332 B1 | 3/2006 | Masson et al. |
| 7,018,380 B2 | 3/2006 | Cole |
| 7,022,069 B1 | 4/2006 | Masson et al. |
| 7,041,104 B1 | 5/2006 | Cole et al. |
| 7,041,138 B2 | 5/2006 | Lange |
| 7,048,542 B2 | 5/2006 | Von Arx et al. |
| 7,052,498 B2 | 5/2006 | Levy et al. |
| 7,063,701 B2 | 6/2006 | Michelson |
| 7,070,601 B2 | 7/2006 | Culbert et al. |
| 7,090,676 B2 | 8/2006 | Huebner et al. |
| 7,097,646 B2 | 8/2006 | Schantz |
| 7,097,648 B1 | 8/2006 | Globerman et al. |
| 7,122,033 B2 | 10/2006 | Wood |
| 7,122,043 B2 | 10/2006 | Greenhalgh et al. |
| 7,122,052 B2 | 10/2006 | Greenhalgh |
| 7,131,995 B2 | 11/2006 | Biedermann et al. |
| 7,137,987 B2 | 11/2006 | Patterson et al. |
| 7,141,054 B2 | 11/2006 | Vandewalle |
| 7,141,067 B2 | 11/2006 | Jones et al. |
| 7,147,640 B2 | 12/2006 | Huebner et al. |
| 7,153,307 B2 | 12/2006 | Scribner et al. |
| 7,153,309 B2 | 12/2006 | Huebner et al. |
| 7,160,302 B2 | 1/2007 | Warburton |
| 7,160,331 B2 | 1/2007 | Cooney et al. |
| 7,172,595 B1 | 2/2007 | Goble |
| 7,175,625 B2 | 2/2007 | Culbert |
| 7,179,024 B2 | 2/2007 | Greenhalgh |
| 7,189,237 B2 | 3/2007 | Huebner |
| 7,189,240 B1 | 3/2007 | Dekel |
| 7,195,589 B2 | 3/2007 | Masson et al. |
| 7,214,227 B2 | 5/2007 | Colleran et al. |
| 7,220,282 B2 | 5/2007 | Kuslich et al. |

| | | | | | |
|---|---|---|---|---|---|
| 7,229,441 B2 | 6/2007 | Trieu et al. | 2002/0191823 A1 | 12/2002 | Wehrli et al. |
| 7,235,079 B2 | 6/2007 | Jensen et al. | 2003/0040805 A1 | 2/2003 | Minamikawa |
| 7,237,556 B2 | 7/2007 | Smothers et al. | 2003/0055425 A1 | 3/2003 | Hajianpour |
| 7,255,712 B1 | 8/2007 | Steinberg | 2003/0069582 A1 | 4/2003 | Culbert |
| 7,258,692 B2 | 8/2007 | Thelen et al. | 2003/0083660 A1 | 5/2003 | Orbay |
| 7,264,622 B2 | 9/2007 | Michelson | 2003/0083662 A1 | 5/2003 | Middleton |
| 7,267,678 B2 | 9/2007 | Medoff | 2003/0093076 A1 | 5/2003 | Venturini et al. |
| 7,282,053 B2 | 10/2007 | Orbay | 2003/0097132 A1 | 5/2003 | Padget et al. |
| 7,294,130 B2 | 11/2007 | Orbay | 2003/0097133 A1 | 5/2003 | Green et al. |
| 7,300,449 B2 | 11/2007 | Mische et al. | 2003/0105461 A1 | 6/2003 | Putnam |
| 7,306,603 B2 | 12/2007 | Boehm et al. | 2003/0109932 A1 | 6/2003 | Keynan |
| 7,306,683 B2 | 12/2007 | Cheung et al. | 2003/0120273 A1 | 6/2003 | Cole |
| 7,311,711 B2 | 12/2007 | Cole | 2003/0130660 A1 | 7/2003 | Levy et al. |
| D560,128 S | 1/2008 | Diederich et al. | 2003/0153918 A1 | 8/2003 | Putnam et al. |
| 7,326,249 B2 | 2/2008 | Lange | 2003/0216738 A1 | 11/2003 | Azar |
| 7,341,601 B2 | 3/2008 | Eisermann et al. | 2003/0220641 A1 | 11/2003 | Thelen et al. |
| 7,344,539 B2 | 3/2008 | Serhan et al. | 2003/0220644 A1 | 11/2003 | Thelen et al. |
| 7,354,453 B2 | 4/2008 | McAfee | 2003/0220646 A1 | 11/2003 | Thelen et al. |
| 7,476,226 B2 | 1/2009 | Weikel et al. | 2003/0220698 A1 | 11/2003 | Mears et al. |
| 7,481,815 B2 | 1/2009 | Fernandez | 2003/0225407 A1 | 12/2003 | Estrada |
| 7,485,119 B2 | 2/2009 | Thelen et al. | 2004/0039384 A1 | 2/2004 | Boehm et al. |
| 7,488,320 B2 | 2/2009 | Middleton | 2004/0044413 A1 | 3/2004 | Schulter |
| 7,488,329 B2 | 2/2009 | Thelen et al. | 2004/0049192 A1 | 3/2004 | Shimizu |
| D589,147 S | 3/2009 | Colleran et al. | 2004/0078082 A1 | 4/2004 | Lange |
| 7,500,977 B2 | 3/2009 | Assell et al. | 2004/0092946 A1 | 5/2004 | Bagga et al. |
| 7,507,241 B2 | 3/2009 | Levy et al. | 2004/0102777 A1 | 5/2004 | Huebner |
| 7,563,263 B2 | 7/2009 | Orbay et al. | 2004/0102778 A1 | 5/2004 | Huebner et al. |
| 7,569,061 B2 | 8/2009 | Colleran | 2004/0102788 A1 | 5/2004 | Huebner et al. |
| 7,588,575 B2 | 9/2009 | Colleran et al. | 2004/0106925 A1 | 6/2004 | Culbert |
| 7,588,577 B2 | 9/2009 | Fencl et al. | 2004/0138665 A1 | 7/2004 | Padget et al. |
| 7,588,588 B2 | 9/2009 | Spitler et al. | 2004/0143264 A1 | 7/2004 | McAfee |
| 7,601,152 B2 | 10/2009 | Levy et al. | 2004/0153114 A1 | 8/2004 | Reiley et al. |
| 7,611,515 B2 | 11/2009 | Wolford et al. | 2004/0153115 A1 | 8/2004 | Reiley et al. |
| 7,621,950 B1 | 11/2009 | Globerman et al. | 2004/0167528 A1 | 8/2004 | Schantz |
| 7,632,277 B2 | 12/2009 | Woll et al. | 2004/0167625 A1 | 8/2004 | Beyar et al. |
| 7,632,310 B2 | 12/2009 | Clifford et al. | 2004/0181221 A1 | 9/2004 | Huebner et al. |
| 7,670,339 B2 | 3/2010 | Levy et al. | 2004/0193163 A1 | 9/2004 | Orbay |
| 7,682,364 B2 | 3/2010 | Reiley et al. | 2004/0193164 A1 | 9/2004 | Orbay |
| 7,695,471 B2 | 4/2010 | Cheung et al. | 2004/0193165 A1 | 9/2004 | Orbay |
| 7,695,502 B2 | 4/2010 | Orbay et al. | 2004/0193251 A1 | 9/2004 | Rudnick et al. |
| 7,704,251 B2 | 4/2010 | Huebner et al. | 2004/0193267 A1 | 9/2004 | Jones et al. |
| 7,708,742 B2 | 5/2010 | Scribner et al. | 2004/0208717 A1 | 10/2004 | Greenhalgh |
| 7,713,271 B2 | 5/2010 | Warburton et al. | 2004/0214311 A1 | 10/2004 | Levy |
| 7,727,264 B2 | 6/2010 | Orbay et al. | 2004/0230193 A1 | 11/2004 | Cheung et al. |
| 7,758,500 B2 | 7/2010 | Boyd et al. | 2004/0236327 A1 | 11/2004 | Paul et al. |
| 7,806,929 B2 | 10/2010 | Brown | 2004/0236328 A1 | 11/2004 | Paul et al. |
| 7,828,802 B2 | 11/2010 | Levy et al. | 2004/0236339 A1 | 11/2004 | Pepper |
| 7,837,612 B2 | 11/2010 | Gill et al. | 2004/0249375 A1 | 12/2004 | Agee et al. |
| 7,846,162 B2 | 12/2010 | Nelson et al. | 2004/0267269 A1 | 12/2004 | Middleton et al. |
| 8,007,498 B2 | 8/2011 | Mische | 2005/0010231 A1 | 1/2005 | Myers |
| 8,043,334 B2 * | 10/2011 | Fisher et al. ................ 606/247 | 2005/0015129 A1 | 1/2005 | Mische |
| 8,157,804 B2 | 4/2012 | Betts | 2005/0015154 A1 | 1/2005 | Lindsey et al. |
| 2001/0018588 A1 | 8/2001 | Harder et al. | 2005/0033366 A1 | 2/2005 | Cole et al. |
| 2001/0053912 A1 | 12/2001 | Frigg | 2005/0043733 A1 | 2/2005 | Eisermann et al. |
| 2002/0013600 A1 | 1/2002 | Scribner et al. | 2005/0065522 A1 | 3/2005 | Orbay |
| 2002/0015517 A1 | 2/2002 | Hwang et al. | 2005/0065523 A1 | 3/2005 | Orbay |
| 2002/0029081 A1 | 3/2002 | Scarborough et al. | 2005/0065524 A1 | 3/2005 | Orbay |
| 2002/0032444 A1 | 3/2002 | Mische | 2005/0065526 A1 | 3/2005 | Drew et al. |
| 2002/0055742 A1 | 5/2002 | Lieberman | 2005/0070902 A1 | 3/2005 | Medoff |
| 2002/0065530 A1 | 5/2002 | Mische | 2005/0085813 A1 | 4/2005 | Spitler et al. |
| 2002/0111629 A1 | 8/2002 | Phillips | 2005/0085818 A1 | 4/2005 | Huebner |
| 2002/0120269 A1 | 8/2002 | Lange | 2005/0085824 A1 | 4/2005 | Castaneda |
| 2002/0120270 A1 | 8/2002 | Trieu et al. | 2005/0085921 A1 | 4/2005 | Gupta et al. |
| 2002/0123750 A1 | 9/2002 | Eisermann et al. | 2005/0113836 A1 | 5/2005 | Lozier et al. |
| 2002/0133153 A1 | 9/2002 | Hyde | 2005/0113892 A1 | 5/2005 | Sproul |
| 2002/0133156 A1 | 9/2002 | Cole | 2005/0119749 A1 | 6/2005 | Lange |
| 2002/0133172 A1 | 9/2002 | Lambrecht et al. | 2005/0124972 A1 | 6/2005 | Mische et al. |
| 2002/0133175 A1 | 9/2002 | Carson | 2005/0125066 A1 | 6/2005 | Mcafee |
| 2002/0138149 A1 | 9/2002 | Hyde | 2005/0131407 A1 | 6/2005 | Sicvol et al. |
| 2002/0143329 A1 | 10/2002 | Serhan et al. | 2005/0154331 A1 | 7/2005 | Christie et al. |
| 2002/0143333 A1 | 10/2002 | von Hoffmann et al. | 2005/0159749 A1 | 7/2005 | Levy et al. |
| 2002/0143334 A1 | 10/2002 | Hoffmann et al. | 2005/0177172 A1 | 8/2005 | Acker et al. |
| 2002/0143335 A1 | 10/2002 | von Hoffmann et al. | 2005/0182399 A1 | 8/2005 | Levine |
| 2002/0147451 A1 | 10/2002 | Mcgee | 2005/0197537 A1 | 9/2005 | Bonadio et al. |
| 2002/0147455 A1 | 10/2002 | Carson | 2005/0209557 A1 | 9/2005 | Carroll et al. |
| 2002/0165461 A1 | 11/2002 | Hayzelden et al. | 2005/0216000 A1 | 9/2005 | Colleran et al. |
| 2002/0165544 A1 | 11/2002 | Perren et al. | 2005/0216007 A1 | 9/2005 | Woll et al. |
| 2002/0171208 A1 | 11/2002 | Lechot et al. | 2005/0228391 A1 | 10/2005 | Levy et al. |
| 2002/0183758 A1 | 12/2002 | Middleton et al. | 2005/0240190 A1 | 10/2005 | Gall et al. |

| Publication No. | Date | Inventors |
|---|---|---|
| 2005/0240193 A1 | 10/2005 | Layne et al. |
| 2005/0245928 A1 | 11/2005 | Colleran et al. |
| 2005/0261779 A1 | 11/2005 | Meyer |
| 2005/0267483 A1 | 12/2005 | Middleton |
| 2005/0273138 A1 | 12/2005 | To et al. |
| 2005/0277936 A1 | 12/2005 | Siravo et al. |
| 2005/0277978 A1 | 12/2005 | Greenhalgh |
| 2005/0283154 A1 | 12/2005 | Orbay et al. |
| 2005/0288676 A1 | 12/2005 | Schnieders et al. |
| 2006/0004362 A1 | 1/2006 | Patterson et al. |
| 2006/0004462 A1 | 1/2006 | Gupta |
| 2006/0009771 A1 | 1/2006 | Orbay et al. |
| 2006/0015123 A1 | 1/2006 | Fencl et al. |
| 2006/0036240 A1 | 2/2006 | Colleran et al. |
| 2006/0036244 A1 | 2/2006 | Spitler et al. |
| 2006/0052788 A1 | 3/2006 | Thelen et al. |
| 2006/0058621 A1 | 3/2006 | Wehrli et al. |
| 2006/0058826 A1 | 3/2006 | Evans et al. |
| 2006/0064005 A1 | 3/2006 | Triano et al. |
| 2006/0064106 A1 | 3/2006 | Fernandez |
| 2006/0064164 A1 | 3/2006 | Thelen et al. |
| 2006/0069392 A1 | 3/2006 | Renzi Brivio et al. |
| 2006/0079894 A1 | 4/2006 | Colleran et al. |
| 2006/0079905 A1 | 4/2006 | Beyar et al. |
| 2006/0089648 A1 | 4/2006 | Masini |
| 2006/0100631 A1 | 5/2006 | Sullivan et al. |
| 2006/0100706 A1 | 5/2006 | Shadduck et al. |
| 2006/0106390 A1 | 5/2006 | Jensen et al. |
| 2006/0106394 A1 | 5/2006 | Colleran |
| 2006/0116773 A1 | 6/2006 | Cooney et al. |
| 2006/0122600 A1 | 6/2006 | Cole |
| 2006/0122610 A1 | 6/2006 | Culbert et al. |
| 2006/0142858 A1 | 6/2006 | Colleran et al. |
| 2006/0149281 A1 | 7/2006 | Reiley et al. |
| 2006/0155289 A1 | 7/2006 | Windhager et al. |
| 2006/0173454 A1 | 8/2006 | Spitler et al. |
| 2006/0187748 A1 | 8/2006 | Kozyuk |
| 2006/0189994 A1 | 8/2006 | Wolford et al. |
| 2006/0195103 A1 | 8/2006 | Padget et al. |
| 2006/0200061 A1 | 9/2006 | Warkentine |
| 2006/0200140 A1 | 9/2006 | Lange |
| 2006/0200143 A1 | 9/2006 | Warburton |
| 2006/0217730 A1 | 9/2006 | Termanini |
| 2006/0241629 A1 | 10/2006 | Krebs et al. |
| 2006/0241630 A1 | 10/2006 | Brunnett et al. |
| 2006/0241671 A1 | 10/2006 | Greenhalgh |
| 2006/0241776 A1 | 10/2006 | Brown et al. |
| 2006/0247637 A1 | 11/2006 | Colleran et al. |
| 2006/0264944 A1 | 11/2006 | Cole |
| 2006/0264945 A1 | 11/2006 | Edidin et al. |
| 2006/0264951 A1 | 11/2006 | Nelson et al. |
| 2006/0264952 A1 | 11/2006 | Nelson et al. |
| 2006/0271053 A1 | 11/2006 | Schlapfer et al. |
| 2006/0271061 A1 | 11/2006 | Beyar et al. |
| 2006/0271198 A1 | 11/2006 | Mcafee |
| 2006/0276797 A1 | 12/2006 | Botimer |
| 2007/0016188 A1 | 1/2007 | Boehm et al. |
| 2007/0016198 A1 | 1/2007 | Boehm et al. |
| 2007/0016199 A1 | 1/2007 | Boehm et al. |
| 2007/0016211 A1 | 1/2007 | Botimer |
| 2007/0016283 A1 | 1/2007 | Greenhalgh et al. |
| 2007/0016300 A1 | 1/2007 | Kuslich |
| 2007/0027230 A1 | 2/2007 | Beyar et al. |
| 2007/0032567 A1 | 2/2007 | Beyar et al. |
| 2007/0043373 A1 | 2/2007 | Sala et al. |
| 2007/0049936 A1 | 3/2007 | Colleran et al. |
| 2007/0055379 A1 | 3/2007 | Stone et al. |
| 2007/0073342 A1 | 3/2007 | Stone et al. |
| 2007/0100285 A1 | 5/2007 | Griffin et al. |
| 2007/0112427 A1 | 5/2007 | Christy et al. |
| 2007/0118132 A1 | 5/2007 | Culbert et al. |
| 2007/0123877 A1 | 5/2007 | Goldin et al. |
| 2007/0123886 A1 | 5/2007 | Meyer et al. |
| 2007/0123936 A1 | 5/2007 | Goldin et al. |
| 2007/0123995 A1 | 5/2007 | Thelen et al. |
| 2007/0129746 A1 | 6/2007 | Mische |
| 2007/0142919 A1 | 6/2007 | Cooney et al. |
| 2007/0173745 A1 | 7/2007 | Diederich et al. |
| 2007/0173835 A1 | 7/2007 | Medoff et al. |
| 2007/0173839 A1 | 7/2007 | Running et al. |
| 2007/0173939 A1 | 7/2007 | Kim et al. |
| 2007/0179505 A1 | 8/2007 | Culbert |
| 2007/0198043 A1 | 8/2007 | Cox et al. |
| 2007/0213727 A1 | 9/2007 | Bottlang et al. |
| 2007/0219634 A1 | 9/2007 | Greenhalgh et al. |
| 2007/0225568 A1 | 9/2007 | Colleran |
| 2007/0225721 A1 | 9/2007 | Thelen et al. |
| 2007/0225726 A1 | 9/2007 | Dye et al. |
| 2007/0225810 A1 | 9/2007 | Colleran et al. |
| 2007/0233091 A1 | 10/2007 | Naifeh et al. |
| 2007/0233105 A1 | 10/2007 | Nelson et al. |
| 2007/0244485 A1 | 10/2007 | Greenhalgh et al. |
| 2007/0255287 A1 | 11/2007 | Rabiner |
| 2007/0270855 A1 | 11/2007 | Partin et al. |
| 2007/0276392 A1 | 11/2007 | Beyar et al. |
| 2007/0276405 A1 | 11/2007 | Huebner et al. |
| 2007/0282443 A1 | 12/2007 | Globerman et al. |
| 2007/0283849 A1 | 12/2007 | Edidin et al. |
| 2007/0288097 A1 | 12/2007 | Hurowitz |
| 2008/0009874 A1 | 1/2008 | Meridew et al. |
| 2008/0015601 A1 | 1/2008 | Castro et al. |
| 2008/0019970 A1 | 1/2008 | Gorman |
| 2008/0039854 A1 | 2/2008 | Rabiner |
| 2008/0041629 A1 | 2/2008 | Aronstam et al. |
| 2008/0053575 A1 | 3/2008 | Cheung et al. |
| 2008/0058804 A1 | 3/2008 | Lechot et al. |
| 2008/0065072 A1 | 3/2008 | Spitler et al. |
| 2008/0065073 A1 | 3/2008 | Perriello et al. |
| 2008/0065074 A1 | 3/2008 | Yeung et al. |
| 2008/0071356 A1 | 3/2008 | Greenhalgh et al. |
| 2008/0077117 A1 | 3/2008 | Miller et al. |
| 2008/0077172 A1 | 3/2008 | Miller et al. |
| 2008/0077174 A1 | 3/2008 | Mische |
| 2008/0097332 A1 | 4/2008 | Greenhalgh et al. |
| 2008/0103501 A1 | 5/2008 | Ralph et al. |
| 2008/0108996 A1 | 5/2008 | Padget et al. |
| 2008/0114364 A1 | 5/2008 | Goldin et al. |
| 2008/0119886 A1 | 5/2008 | Greenhalgh et al. |
| 2008/0125784 A1 | 5/2008 | Rabiner et al. |
| 2008/0125805 A1 | 5/2008 | Mische |
| 2008/0132896 A1 | 6/2008 | Bowen et al. |
| 2008/0133017 A1 | 6/2008 | Beyar et al. |
| 2008/0140078 A1 | 6/2008 | Nelson et al. |
| 2008/0140130 A1 | 6/2008 | Chan et al. |
| 2008/0149115 A1 | 6/2008 | Hauck et al. |
| 2008/0161805 A1 | 7/2008 | Saravia et al. |
| 2008/0161825 A1 | 7/2008 | Greenhalgh et al. |
| 2008/0167657 A1 | 7/2008 | Greenhalgh |
| 2008/0177261 A1 | 7/2008 | Mcminn |
| 2008/0183171 A1 | 7/2008 | Elghazaly et al. |
| 2008/0194868 A1 | 8/2008 | Kozyuk |
| 2008/0195104 A1 | 8/2008 | Sidebotham et al. |
| 2008/0195105 A1 | 8/2008 | Sidebotham et al. |
| 2008/0200915 A1 | 8/2008 | Globerman et al. |
| 2008/0200951 A1 | 8/2008 | Mcafee |
| 2008/0208202 A1 | 8/2008 | Williams |
| 2008/0208261 A1 | 8/2008 | Medoff |
| 2008/0208320 A1 | 8/2008 | Tan-Malecki et al. |
| 2008/0212405 A1 | 9/2008 | Globerman et al. |
| 2008/0228192 A1 | 9/2008 | Beyar et al. |
| 2008/0249436 A1 | 10/2008 | Darr |
| 2008/0255560 A1 | 10/2008 | Myers et al. |
| 2008/0262495 A1 | 10/2008 | Coati et al. |
| 2008/0269742 A1 | 10/2008 | Levy et al. |
| 2008/0269745 A1 | 10/2008 | Justin |
| 2008/0269746 A1 | 10/2008 | Justin |
| 2008/0269747 A1 | 10/2008 | Justin |
| 2008/0269748 A1 | 10/2008 | Justin et al. |
| 2008/0269749 A1 | 10/2008 | Shalaby et al. |
| 2008/0269750 A1 | 10/2008 | Justin |
| 2008/0269776 A1 | 10/2008 | Justin et al. |
| 2008/0275448 A1 | 11/2008 | Sackett et al. |
| 2008/0275449 A1 | 11/2008 | Sackett et al. |
| 2008/0287950 A1 | 11/2008 | Frigg et al. |
| 2008/0287951 A1 | 11/2008 | Stoneburner et al. |
| 2008/0294163 A1 | 11/2008 | Chou et al. |
| 2008/0294166 A1 | 11/2008 | Goldin et al. |
| 2008/0294167 A1 | 11/2008 | Schumacher et al. |

| Publication | Date | Inventor |
|---|---|---|
| 2008/0294169 A1 | 11/2008 | Scott et al. |
| 2008/0294205 A1 | 11/2008 | Greenhalgh et al. |
| 2008/0319444 A9 | 12/2008 | Osorio et al. |
| 2009/0005782 A1* | 1/2009 | Chirico et al. .................. 606/63 |
| 2009/0012522 A1 | 1/2009 | Lob |
| 2009/0018542 A1 | 1/2009 | Saravia et al. |
| 2009/0018656 A1 | 1/2009 | Clifford et al. |
| 2009/0018666 A1 | 1/2009 | Grundei et al. |
| 2009/0024204 A1 | 1/2009 | Greenhalgh et al. |
| 2009/0048620 A1 | 2/2009 | Weiss et al. |
| 2009/0048629 A1 | 2/2009 | Rabiner |
| 2009/0054900 A1 | 2/2009 | Rabiner et al. |
| 2009/0076517 A1 | 3/2009 | Reiley et al. |
| 2009/0088752 A1 | 4/2009 | Metzinger et al. |
| 2009/0112196 A1 | 4/2009 | Rabiner et al. |
| 2009/0112330 A1 | 4/2009 | Grundei |
| 2009/0125028 A1 | 5/2009 | Teisen et al. |
| 2009/0131992 A1 | 5/2009 | Greenhalgh et al. |
| 2009/0143781 A1 | 6/2009 | Mische |
| 2009/0143827 A1 | 6/2009 | Levy et al. |
| 2009/0149890 A1 | 6/2009 | Martin |
| 2009/0149956 A1 | 6/2009 | Greenhalgh et al. |
| 2009/0157080 A1 | 6/2009 | Warburton |
| 2009/0163918 A1 | 6/2009 | Levy et al. |
| 2009/0177206 A1 | 7/2009 | Lozier et al. |
| 2009/0177239 A1 | 7/2009 | Castro |
| 2009/0216232 A1 | 8/2009 | Buford et al. |
| 2009/0228007 A1 | 9/2009 | Justin et al. |
| 2009/0228008 A1 | 9/2009 | Justin et al. |
| 2009/0292323 A1 | 11/2009 | Chirico et al. |
| 2010/0023010 A1 | 1/2010 | Nelson et al. |
| 2010/0087821 A1 | 4/2010 | Trip et al. |
| 2010/0094292 A1 | 4/2010 | Parrott |
| 2010/0094347 A1 | 4/2010 | Nelson et al. |
| 2010/0114181 A1 | 5/2010 | Lob |
| 2010/0131019 A1 | 5/2010 | Lob |
| 2010/0145397 A1 | 6/2010 | Overes et al. |
| 2010/0161061 A1 | 6/2010 | Hunt |
| 2010/0222884 A1 | 9/2010 | Greenhalgh |
| 2010/0241120 A1 | 9/2010 | Bledsoe et al. |
| 2010/0241123 A1 | 9/2010 | Middleton et al. |
| 2010/0241176 A1 | 9/2010 | Lob |
| 2010/0286481 A1 | 11/2010 | Sharp et al. |
| 2011/0077650 A1 | 3/2011 | Braun et al. |

FOREIGN PATENT DOCUMENTS

| | | |
|---|---|---|
| CA | 2452508 A1 | 1/2003 |
| CA | 2609175 A1 | 12/2005 |
| CA | 2678911 A1 | 9/2008 |
| CA | 2685046 A1 | 11/2008 |
| CN | 1533260 A | 9/2004 |
| CN | 101636119 A | 1/2010 |
| DE | 3146065 A1 | 5/1983 |
| DE | 3234875 A1 | 3/1984 |
| DE | 3922044 A1 | 2/1991 |
| EP | 145166 A2 | 6/1985 |
| EP | 0145166 A2 | 6/1985 |
| EP | 145166 A3 | 8/1986 |
| EP | 253526 A1 | 1/1988 |
| EP | 263292 A1 | 4/1988 |
| EP | 355035 A2 | 2/1990 |
| EP | 381462 A2 | 8/1990 |
| EP | 396519 A1 | 11/1990 |
| EP | 401650 A1 | 12/1990 |
| EP | 409769 A1 | 1/1991 |
| EP | 420542 A1 | 4/1991 |
| EP | 440371 A1 | 8/1991 |
| EP | 475077 A2 | 3/1992 |
| EP | 487669 A1 | 6/1992 |
| EP | 491211 A1 | 6/1992 |
| EP | 508710 A1 | 10/1992 |
| EP | 525352 A1 | 2/1993 |
| EP | 745352 A2 | 12/1996 |
| EP | 807419 A2 | 11/1997 |
| EP | 819413 A2 | 1/1998 |
| EP | 931513 A2 | 7/1999 |
| EP | 1099412 A2 | 5/2001 |
| EP | 1132051 A2 | 9/2001 |
| EP | 1155661 A1 | 11/2001 |
| EP | 1348384 A2 | 10/2003 |
| EP | 1391186 A1 | 2/2004 |
| EP | 1098600 B1 | 3/2004 |
| EP | 1396231 A1 | 3/2004 |
| EP | 1410765 A2 | 4/2004 |
| EP | 1442718 A1 | 8/2004 |
| EP | 1442729 A1 | 8/2004 |
| EP | 1454592 A2 | 9/2004 |
| EP | 1459686 A2 | 9/2004 |
| EP | 1495729 A1 | 1/2005 |
| EP | 1148825 B1 | 3/2005 |
| EP | 1148850 B1 | 4/2005 |
| EP | 1522268 A1 | 4/2005 |
| EP | 1227765 B1 | 5/2005 |
| EP | 1535579 A2 | 6/2005 |
| EP | 1563795 A1 | 8/2005 |
| EP | 1582159 A1 | 10/2005 |
| EP | 1582160 A1 | 10/2005 |
| EP | 1582161 A1 | 10/2005 |
| EP | 1582162 A1 | 10/2005 |
| EP | 1582163 A1 | 10/2005 |
| EP | 1582164 A1 | 10/2005 |
| EP | 1639953 A1 | 3/2006 |
| EP | 1669035 A1 | 6/2006 |
| EP | 1454592 A3 | 8/2006 |
| EP | 1700572 A1 | 9/2006 |
| EP | 1702572 A2 | 9/2006 |
| EP | 1714618 A2 | 10/2006 |
| EP | 1787593 A1 | 5/2007 |
| EP | 1808143 A1 | 7/2007 |
| EP | 1815813 A2 | 8/2007 |
| EP | 1820462 A1 | 8/2007 |
| EP | 1011464 B1 | 1/2008 |
| EP | 1905367 A1 | 4/2008 |
| EP | 1905392 A1 | 4/2008 |
| EP | 1915959 A2 | 4/2008 |
| EP | 1920721 A2 | 5/2008 |
| EP | 1923019 A1 | 5/2008 |
| EP | 1972308 A1 | 9/2008 |
| EP | 1987785 A2 | 11/2008 |
| EP | 2014261 A1 | 1/2009 |
| EP | 1459689 B1 | 4/2009 |
| EP | 1459689 B3 | 11/2009 |
| FR | 2653006 A1 | 4/1991 |
| GB | 2173565 A | 10/1986 |
| GB | 2268068 A | 1/1994 |
| JP | 1310664 A | 12/1989 |
| JP | 2008500140 A | 1/2008 |
| JP | 2010522046 A | 7/2010 |
| JP | 2010524642 A | 7/2010 |
| RU | 2004104359 A | 2/2005 |
| WO | WO8904150 A1 | 5/1989 |
| WO | WO8907056 A1 | 8/1989 |
| WO | WO9003764 A1 | 4/1990 |
| WO | WO9011726 A1 | 10/1990 |
| WO | WO9106260 A1 | 5/1991 |
| WO | WO9106265 A1 | 5/1991 |
| WO | WO9119461 A1 | 12/1991 |
| WO | WO9424938 A1 | 11/1994 |
| WO | WO9427507 A1 | 12/1994 |
| WO | WO9428824 A2 | 12/1994 |
| WO | WO9514433 A1 | 6/1995 |
| WO | WO9520362 A1 | 8/1995 |
| WO | WO9531159 A1 | 11/1995 |
| WO | WO9602202 A1 | 2/1996 |
| WO | WO9602203 A1 | 2/1996 |
| WO | WO9605783 A1 | 2/1996 |
| WO | WO9606041 A1 | 2/1996 |
| WO | WO9607161 A1 | 3/1996 |
| WO | WO9616607 A1 | 6/1996 |
| WO | WO9617557 A1 | 6/1996 |
| WO | WO9618354 A2 | 6/1996 |
| WO | WO9625118 A1 | 8/1996 |
| WO | WO9640476 A1 | 12/1996 |
| WO | WO9703611 A1 | 2/1997 |
| WO | WO9718775 A1 | 5/1997 |
| WO | WO9742602 A1 | 11/1997 |
| WO | WO9742912 A1 | 11/1997 |
| WO | WO9747251 A1 | 12/1997 |

| | | | | | | | |
|---|---|---|---|---|---|---|---|
| WO | WO9801077 | A1 | 1/1998 | WO | WO2004110300 | A2 | 12/2004 |
| WO | WO9805261 | A2 | 2/1998 | WO | WO2004112661 | A1 | 12/2004 |
| WO | WO9807392 | A1 | 2/1998 | WO | WO2005000159 | A2 | 1/2005 |
| WO | WO9819616 | A1 | 5/1998 | WO | WO2005020830 | A1 | 3/2005 |
| WO | WO9824380 | A1 | 6/1998 | WO | WO2005023085 | A2 | 3/2005 |
| WO | WO9826725 | A1 | 6/1998 | WO | WO2005032326 | A2 | 4/2005 |
| WO | WO9838918 | A1 | 9/1998 | WO | WO2005032340 | A2 | 4/2005 |
| WO | WO9846169 | A1 | 10/1998 | WO | WO2005039651 | A2 | 5/2005 |
| WO | WO9856301 | A1 | 12/1998 | WO | WO2005041799 | A1 | 5/2005 |
| WO | WO9922661 | A1 | 5/1999 | WO | WO2005044122 | A1 | 5/2005 |
| WO | WO9922662 | A1 | 5/1999 | WO | WO2005051971 | A1 | 6/2005 |
| WO | WO9937219 | A1 | 7/1999 | WO | WO2005055874 | A2 | 6/2005 |
| WO | WO9953843 | A1 | 10/1999 | WO | WO2005070314 | A1 | 8/2005 |
| WO | WO9955248 | A1 | 11/1999 | WO | WO2005092223 | A2 | 10/2005 |
| WO | WO9962416 | A1 | 12/1999 | WO | WO2005094693 | A1 | 10/2005 |
| WO | WO0006037 | A1 | 2/2000 | WO | WO2005094705 | A2 | 10/2005 |
| WO | WO0009024 | A1 | 2/2000 | WO | WO2005094706 | A1 | 10/2005 |
| WO | WO0012036 | A1 | 3/2000 | WO | WO2005096975 | A2 | 10/2005 |
| WO | WO0021455 | A1 | 4/2000 | WO | WO2005102196 | A1 | 11/2005 |
| WO | WO0025681 | A1 | 5/2000 | WO | WO2005107415 | A2 | 11/2005 |
| WO | WO0028906 | A1 | 5/2000 | WO | WO2005112804 | A1 | 12/2005 |
| WO | WO0030551 | A1 | 6/2000 | WO | WO2005122931 | A1 | 12/2005 |
| WO | WO0030569 | A1 | 6/2000 | WO | WO2005122932 | A2 | 12/2005 |
| WO | WO0038586 | A1 | 7/2000 | WO | WO2005123171 | A2 | 12/2005 |
| WO | WO0042954 | A2 | 7/2000 | WO | WO2006011152 | A2 | 2/2006 |
| WO | WO0044319 | A1 | 8/2000 | WO | WO2006020530 | A2 | 2/2006 |
| WO | WO0044321 | A2 | 8/2000 | WO | WO2006023793 | A2 | 3/2006 |
| WO | WO0044946 | A1 | 8/2000 | WO | WO2006026323 | A2 | 3/2006 |
| WO | WO0045712 | A1 | 8/2000 | WO | WO2006041460 | A1 | 4/2006 |
| WO | WO0045714 | A1 | 8/2000 | WO | WO2006042188 | A2 | 4/2006 |
| WO | WO0045715 | A1 | 8/2000 | WO | WO2006042189 | A2 | 4/2006 |
| WO | WO0045722 | A1 | 8/2000 | WO | WO2006042334 | A2 | 4/2006 |
| WO | WO0047119 | A1 | 8/2000 | WO | WO2006034396 | A3 | 5/2006 |
| WO | WO0048534 | A2 | 8/2000 | WO | WO2006051547 | A2 | 5/2006 |
| WO | WO0071038 | A1 | 11/2000 | WO | WO2006055448 | A1 | 5/2006 |
| WO | WO0076414 | A1 | 12/2000 | WO | WO2006063083 | A1 | 6/2006 |
| WO | WO0108571 | A1 | 2/2001 | WO | WO2006066228 | A2 | 6/2006 |
| WO | WO0128443 | A1 | 4/2001 | WO | WO2006068682 | A1 | 6/2006 |
| WO | WO0134045 | A1 | 5/2001 | WO | WO2010065855 | A1 | 6/2006 |
| WO | WO0149193 | A1 | 7/2001 | WO | WO2006089929 | A1 | 8/2006 |
| WO | WO0154598 | A1 | 8/2001 | WO | WO2006090379 | A2 | 8/2006 |
| WO | WO0160268 | A1 | 8/2001 | WO | WO2006034436 | A3 | 10/2006 |
| WO | WO0176493 | A1 | 10/2001 | WO | WO2006108067 | A2 | 10/2006 |
| WO | WO0176514 | A2 | 10/2001 | WO | WO2006113800 | A2 | 10/2006 |
| WO | WO0178015 | A2 | 10/2001 | WO | WO2006116760 | A2 | 11/2006 |
| WO | WO0180751 | A1 | 11/2001 | WO | WO2006116761 | A2 | 11/2006 |
| WO | WO0185042 | A1 | 11/2001 | WO | WO2006124764 | A1 | 11/2006 |
| WO | WO0213700 | A2 | 2/2002 | WO | WO2006124937 | A2 | 11/2006 |
| WO | WO0213716 | A1 | 2/2002 | WO | WO2006127904 | A1 | 11/2006 |
| WO | WO0217794 | A1 | 3/2002 | WO | WO2007002933 | A2 | 1/2007 |
| WO | WO0224088 | A2 | 3/2002 | WO | WO2007008177 | A1 | 1/2007 |
| WO | WO0234107 | A2 | 5/2002 | WO | WO2007009107 | A2 | 1/2007 |
| WO | WO0234148 | A2 | 5/2002 | WO | WO2007009123 | A2 | 1/2007 |
| WO | WO0237935 | A2 | 5/2002 | WO | WO2007011994 | A2 | 1/2007 |
| WO | WO0245606 | A1 | 6/2002 | WO | WO2007012046 | A2 | 1/2007 |
| WO | WO0249517 | A1 | 6/2002 | WO | WO2007025236 | A2 | 3/2007 |
| WO | WO02058575 | A1 | 8/2002 | WO | WO2007040949 | A2 | 4/2007 |
| WO | WO02067824 | A2 | 9/2002 | WO | WO2007041665 | A2 | 4/2007 |
| WO | WO02078555 | A1 | 10/2002 | WO | WO2006124937 | A3 | 5/2007 |
| WO | WO02089683 | A1 | 11/2002 | WO | WO2007053960 | A1 | 5/2007 |
| WO | WO03007830 | A1 | 1/2003 | WO | WO2007058943 | A2 | 5/2007 |
| WO | WO03013336 | A2 | 2/2003 | WO | WO2007059243 | A1 | 5/2007 |
| WO | WO03030760 | A1 | 4/2003 | WO | WO2007059246 | A1 | 5/2007 |
| WO | WO03043488 | A2 | 5/2003 | WO | WO2007059259 | A1 | 5/2007 |
| WO | WO03045257 | A2 | 6/2003 | WO | WO2007065137 | A2 | 6/2007 |
| WO | WO03047440 | A2 | 6/2003 | WO | WO2007069251 | A2 | 6/2007 |
| WO | WO03068090 | A1 | 8/2003 | WO | WO2007073488 | A2 | 6/2007 |
| WO | WO2004008949 | A2 | 1/2004 | WO | WO2007076308 | A2 | 7/2007 |
| WO | WO2004017817 | A2 | 3/2004 | WO | WO2007076374 | A2 | 7/2007 |
| WO | WO2004030549 | A1 | 4/2004 | WO | WO2007076376 | A2 | 7/2007 |
| WO | WO2004064603 | A2 | 8/2004 | WO | WO2007076377 | A2 | 7/2007 |
| WO | WO2004078220 | A2 | 9/2004 | WO | WO2007078692 | A2 | 7/2007 |
| WO | WO2004078221 | A2 | 9/2004 | WO | WO2007079237 | A2 | 7/2007 |
| WO | WO2004086934 | A2 | 10/2004 | WO | WO2007082151 | A2 | 7/2007 |
| WO | WO2004092431 | A1 | 10/2004 | WO | WO2007084239 | A2 | 7/2007 |
| WO | WO2004093633 | A2 | 11/2004 | WO | WO2007092813 | A2 | 8/2007 |
| WO | WO2004098453 | A2 | 11/2004 | WO | WO2007092841 | A2 | 8/2007 |
| WO | WO2004103209 | A2 | 12/2004 | WO | WO2007036815 | A2 | 9/2007 |
| WO | WO2004110292 | A2 | 12/2004 | WO | WO2007114982 | A1 | 10/2007 |

| | | | |
|---|---|---|---|
| WO | WO2007115108 A1 | 10/2007 | |
| WO | WO2007117571 A2 | 10/2007 | |
| WO | WO2007120539 A2 | 10/2007 | |
| WO | WO2007124130 A2 | 11/2007 | |
| WO | WO2007127255 A2 | 11/2007 | |
| WO | WO2007127260 A2 | 11/2007 | |
| WO | WO2007131002 A2 | 11/2007 | |
| WO | WO2007134134 A2 | 11/2007 | |
| WO | WO2007079237 A3 | 12/2007 | |
| WO | WO2007145824 A2 | 12/2007 | |
| WO | WO2008004229 A2 | 1/2008 | |
| WO | WO2008006117 A2 | 1/2008 | |
| WO | WO2008016910 A2 | 2/2008 | |
| WO | WO2008019397 A2 | 2/2008 | |
| WO | WO2008035849 A1 | 3/2008 | |
| WO | WO2008037454 A1 | 4/2008 | |
| WO | WO2008043254 A1 | 4/2008 | |
| WO | WO2008058960 A2 | 5/2008 | |
| WO | WO2008059027 A2 | 5/2008 | |
| WO | WO2008060277 A2 | 5/2008 | |
| WO | WO2008063265 A1 | 5/2008 | |
| WO | WO2008064346 A2 | 5/2008 | |
| WO | WO2008064347 A2 | 5/2008 | |
| WO | WO2008064350 A2 | 5/2008 | |
| WO | WO2008076330 A1 | 6/2008 | |
| WO | WO2008076357 A1 | 6/2008 | |
| WO | WO2008094407 A1 | 8/2008 | |
| WO | WO2007011353 A3 | 9/2008 | |
| WO | WO2008109566 A1 | 9/2008 | |
| WO | WO2008112308 A1 | 9/2008 | |
| WO | WO2008116170 A2 | 9/2008 | |
| WO | WO2008116175 A2 | 9/2008 | |
| WO | WO2008132728 A1 | 11/2008 | |
| WO | WO2008134287 A2 | 11/2008 | |
| WO | WO2008134758 A1 | 11/2008 | |
| WO | WO2008139456 A2 | 11/2008 | |
| WO | WO2008144709 A2 | 11/2008 | |
| WO | WO2007078692 A3 | 12/2008 | |
| WO | WO2008134287 A3 | 1/2009 | |
| WO | WO2009006622 A2 | 1/2009 | |
| WO | WO2009007331 A2 | 1/2009 | |
| WO | WO2009009772 A1 | 1/2009 | |
| WO | WO2009010412 A1 | 1/2009 | |
| WO | WO2009012347 A1 | 1/2009 | |
| WO | WO2009026070 A1 | 2/2009 | |
| WO | WO2009027325 A1 | 3/2009 | |
| WO | WO2009039430 A1 | 3/2009 | |
| WO | WO2006026397 A3 | 4/2009 | |
| WO | WO2009045751 A1 | 4/2009 | |
| WO | WO2009059227 A1 | 5/2009 | |
| WO | WO2009072125 A1 | 6/2009 | |
| WO | WO2009076086 A1 | 6/2009 | |
| WO | WO2009088376 A1 | 7/2009 | |
| WO | WO2009094478 A1 | 7/2009 | |
| WO | WO2008112912 A3 | 9/2009 | |
| WO | WO2009143374 A2 | 11/2009 | |
| WO | WO2008112875 A3 | 12/2009 | |
| WO | WO2009146457 A1 | 12/2009 | |
| WO | WO2009152270 A1 | 12/2009 | |
| WO | WO2009152272 A1 | 12/2009 | |
| WO | WO2009152273 A1 | 12/2009 | |
| WO | WO2008139456 A3 | 2/2010 | |
| WO | WO2010037038 A2 | 4/2010 | |
| WO | WO2010056895 A1 | 5/2010 | |
| WO | WO2010091242 A1 | 8/2010 | |
| WO | WO2010035156 A1 | 11/2010 | |

OTHER PUBLICATIONS

App No. PCT/US 09/30971 Written Opinion of the International Searching Authority, Mar. 2009.
App No. PCT/US/2011/21074 International Search Report, May 2011.
App No. PCT/US2011/21074 Written Opinion of the International Searching Authority, May 2011.
App No. PCT/US/2011/021735 International Search Report, May 2011.
App No. PCT/US2011/021735 Written Opinion of the International Searching Authority, May 2011.
App No. PCMS2011/027597 International Search Report, Jul. 2011.
App No. PCT/US2011/027597 Written Opinion of the International Searching Authority, Jul. 2011.
App No. PCT/US2011/027602 International Search Report, Jul. 2011.
App No. PCT/US2011/027602 Written Opinion of the International Searching Authority, Jul. 2011.
Putnam, Matthew D., et al., "Distal Radial Metaphyseal Forces in an Extrinsic Grip Model: Implications for Post fracture Rehabilitation," American Society for Surgery of the Hand, 25A: 469-475, May 2000.
Higgins, Thomas F., et al., "A Biomechanical Analysis of Fixation of Intra-Articular Distal Radial Fractures with Calcium-Phosphate Bone Cement," The Journal of Bone and Joint Surgery, 84:1579-1586, Needham, Massachusetts, Sep. 2002.
Stoeckel et al., "Self-Expanding Nitinol Stents—Material and Design Considerations," Nitinol Devices & Components, Fremont, California, 2003.
Rozenthal, Tamara D., et al., "Functional Outcome and Complications After Volar Plating for Dorsally Displaced, Unstable Fractures of the Distal Radius," The Journal of Hand Surgery, 31A: 359-365, Mar. 2006.
Keast-Butler, Oliver, et al., "Biology Versus Mechanics in the Treatment of Distal Radial Fractures," The Journal of Orthopedic Trauma, 22: S91-S95, Philadelphia, Pennsylvania, Sep. 2008.
Mudgal, Chaitanya S., et al., "Plate Fixation of Osteoporotic Fractures of the Distal Radius," The Journal of Orthopedic Trauma, 22: S106-S115, 2008, Philadelphia, Pennsylvania, Sep. 2008.
Bogoch, Earl R., et al., "The Osteoporosis Needs of Patients with Wrist Fractures," The Journal of Orthopedic Trauma, vol. 22, No. 8, Supplement, Philadelphia, Pennsylvania, Sep. 2008.
Arora, Rohit, et al., "A Representative Case of Osteoporotic Distal Radius Fracture," The Journal of Orthopedic Trauma, vol. 22, No. 8, Supplement, Philadelphia, Pennsylvania, Sep. 2008.
Firoozabadi, Reza, et al., "Qualitative and Quantitative Assessment of Bone Fragility and Fracture Healing Using Conventional Radiography and Advanced Imaging Technologies—Focus on Wrist Fracture," The Journal of Orthopedic Trauma, vol. 22, No. 8, Supplement, Philadelphia, Pennsylvania, Sep. 2008.
Goldhan, Jorg, et al., "What Counts: Outcome Assessment After Distal Radius Fractures in Aged Patients," The Journal of Orthopedic Trauma, vol. 22, No. 8, Supplement, Philadelphia, Pennsylvania, Sep. 2008.
Hoang-Kim, Amy, et al., "Wrist Fractures in Osteoporotic Patients," The Journal of Orthopedic Trauma, vol. 22, No. 8, Supplement, Philadelphia, Pennsylvania, Sep. 2008.
Kettler, Mark, et al., "Do We Need to Include Osteoporosis in Today's Classification of Distal Radius Fractures?" The Journal of Orthopedic Trauma, vol. 22, No. 8, Supplement, Philadelphia, Pennsylvania, Sep. 2008.
Downing, Martin R., et al., "Assessment of Inducible Fracture Micromotion in Distal Radial Fractures Using Radiostereometry," The Journal of Orthopedic Trauma, vol. 22, No. 8, Supplement, Philadelphia, Pennsylvania, Sep. 2008.
Suhm, Norbert, et al., "Injectable Bone Cement Augmentation for the Treatment of Distal Radius Fractures: A Review," The Journal of Orthopedic Trauma, vol. 22, No. 8, Supplement, Philadelphia, Pennsylvania, Sep. 2008.
Van Lenthe, G. Harry, et al., "Quantification of Bone Structural Parameters and Mechanical Competence at the Distal Radius," The Journal of Orthopedic Trauma, vol. 22, No. 8, Supplement, Philadelphia, Pennsylvania, Sep. 2008.
Parkinson, Ian H., et al., "Whole Bone Geometry and Bone Quality in Distal Forearm Fracture," The Journal of Orthopedic Trauma, vol. 22, No. 8, Supplement, Philadelphia, Pennsylvania, Sep. 2008.
"Medtronic—Abdominal Stent Graft System, Instructions for Use," Medtronic, Inc., Minneapolis-Minnesota, 2008.
Jupiter, Jesse B., et al., "Operative Management of Distal Radial Fractures with 2.4-Millimeter Locking Plates. A Multicenter Prospective Case Series," The Journal of Bone and Joint Surgery, 91: 55-65, doi:10.2106-JBJS.G.01498, Needham, Massachusetts, Jan. 1, 2009.
US 7,063,700, 06/2006, Michelson (withdrawn)
US 7,201,752, 04/2007, Huebner et al. (withdrawn)

* cited by examiner

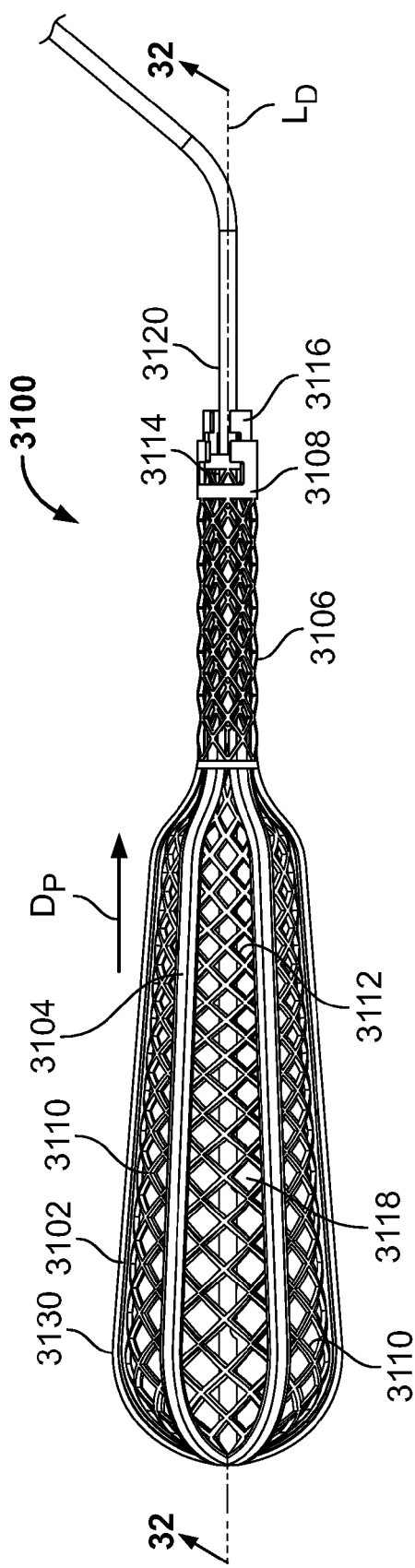
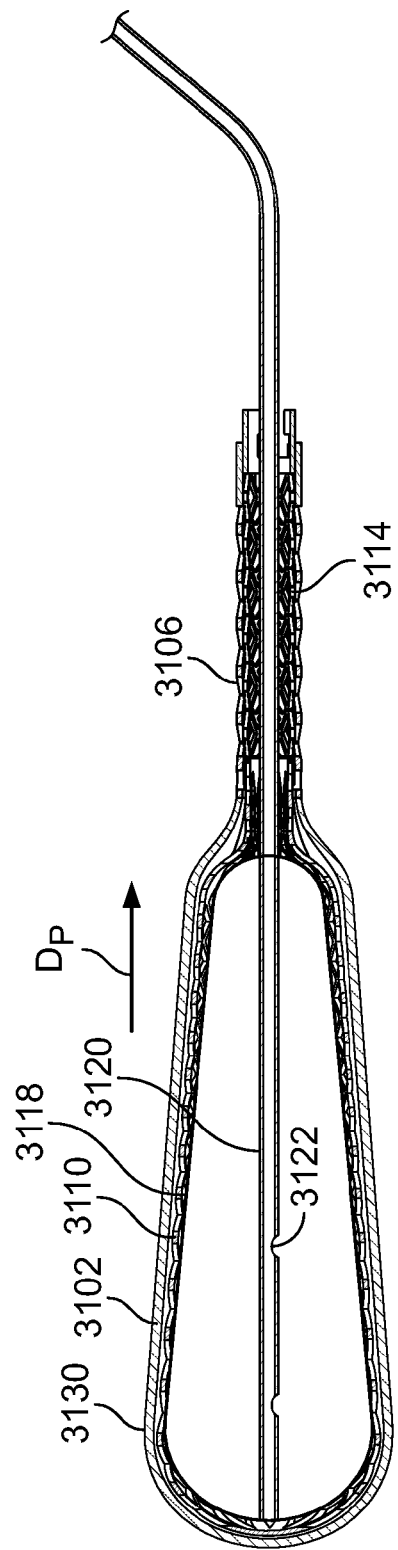
FIG. 31
FIG. 32

APPARATUS AND METHODS FOR FRACTURE REPAIR

CROSS-REFERENCE TO RELATED APPLICATIONS

This application is a nonprovisional of U.S. Provisional Applications Nos. 61/020,778, filed on Jan. 14, 2008, and 61/090,999, filed on Aug. 22, 2008, both of which are hereby incorporated by reference in their entireties.

FIELD OF TECHNOLOGY

Aspects of the disclosure relate to providing apparatus and methods for repairing bone fractures. In particular, the disclosure relates to apparatus and methods for repairing bone fractures utilizing a device that is inserted into a bone.

BACKGROUND

Currently, there are many known ways to treat long bone fractures. Common fracture treatments include: (1) non-surgical immobilization; (2) osteosuture and tension band technologies; (3) percutaneous fixation (e.g., using pins, wires, screws etc.); (4) rigid intramedullary nailing (e.g., using a large rod and external screws); (5) flexible plate osteosynthesis (e.g., a "load sharing" suture); (6) arthroplasty (e.g., using a prosthesis); (7) plating and other indication-specific techniques. Severe fractures that meet certain clinical criteria may require surgical repair rather than non-surgical immobilization.

The midshaft of an elongated or long bone is typically classified as the diaphysis. The end of such a bone is typically classified as the epiphysis. Bone that is transitional between the midshaft and the end is typically classified as the metaphysis.

Metaphysis and epiphysis bone are typically less dense, more cancellous (porous), and less cortical than diaphysis bone. Repair of metaphysis and epiphysis fractures are often complicated by their proximity to a joint. Because of such bone quality and anatomical differences, fixation of plates and screws in metaphysis and epiphysis bone is typically more difficult than fixation of plates and screws in diaphysis bone. This may be especially true if the patient is elderly and suffers from osteoporosis.

In general, fracture fixation may provide longitudinal (along the long axis of the bone), transverse (across the long axis of the bone), and rotational (about the long axis of the bone) stability. Fracture fixation may also preserve normal biologic and healing function.

There are two primary categories for surgical fixation: (1) a device that is within the skin (internal fixation); and (2) a device that extends out of the skin (external fixation). There are two common types of internal fixation approaches for long bone surgery (a) a plate that is screwed to the outside of the bone; or (b) a rod that goes down the center of the bone.

Plates and screws are characterized by relatively invasive surgery, support of fractured bone segments from one side outside of bone, and screws that anchor into the plate and through the entire bone. Successful repair is dependent on fracture pattern, bone quality, physician skill set, and patient tolerance of a foreign body. Plates and screws may not properly address the alignment and stability requirements for periarticular and intrarticular fractures.

Intramedullary rods or nails, such as those used in mid shaft treatments, are more effective than plates and screws at minimizing soft-tissue trauma and complications. However, rods and nails often do not stabilize multi-segment fractures in many cases. The typical intramedullary rod or nail is fixed in diameter and is introduced into the medullary canal through an incision. In cases where there is a medullary plenum larger than the rod, rotational and transverse stability may be compromised. If a larger rod is used, reaming of the entire shaft length may be necessary. Such reaming may thin out existing cortical bone support. Also, predetermined threaded screw holes in the rods may limit the ways in which different fracture patterns can be reduced and stabilized.

Flexible intramedullary rod-like solutions utilize structures that can be inserted into the medullary cavity through an access site, which can then become rigid. These solutions may be easier for the user to install than rigid intramedullary rods. These structures may be reinforced with polymers or cements. Flexible intramedullary solutions, similar to rigid intramedullary rods, may have limited benefits for periarticular or intrarticular fractures. Multi-segment fractures, of either the midshaft or end-bone, require alignment and stability in a manner that generates adequate fixation in multiple directions.

Midshaft fractures and end-bone fractures are fundamentally different. The loading conditions, fracture patterns, alignment needed, and compression force to promote healing are different. Midshaft fractures have ample bone material on either side of the fracture in which anchors may be driven. End-bone fractures, especially on the articular surface may have thin cortical bone, soft cancellous bone, and minimal anchoring locations.

Midshaft fractures tend to be loaded primarily in bending and torsion. End-bone fractures tend to be loaded in complex and multi-directional stress patterns. Midshaft repair approaches, therefore, may not be appropriate for repair of end-bone fractures.

Appropriate sizing of an implant helps realignment and healing of the fracture. As a result, many different sizes of known repair products are often stored in inventories to ensure proper matching of the implant device to a patient's anatomy. The inventories may be a burden to hospitals and insurance carriers, but they may be necessary to provide to a surgeon intraoperative flexibility.

It would be desirable, therefore, to provide apparatus and methods for proper anatomic alignment and stabilization, while reducing trauma and complications.

BRIEF DESCRIPTION OF THE DRAWINGS

The objects and advantages of the invention will be apparent upon consideration of the following detailed description, taken in conjunction with the accompanying drawings, in which like reference characters refer to like parts throughout, and in which:

FIG. 31 is a side view of apparatus in accordance with the principles of the invention;

FIG. 32 is a sectional view of apparatus shown in FIG. 31;

DETAILED DESCRIPTION OF THE INVENTION

Figure 1:
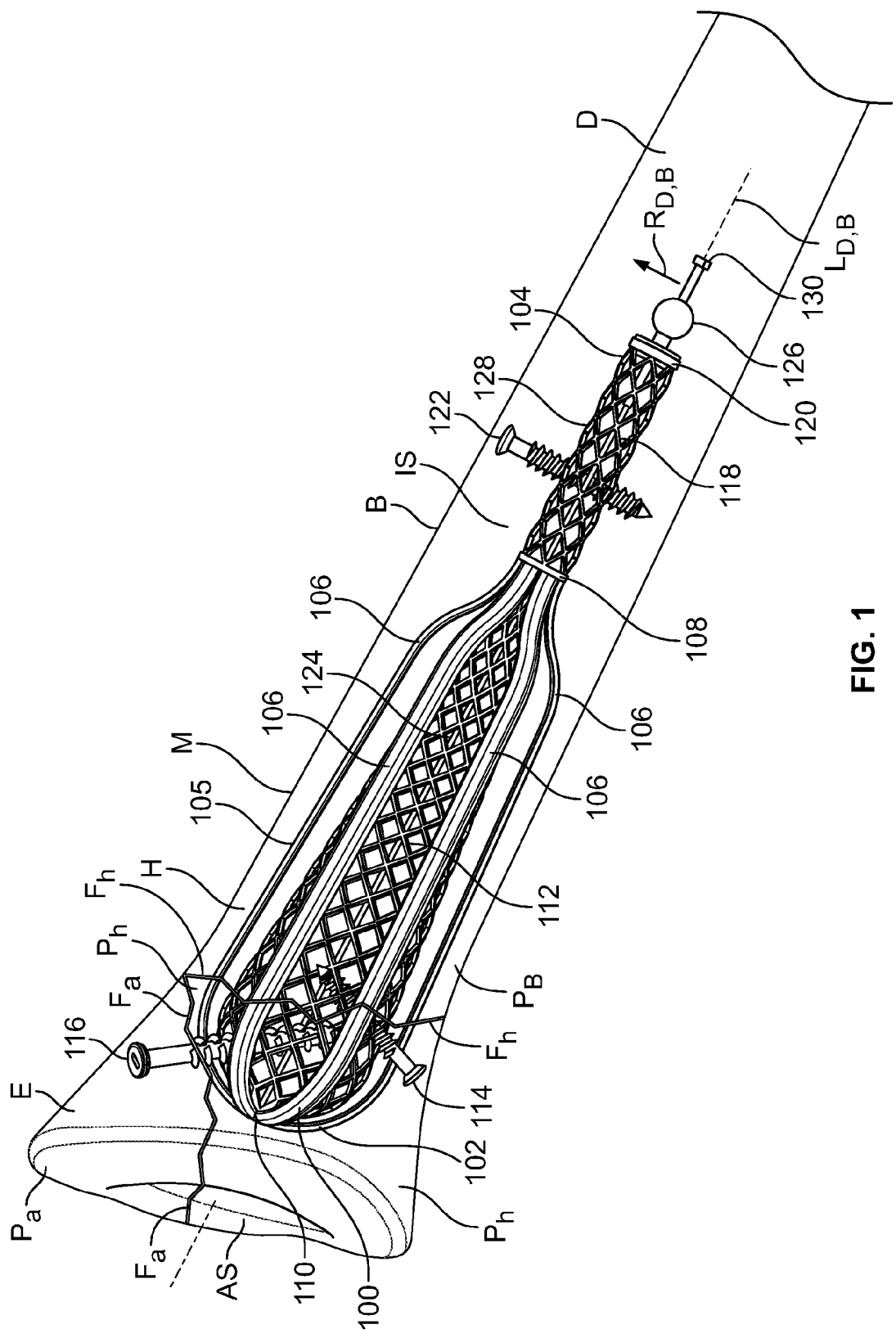
FIG. 1 is a side view of apparatus in accordance with the principles of the invention disposed.

Apparatus and methods for fracture repair are provided. The apparatus may include a structural support for positioning a first bone segment relative to a second bone segment. The structural support may be configured to be deployed in an inner cavity of a bone. The apparatus may include an anchoring substrate. The anchoring substrate may be configured to compress the first bone segment to the second bone segment. The anchoring substrate may be configured to be deployed in the inner cavity.

The term "bone segment" may refer to portions or fragments of a bone. The term "structural support" may include a "structural cage."

The structural support may be self-expanding. The structural support may be expanded by balloon. The structural support may be expanded by mechanical actuation. The anchoring substrate may be self-expanding. The anchoring substrate may be expanded by balloon. The anchoring support may be expanded by mechanical actuation.

The structural support may be used as a frame to position and align the bone segments. Anchors may used to secure the bone segments to the anchoring substrate. The anchoring substrate may be tensioned to compress the bone segments against each other. Some embodiments of the apparatus may include a central axis member. The central axis member may be used in conjunction with expansion of one or both of the structural support and the anchoring substrate. The central axis member may be used in conjunction with the tensioning of the anchoring substrate after anchors are placed. A proximal anchor may be used to fix one end of the apparatus to a bone segment to "lock in" the tensioning of the anchoring substrate.

The apparatus may include delivery apparatus. The delivery apparatus may deliver one or more portions of the apparatus, such as the structural support and the anchoring substrate, through an access hole in the bone and into the intramedullary cavity in the bone. The portions may be delivered in a contracted or collapsed state. The portions may then be expanded for repair of the fracture.

The apparatus and methods may involve reducing, aligning, compressing and/or stabilizing the fracture from within the intramedullary cavity. In some instances, the resulting stabilized bone may then heal while maintaining mobility of the patient.

The apparatus and methods may provide stabilization in axial bending, torsion, rotation, compression, and may provide inter-segment tension or compression.

The stabilization may repair compacted and impacted fractures, control length, and control alignment of the fracture segments. The apparatus may separate the tasks of revision, reduction, fixation, stabilization, rotation and offset.

The apparatus and methods may distribute load between the apparatus and native bone. The apparatus may have flexibility and modulus that are similar to native bone. Some embodiments may provide apparatus that is selectively weaker than or stronger than the native bone to promote beneficial fracture healing response.

The apparatus and methods may be used for closed reduction, open reduction, and minimally invasive surgical procedures ("MIS"). The apparatus and methods may facilitate arthroscopic surgical procedures. The apparatus and methods may provide percutaneous fracture repair. In such repair, the apparatus may be deployed into the cavity of a bone through a small incision.

The apparatus may be delivered at a point other than that of the fracture site. This may help reduce soft tissue damage. The apparatus may be delivered into an intramedullary cavity through a small access hole that may be placed along the midshaft of the long bone in an area in which minimal soft tissues would need to be displaced.

The apparatus and methods may reduce the need to place foreign bodies in muscle, tendon and nerve areas. As such, the apparatus and methods may reduce tissue erosion and disintegration. Preservation of the soft tissue may reduce chronic pain and stiffness. The apparatus and methods may reduce infection risk because of its noninvasiveness.

In some embodiments, the apparatus and methods may be made completely from biologically friendly metals such as titanium and Nitinol. Such materials reduce the risk of infection and do not generally interfere with normal biological processes within the fractured bone.

The apparatus and methods may be used to repair many different types of bones. For example, the apparatus and methods may be used to repair long bones, short bones, flat bones, irregular bones, and sesamoid bones.

The apparatus and methods may be used to repair many different types of fractures. For example, the apparatus and methods may be used to repair comminuted fractures, epiphyseal fractures, metaphyseal fractures, mid shaft fractures, intra-articular fractures, periarticular fractures, multipart fractures and other types of fractures.

The apparatus may be used in the reconstruction of fractured joints. The apparatus and methods may also facilitate such joint replacements by providing an adequate anchoring substrate. For example, the apparatus and methods may provide stable anchoring for a prosthesis, and reduce aseptic loosening.

The terms "end-bone" and "end-bone fracture" may be used to refer to fractures that occur in the epiphyseal or metaphyseal region of long bones. Such fractures include peri-articular and intra-articular fractures.

The apparatus and methods may be used to treat osteoporotic bone, indications involving poor bone quality. In connection with such indications, the apparatus may compensate for deficiencies in native bone and may reduce concerns regarding stress shielding. The apparatus and methods may be used in connection with fusion of bones and joints for various indications including arthritis.

The apparatus and methods may be used in conjunction with bone cement or in place of bone cement. In some embodiments, the apparatus may act as a bone filler. For example, the apparatus may be used for filling bone void in connection with the treatment of cysts and tumors. The apparatus may behave as an osteoconductive scaffold to promote bone growth.

The apparatus and methods may be used in connection with provisional alignment for staged repair procedures, such as revisions, high energy trauma, or other cases in which there is infection or soft tissue that needs to heal before bone fixation is completed. The apparatus and methods may be used in combination with various antibiotics that promote healing.

The structural support may prevent bone segments from moving inward, so the apparatus may reduce the likelihood of collapse of the fracture. The apparatus may conform to the shape of bone and may thus minimize undue stresses. For example, the apparatus and methods may reduce hoop stress by selecting a degree of implant expansion or stiffness.

The apparatus may be self-centering, because it expands into the bone cavity. Many of the cavities are not straight like a pipe; they vary depending on the anatomy. The apparatus may be straight, bent, curved, and cavity-compliant.

The apparatus and methods may provide anchoring at the distal end of the apparatus. This feature may be used for repairs of articular fractures and fractures with small or mobile bone segments.

The apparatus and methods may provide for the use of small anchors, because the apparatus provides structural support for the bone segments that require anchoring.

The apparatus and methods may provide anchoring in any suitable direction. Some embodiments may provide anchoring in any plane.

Because the anchoring substrate expands toward the inside surface of the bone segments, relatively shorter anchors may be used in comparison with typical repair methods. For the same reason, the use of a screw that is longer than required to engage the anchoring substrate will not result in driving the screw into or through bone that is opposite the anchored segment. This is so because the screw will terminate in the intramedullary cavity.

The apparatus and methods may be used in conjunction with plates, screws, pins, external fixators, replacement joints, bone graft matrices, factor based bone substitutes, and cell based bone substitutes.

Delivery Instrument

The delivery instrument may deliver the apparatus to the intramedullary cavity through an access hole in the bone. The delivery instrument may be used to remove the apparatus from the intramedullary cavity through the access hole. The delivery instrument may engage the apparatus by any suitable mechanism, including one or more of threading, a socket, a pin, a snap, a collet, a cable, and any other suitable mechanism.

The mechanism may deliver, expand, adjust, rotate, lock, release and recapture the apparatus. Each of the acts, and other suitable acts, may be performed independently on the structural cage, the anchor substrate, the central axis member, locking features, and associated coupling mechanisms. The delivery device may include a handle set capable of delivering the forces needed to actuate the mechanism or mechanisms.

The delivery instrument may include a sheath to help deliver the apparatus in a compacted state. The shaft of sheath may be bendable to access the intramedullary cavity. In some embodiments, the delivery instrument may not have a sheath. In those embodiments, the delivery instrument may push the apparatus into place unguarded.

The delivery instrument may be radio opaque in whole or in part.

In some embodiments, the delivery instrument may be attached to a flexible scope or endoscope. In some embodiments, the delivery instrument may be integrated with the flexible scope or endoscope.

Structural Support

The structural support may provide one or more of axial, bending, torsional, and positional structural support to the fracture segments. The structural support may reduce or eliminate adverse effects such as stress risers. The structural support may provide a guide or surface for alignment of the fracture segments during reduction and healing.

The structural support may be configured in a contracted state and introduced through a hole in the shaft of the bone. The structural support may have sufficient flexibility in the contracted state to conform to curvature in an access pathway.

The structural support may be positioned inside the intramedullary cavity near a fracture site. The structural support may be expanded. When expanded, the structural support may be rigid. The structural support may be expanded sufficiently to fill the available cavity and/or displace low density material that may border the cavity. Expansion may vary along the surface of the structural support such that the expanded structural support may conform to irregular cavity shapes.

In some embodiments, an expansion state may be maintained with or without the structural support being in a stressed condition. Radial pressure against the cavity walls can be tailored along the length of the structural support. The structural support may provide strain relief in desired locations to promote healing.

The expansion of the structural support may be elastic. This may be achieved using a spring material that returns to its original configuration shape or pressure after release from the contracted state.

The expansion of the structural support may be plastic. The structural support may be deformed into a desired expanded configuration. The deformation may be achieved by a mechanism, such as a lever or reciprocating manipulators that change the length of the structural support. The lever or manipulators may shorten the distance between two portions of the structural member. Shortening the distance may cause radial expansion of a portion of the structural support.

Force for shortening the distance may be supplied by a central axis member that may transect the structural support. The resulting shape could be derived from a combination of the expansion described and the resistance of the cavity walls.

The deformation may be achieved by direct force, such as by a balloon.

The structural support may be expanded torsionally. The torsional expansion may be either elastic or plastic in nature. For example, the distal end of the structural support may be rotated relative to the proximal end. The structural support may then expand to fill the cavity.

Many different materials could be utilized to achieve the desire expansion and strength features described.

The structural support may include support members that form a cage or a portion of a cage. The support members may have one or more of many different configurations. The structural support may have any suitable number of support members. For example, the number of support members may be 1, 2, 3, 4, 5, 6, 7, 8, 10, 25, 50, 100 or more.

The support members may have any suitable cross-sectional shape. For example, the support members may have one or more of the following cross-sectional shapes: round, flat, rectangular, "I" beam, tubular, stranded, twisted and many others.

The structural support may have any suitable shape. For example, the structural support may be round, cylindrical, flat, rectangular, spiral, helical, wisk or egg beater like, egg like or oval, branching or free-ended.

The structural support may be constructed from unitary or multi-component assemblies. The structural support may be:

machined, laser cut form a tube, etched from a sheet, assembled and joined strips, molded, deposited and or sintered.

The proximal end of the structural support may join and lock to the anchor substrate. The proximal end may also interface with the delivery instrument. The proximal end may have suitable features for delivery, actuation, locking and release. Such features may include, for example, one or more thread, socket, pin, snap, collet, cable mechanisms and other suitable mechanism.

Anchoring Substrate

The apparatus may include one or more anchoring substrates. An anchoring substrate may receive one or more anchors and hold them in a desired position with or without the joint assistance of the structural support and with or without cancellous bone. The anchoring substrate may be sized and shaped such that it may be engaged by an anchor that penetrates into the intramedullary space.

The anchoring substrate may be sized and shaped such that once the anchoring element penetrates into the intramedullary space, the anchoring substrate may engage the anchor. The anchoring substrate may provide to an anchor tension that is supplemental to tension caused by the engagement of the anchor and the anchoring substrate.

There are several methods by which the anchors and the anchoring substrate may engage.

Some of the methods are passive engagement methods. In passive engagement, anchoring substrate features may be appropriately sized to engage an anchor. For example, the anchor and anchoring substrate may be configured such that they engage in a manner analogous to a screw and hole. A laser cut structure could take any shape necessary to achieve appropriate anchor engagement and retention. The receiving cavities ("cells") could be round, square, slotted, triangle, or any shape that facilitated engagement. The geometry of the cells may be that of a shortening design. The cells may form a matrix, a "fabric," or a "cloth." The anchoring substrate may include a single layer or multiple layers.

Matrix characteristics may be varied along an axis of the anchoring substrate to provide anchoring characteristics along the axis. For example, cell geometry may be varied to provide engagement with different types of anchors. Anchoring substrate thickness may be varied to provide different degrees of anchor retention strength and forces.

There are several approaches to active engagement. One such approach is cell size reduction. The anchoring substrate may be deformed such that the size of cells is reduced. The cell size reduction may cause tightening (or locking) of the cell onto the anchor.

Another such approach involves relative displacement between first and second anchoring substrates. The relative displacement effectively reduces cell size when corresponding cells are offset from each other. The relative displacement may be axial, rotational, radial, etc . . . . The relative displacement may trap an anchor between the two displaced anchoring substrates and effectively lock or hold the anchor. Cells of selected shapes, either similar or different, in the first and second anchoring substrates may be moved in a cooperative manner to trap or engage the anchor.

Another such approach involves twisting the anchoring substrate. This action may be similar to stretching and locking the anchor in the medium of the substrate. Other approaches include wrapping, plicating and bunching the anchoring substrate. A plicated or bunched configuration may exert force by having several layers of material binding on the anchor at one time, effectively wire tying the anchor.

The arrangement of different portions of the anchoring substrate may be selected to facilitate engagement with an anchor. Portions of the anchoring substrate may extend radially away from a central or longitudinal axis of the apparatus or the anchoring substrate. Portions of the anchoring substrate may be supported in a perpendicular orientation with respect to the axis.

After the anchoring substrate is engaged with an anchor, the anchoring substrate may apply tension to the anchor. The tension may urge the anchor to move relative to the structural element. This can be accomplished by moving the anchoring substrate in an axial direction relative to the structural member. If the anchoring substrate is moved proximally relative to the structural support, tension would be applied to the anchors and their corresponding fracture segments.

The tension may be achieved by reducing the diameter of the anchoring substrate. This can be accomplished though lengthening and therefore reducing the anchoring substrate diameter. The tension may be applied by wrapping, folding, twisting, rotating or radially pulling in the anchoring substrate. The plicated or bunched configuration mentioned above may be used for this approach.

In some embodiments, the anchoring substrate may be internal to the structural support. In some embodiments, the anchoring substrate may be external to the structural support. Some embodiments may include one or more anchoring substrates that are internal to the structural support and one or more anchoring substrates that are external to the structural support. In some embodiments, the anchoring substrate may be attached to the structural support.

In some embodiments, the anchoring substrate may cooperate mechanically with the structural support. The anchor substrate may provide structural integrity to the device. For example, the matrix may include interlockable features. The interlocking features may become interlocked during or after the anchoring substrate is expanded.

In some embodiments, the anchoring substrate may be mechanically independent of the structural support. This may allow for relative movement between the anchoring substrate and the structural support.

The anchoring substrate may be expandable. The anchoring substrate may expand simultaneously with the structural support. The anchoring substrate may be expanded by the structural support. The anchoring substrate may be expanded by a delivery device such as a balloon. The substrate may be self-expanding. Self-expanding embodiments may include spring like elements. Self-expanding embodiments may include elements that include shape memory materials, such as shape memory alloys. In some embodiments, the anchoring substrate may be non-expanding. In some embodiments, the anchoring substrate may be expandable by mechanical actuation.

The anchoring substrate may be constructed in many different forms and of many different materials. The forms may include, for example, braid, mesh, weave, strand, laser cut members, deposited members or other filament construction. The anchoring substrate cells may be round elements, square element, rectangular elements, or profiled, or a combination of cell types. The anchor substrate cells may be designed to mimic bone and act as a growth or graft scaffold.

The anchoring substrate may be made form a unitary element such as an extruded tube or flat sheet with a pattern cut into it that would facilitate engagement. Examples include a laser-cut tube, a stamped or etched sheet, and other suitable approaches.

The anchoring substrate may be made of many materials including but not limited to; Nitinol, Titanium, steel alloys, polymers, porous materials, sponge like materials, sintered metal, etched materials, deposited material, extruded material and molded materials.

Anchors

Anchors may facilitate the attachment of bone segments to the anchoring substrate. The anchors may mate, couple, engage, lock and otherwise interact with the anchoring substrate. Some of the anchors may be configured to engage the bone. Some of the anchors may be configured to not engage the bone.

An anchor may have an elongated element. The elongated element may include one or catch features that are configured to engage the anchoring substrate. The engagement may be occur substantially immediately after penetration of the anchoring substrate by the anchor. The engagement may occur only after a predetermined length of the elongated member has passed into the anchoring substrate. Some anchors may lock to the anchoring substrate. Some anchors may not lock to the anchoring substrate Catch features may be self-actuating. Catch features may be user actuated.

Anchors may have any suitable length. Anchors of different lengths may be used in conjunction with the apparatus. The anchors can be configured to enter and engage the anchoring substrate with an end portion of the anchor. Those anchors, after they are locked, may terminate inside the anchoring substrate. Some anchors may be configured to pass through the anchoring substrate and engage bone on an opposite side of the anchoring substrate. Some anchors may be configured to not engage bone on either side of the anchoring substrate. Example anchors include: screws, helical elements, T bar, barbed features, anchors cut from a tube, with tabbed features.

In some embodiments, anchors may be used in conjunction with buttress elements such as plates, washers, spacers and the like.

A proximal anchor may be inserted to anchor a proximal portion of the anchoring substrate to the bone. In some embodiments, the proximal anchor may be engaged to preserve tension in the anchoring substrate. In some embodiments, the proximal anchor may be configured to adjust the tension.

Central Axis Member

In embodiments that include a central axis member, the central axis member may be used to position the apparatus, actuate one or more changes (e.g., of expansion state or stress state) of the apparatus, move one portion of the apparatus relative to another portion of the apparatus and provide mechanical support (e.g., rigidity) to the apparatus.

In some embodiments, the apparatus may have a distal end and a proximal end. The support structure may have a distal end and a proximal end. The anchoring substrate may have a distal end and a proximal end. The central axis member may have a distal end and a proximal end. In some embodiments, the central axis member may extend proximally beyond the proximal ends of the structural support and the anchoring member. In those embodiments, an intermediate portion of the central axis member may generally align with the proximal ends of the structural support and the anchoring substrate.

The central axis member may be used to maintain rigidity of the structural support and/or the anchoring substrate. In those embodiments, the distal end of the central axis member may be longitudinally fixed to the distal end of the structural support and/or the anchoring substrate. The proximal end or intermediate portion of the central axis member may be longitudinally fixed to the proximal end of the structural support and/or the anchoring substrate.

The central axis member may be used to adjust the length of the structural support and/or the anchoring substrate. In those embodiments, the distal end of the central axis member may be fixed to the distal end of the structural support and/or anchoring substrate. The proximal ends of the structural support and/or anchoring substrate may be longitudinally movable (whether linearly, rotationally or otherwise) with respect to the central axis member. As such, the central axis member may be used to expand the structural support or the anchoring substrate. The central axis member may be used to lock the apparatus in an expanded configuration. The central member may be locked in place by other elements of the apparatus.

In some embodiments, the central axis member may be used to place a lower or upper limit on the longitudinal separation between distal and proximal ends of the support structure and/or anchoring substrate. This may be accomplished by providing detents at selected locations along the central axis member.

In some embodiments, the central axis member may be used to linearly displace the structural support relative to the anchoring substrate or the anchoring substrate relative to the support structure. The central axis member may be used to linearly displace one anchoring substrate relative to another anchoring substrate. In such embodiments, the central axis member may be longitudinally fixed to whichever of the structural support and the anchoring substrate that is to be moved relative to another.

The central axis member may be used to mechanically load the structural support and/or the anchoring substrate. The load may be in tension, compression or rotation. The load may be applied by suitable engaging the central axis member with a portion of the structural support and/or anchoring substrate. The central axis member may then be loaded, for example, at its proximal end. The central axis member may then transfer the load through the engagement with the structural support and/or anchoring structure.

Where the central axis member is longitudinally fixed to the structural support and/or anchoring substrate, it may remain free to rotate. Where the central axis member is not longitudinally fixed, the apparatus may include suitable bushings, bearings, frictional surfaces and the like to permit suitable linear displacement and/or rotation between the central axis member and the structural support and/or anchoring substrate.

For example, the central axis member may be longitudinally fixed to the distal end of the structural support and rotationally fixed to the proximal end of the anchoring substrate. The distal end of the anchoring substrate may or may not be rotationally fixed to the distal end of the support structure. The central axis may thus be used in different configurations to deform (e.g., wrap, fold, twist, etc.) the anchoring substrate. Similar configurations may be used to deform the structural support.

In some embodiments, the central axis member may include or serve as an anchoring substrate. The central axis member may be removable so that it may be removed from the apparatus after its desired effect is achieved.

The central member may be flexible or rigid. The central member may be integral with one or both of the structural support and the anchoring substrate. The central axis member may include one or more cables, coils, thread, braids, extrusions, beading, rods, bundles, strands, meshes, nested elements and the like.

Apparatus Removal

The apparatus may be removable from the bone. Approaches for removal may include collapsing the apparatus.

In some instances, tissue may grow into interstices of the apparatus. Energy (e.g., vibrations, ultrasonic energy, heat and the like) may be coupled into the apparatus to release the tissue. When heat energy is used, the heat may be generated from energy in any suitable form, such as radio frequency, microwave, induction, electrical resistance, and others.

The apparatus and methods may include removal instruments such as a hollow drill, a coring drill and the like. The apparatus may fit inside one or more of such instruments.

Bone Ingrowth

One or more surfaces of the apparatus may be coated with agents that promote bone ingrowth. The agents may include calcium phosphate, heat treated hydroxylapatite, Basic fibroblast growth factor (bFGF)-coated hydroxyapatite, hydroxyapatite/tricalcium phosphate (HA/TCP), and other suitable agents, including one or more of those listed in Table 1.

One or more surfaces of the apparatus may be coated with agents that inhibit or prohibit bone ingrowth. Such surfaces may include impermeable and other materials such as one or more of those listed in Table 1.

Drug Delivery

One or more surfaces of the apparatus may be coated with agents that may elute therapeutic substances such as drugs.

Complications

The apparatus and methods may include means to address complications that may be associated with bone implants. One such complication is infection. The apparatus and methods may include features that counteract infection. For example, such a feature may include a coating. The coating may include antibiotics such as tobramycin or other effective antimicrobials. Another such feature may be the delivery of heat to raise the apparatus temperature sufficiently high to kill bacteria and other undesirable tissues on or near the implant.

Installation

The following is one illustrative method of installation of the apparatus in a bone that has a fracture. The procedure may be completed either in an inpatient or an outpatient setting.

1. Provisionally reduce the fracture using standard techniques
2. Access the intramedullary cavity in a location that causes minimal tissue damage to the patient and sufficient access for the physician; proximal or distal.
3. Introduce a delivery catheter into the bone near the area of the fracture. Position can be confirmed on fluoroscopy.
4. Deploy the structural support. A positioning aid, which may be a central axis member, may be used. External manipulation may be applied.
5. Reposition the fractured bone into its ideal healing location. The positioning aid may then be locked into the wall of the intramedullary cavity by deploying the anchoring mechanism.
6. Deploy an anchor tensioning element (such as an anchoring substrate) into the space inside the structural support and near the location of the fracture.
7. Deploy anchors in the fracture fragments, either externally or internally, depending on accessibility. The anchors are driven through both the fragments and the anchoring substrate.
8. Confirm location of the fragments via x-ray, fluoro, or direct visualization. Apply tension as needed to position the fracture in the desired position with adequate pressure on the fragment surfaces to stabilize the fracture for healing.
9. Lock the apparatus in place.
10. Disengage delivery instruments from the apparatus. Remove the delivery instruments from the patient, and close patient.

Numerous other steps may be involved and many different sequences of steps may be practiced without departing from the principles of the invention.

Materials

The apparatus and portions thereof may include any suitable materials. Table 1 lists illustrative materials that may be included in the apparatus and portions thereof.

TABLE 1

| Materials | | |
|---|---|---|
| Category | Type | Material |
| Metals | Nickel titanium alloys | Nitinol |
| | Stainless steel alloys | 304 |
| | | 316L |
| | | BioDur ® 108 Alloy |
| | | Pyromet Alloy ® CTX-909 |
| | | Pyromet ® Alloy CTX-3 |
| | | Pyromet ® Alloy 31 |
| | | Pyromet ® Alloy CTX-1 |
| | | 21Cr—6Ni—9Mn Stainless |
| | | 21Cr—6Ni—9Mn Stainless |
| | | Pyromet Alloy 350 |
| | | 18Cr—2Ni—12Mn Stainless |
| | | Custom 630 (17Cr-4Ni) Stainless |
| | | Custom 465 ® Stainless |
| | | Custom 455 ® Stainless Custom |
| | | 450 ® Stainless |
| | | Carpenter 13-8 Stainless |
| | | Type 440C Stainless |
| | Cobalt chromium alloys | MP35N |
| | | Elgiloy |
| | | L605 |
| | | Biodur ® Carpenter CCM alloy |
| | Titanium and titanium alloys | Ti—6Al—4V/ELI |
| | | Ti—6Al—7Nb |
| | | Ti—15Mo |
| | Tantalum | |
| | Tungsten and tungsten alloys | |
| | Pure Platinum | |
| | Platinum-Iridium alloys | |
| | Platinum-Nickel alloys | |
| | Niobium | |
| | Iridium | |
| | Conichrome | |
| | Gold and Gold alloys | |
| Absorbable metals | | Pure Iron |
| | | magnesium alloys |
| Polymers | | Polyetheretherketone (PEEK) |
| | | polycarbonate |
| | | polyolefin's |
| | | polyethylene's |
| | | polyether block amides (PEBAX) |
| | | nylon 6 |
| | | 6-6 |
| | | 12 |
| | | Polypropylene |
| | | polyesters |
| | | polyurethanes |
| | | polytetrafluoroethylene (PTFE) |
| | | Poly(phenylene sulfide) (PPS) |
| | | poly(butylene terephthalate) PBT |
| | | polysulfone |
| | | polyamide |
| | | polyimide |
| | | poly(p-phenylene oxide) PPO |
| | | acrylonitrile butadiene styrene (ABS) |
| | | Polystyrene |

TABLE 1-continued

Materials

| Category | Type | Material |
|---|---|---|
| Membrane materials | | Poly(methyl methacrylate) (PMMA) |
| | | Polyoxymethylene (POM) |
| | | Ethylene vinyl acetate |
| | | Styrene acrylonitrile resin |
| | | Polybutylene |
| | | Silicone |
| | | Polyether block amides (PEBAX) |
| | | Polyurethanes |
| | | Silicone polyurethane copolymers |
| | | Nylon |
| | | Polyethylene terephthalate (PET) |
| | | Goretex ePTFE |
| | | Kevlar |
| | | Spectra |
| | | Dyneena |
| | | Polyvinyl chrloride (PVC) |
| Absorbable polymers | | Poly(glycolic acid) (PGA) |
| | | Polylactide (PLA), |
| | | Poly(ε-caprolactone), |
| | | Poly(dioxanone) |
| | | Poly(lactide-co-glycolide) |
| Radiopaque materials | | Barium sulfate |
| | | Bismuth subcarbonate |
| Biomaterials | Collagen | Bovine, porcine, ovine, amnion membrane |
| Bone growth factors | | Demineralized bone matrix |
| | | Bone morphogenic proteins (BMP) |
| | | Calcium phosphate |
| | | Heat-treated hydroxylapapatite |
| | | Basic fibroblast growth factor (bFGF)-coated hydroxyapaptite |
| | | Hydroxyapaptite/tricalcium phosphate (HA/TCP |
| Anti-microbial Coatings | | |

The apparatus may be provided as a kit that may include one or more of a structural support, an anchoring substrate, a central axis member, an anchor, a delivery instrument and associated items.

Apparatus and methods in accordance with the invention will now be described in connection with the FIGS. The FIGS. show illustrative features of apparatus and methods in accordance with the principles of the invention. The features are illustrated in the context of selected embodiments. It will be understood that features shown in connection with one of the embodiments may be practiced in accordance with the principles of the invention along with features shown in connection with another of the embodiments.

Apparatus and methods described herein are illustrative. Apparatus and methods of the invention may involve some or all of the features of the illustrative apparatus and/or some or all of the steps of the illustrative methods. The steps of the methods may be performed in an order other than the order shown and described herein. Some embodiments may omit steps shown and described in connection with the illustrative methods. Some embodiments may include steps that are not shown and described in connection with the illustrative methods.

Illustrative embodiments will now be described with reference to the accompanying drawings, which form a part hereof.

The apparatus and methods of the invention will be described in connection with embodiments and features of an illustrative bone repair device and associated hardware and instrumentation. The device and associated hardware and instruments will be described now with reference to the FIGS. It is to be understood that other embodiments may be utilized and structural, functional and procedural modifications may be made without departing from the scope and spirit of the present invention.

FIG. 1 shows illustrative device 100 implanted in bone B, which is illustrated as a radius. Bone B includes bone portions $P_B$, $P_h$ and $P_a$ in distal end D. Bone segment PB is the largest portion of bone B. Bone segment Ph is a head portion. Bone segments $P_h$ and $P_a$ include articular surface AS. Bone portions $P_B$, $P_h$ and $P_a$ are separated or partially separated along fractures $F_a$ and $F_h$. Fracture $F_a$ transects articular surface AS. Fracture $F_h$ transects head H.

It will be appreciated that bone portions $P_B$, $P_h$ and $P_a$ define an illustrative fracture in bone B. Device 100 may be used to treat fractures that have a greater or lesser number of bone portions. The bone portions may have different shapes, orientations and sizes from those shown in FIG. 1. It will be appreciated also that the fracture shown in FIG. 1 is illustrated as a fracture near the end of a long bone, but device 100 may be used to treat fractures in other portions of long bones, such as the midshaft, and in bones that may be identified as being other than long bones, e.g., vertebrae.

Device 100 is elongated along its longitudinal axis $L_D$ (in which D indicates device). Device 100 is in intramedullary space IS of bone B. Distal end 102 of device 100 is in epiphyseal region E of bone B. Proximal end 104 is in or adjacent diaphyseal region D of bone B. Portions of device 100 that are between distal end 102 and proximal end 104 are in metaphyseal region M of bone B.

Device 100 may include structural cage 105. Structural cage 105 may include support members 106. Support members 106 may extend from cage base 108 to distal hub 110. (The direction extending from cage base 108 will be referred to as the "distal direction." The opposite direction will be referred to as the "proximal direction." "Distal," relative to "proximal," generally means the leading end of apparatus that is inserted, or is to be inserted, in the body.) The distance along axis LD between cage base 108 and distal hub 110 may be adjusted to change the shape of support members 106.

When cage base 108 is maximally spaced apart from distal hub 110, structural cage 105 is in a compressed state. When cage base 108 and distal hub 110 are pushed or drawn together, structural members 106 are deflected radially outward along radial direction $R_D$ (in which "D" indicates device). In this way, structural cage 105 may expand. Device 100 is shown in an expanded state. In some embodiments, structural members 106 and anchor substrate 124 may self-expand radially. This may draw base 108 and distal hub 110 together longitudinally.

Structural cage 105 may be used to provide support to bone portions $P_B$, $P_a$ and $P_h$. The support may include aligning and stabilizing bone segments $P_B$, $P_a$ and $P_h$ during reduction and/or healing. The support may be subchondral support. Structural cage 105 may be used to provide load resistance to bone B during healing.

Device 100 may include anchoring substrate 112. Substrate 112 may be engaged by anchors such as 114 and 116. Anchor 114 fastens bone segment Ph to substrate 112. Anchor 116 fastens bone segment Pa to substrate 112. The anchors may engage substrate 112 in a wide range of positions. The anchors may engage substrate 112 from a wide range of angles. Each of the anchors may apply a force to its respective bone portion. The force may be oriented to appropriately position the bone portions for healing. The force may be directed at least in part toward axis LD. The force may be considered an inward force (at least partially in direction $-R_D$). Structural cage 105 may apply to the bone portions a force that is directed at least in part away from axis $L_D$. The force from structural cage 105 may be considered an outward force (at least partially in direction $R_D$).

Anchors 114 and 116 are illustrated as threaded screws, but any suitable anchors may be used.

The anchors, anchoring substrate and support structural cage may thus be used in concert to select for each bone portion one or more of a desired position, orientation and force. One or both of the position and orientation may be selected by appropriate selection of anchor size, anchor position, anchor tension, structural cage size, and support member configuration and position. Because the position and orientation may be selected, the bone portions may be appropriately aligned relative to each other.

Device 100 may include stem 128. Stem 128 may extend in the proximal direction from cage base 108. Stem 128 may include stem anchoring substrate 118 and proximal base 120. Stem anchoring substrate 118 may support proximal base 120. Anchor 122 may fasten stem 128 to bone B portion $P_B$. Anchor 122 may be engaged such that it applies longitudinal and/or rotational forces to device 100. Anchor 122 may be engaged such that it applies a radial force to device 100. The radial force may induce or counteract bending of device 100 along axis $L_D$. Anchor 122 may apply a resistive longitudinal force to device 100. The resistive longitudinal force may resist forces applied to device 100 by distal anchors 114 and 116.

Proximal base 120 may support device retention feature 122. Device retention member 126 may be used to engage device 100 for insertion and manipulation. A device manipulator (not shown) may be used in conjunction with device retention member 126 to draw device 100 in the proximal direction.

Device may include illustrative central member hub 130. Central member hub 130 may be used to recapture and remove device 100 after deployment.

Drawing device 100 in the proximal direction may adjust forces (tensile, compressive or both) between bone portions $P_a$, $P_h$ and $P_B$. Drawing device 100 in the proximal direction may adjust the orientation and position of bone portions $P_a$ with respect to $P_B$. In some embodiments, anchor 122 may be used to retain the compressive forces after device 100 is drawn in the proximal direction.

Device 100 may include central axis member 124. Central axis member 124 may extend from distal hub 110, through cage base 108 and through proximal base 120 into intramedullary space IS of bone B. Central axis member 124 may be used to effect expansion of structural cage 105. Some embodiments may not include central axis member 124. (In some embodiments, anchoring substrate 112 may be drawn proximally relative to structural cage 105 to adjust the tension while maintaining the position and support of the bone segments.)

In some embodiments, central axis member 124 may be used to expand structural cage 105 by applying tension between hub 100 and cage base 108 and/or 120. In some embodiments, this may be done by applying simultaneously a proximally directed force to central axis member 124 and a distally directed force to cage base 108. In some embodiments, central axis member may be rotatably connected to hub 110 and threaded through cage base 108. In those embodiments, structural cage 105 may be expanded by rotating central axis member 124. In some embodiments, structural cage 105 may be self-expanding.

The final expanded shape may be designed into the structure of structural cage 105. The final expanded shape may be limited by the space available in the cavity. The expansion may be elastic and may be based on a spring material that returns to a predetermined shape.

Device 100 in its compressed state may be delivered into the body through a small access incision along the mid shaft section bone (D, in FIG. 1) in an area where soft tissue disruption can be minimized.

Figure 1A:
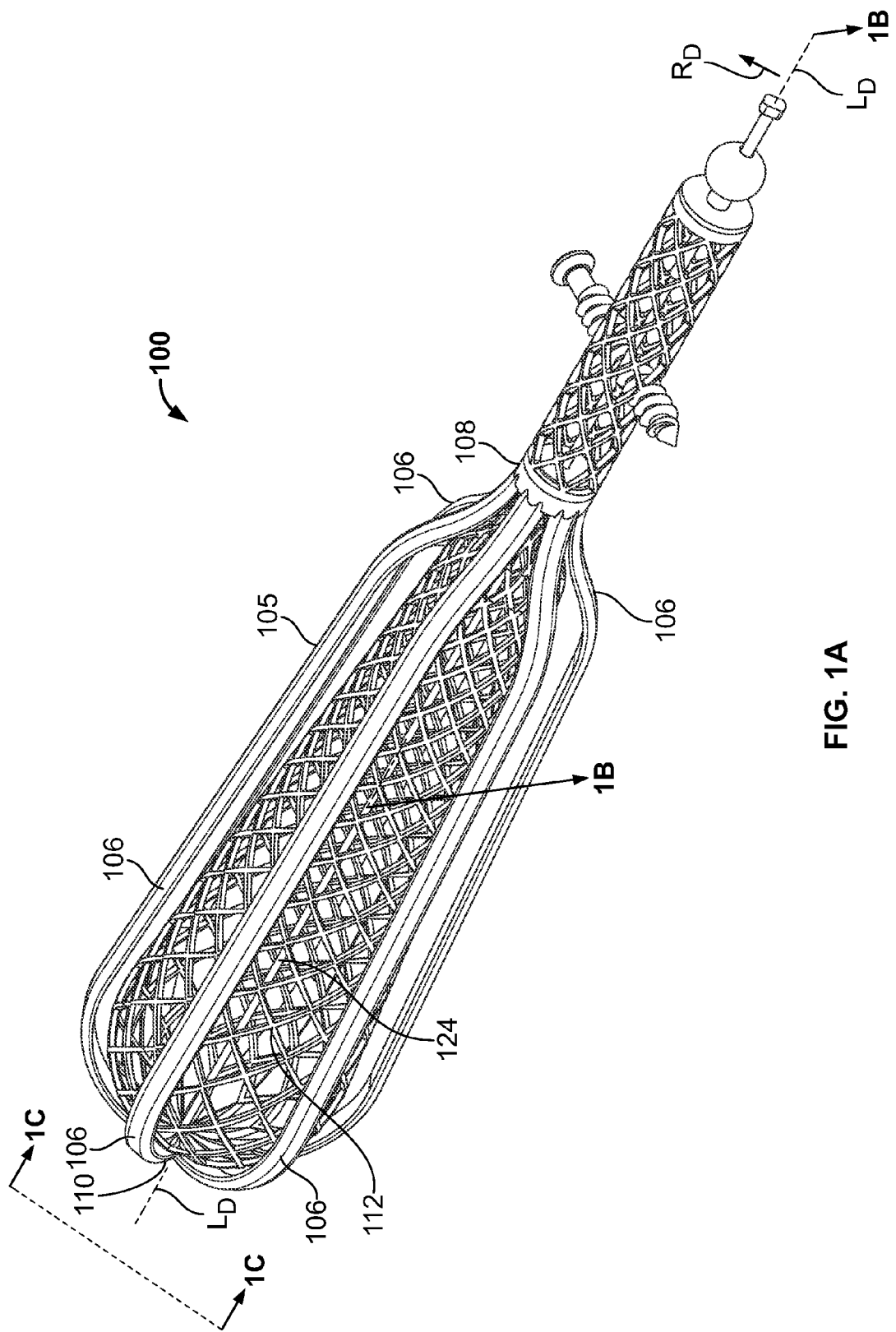
FIG. 1A is a perspective view of the apparatus shown in FIG. 1.

FIG. 1A shows device 100 in isometric view. Structural cage 105 includes support members 106. Support members 106 may expand or contract along direction $R_D$ based on relative positioning of cage base 108 and hub 110 along device axis $L_D$. Support cage 105 may be contracted for introduction into intramedullary space IS.

Support cage 105 is illustrated as having six support members 106. It will be appreciated that any suitable numbers of support members may be used. for example, support cage 105 may have a number of support members 106 in the range of 2-40 or more than 40.

Support members 106 are illustrated as having a rectangular cross-sectional shape. It will be appreciated that support members 106 may have any suitable cross-sectional shape. For example, the cross-sectional shape may be round, square, braided, stranded or profiled. Support cage 105 may include support members that have different cross-sectional shapes, dimensions or material properties. When support members have different shapes, dimensions or material properties, support cage 105 may undergo non-radial deformation. Such deformation may be helpful for conforming device 100 to the inside of bone B (including bone segments $P_a$, $P_h$ and $P_B$).

Support members 106 are illustrated as being joined at cage base 108 and hub 110. The ends of the members are shown joined at both ends. In some embodiments, support members 106 may have one or more free or partially free ends.

Support members 106 may be cut of a single tube or could be made independently and then joined.

Anchoring substrate 112 is present inside structural cage 105. Anchoring substrate 112 may have a collapsed state and an expanded state. The collapsed state may be used for delivery. The expanded state may be used for deployment and fracture repair.

In some embodiments, anchoring substrate 112 may include a laser-cut structure. Anchoring substrate 112 may be constructed so as to engage with an anchor such as 114 (shown in FIG. 1) and hold the anchor under a mechanical load. In some embodiments, anchoring substrate 112 may be affixed to support cage 105. Anchoring substrate 112 may be affixed to one or more of hub 110, one or more portions of support members 106, central axis member 124, cage base 108 and proximal base 120.

In some embodiments, anchoring substrate 112 may not be affixed to device 100 (although it may be retained by support cage 105). Such lack of attachment may facilitate adjustment of the tension and loading of bone segments.

Figure 1B:
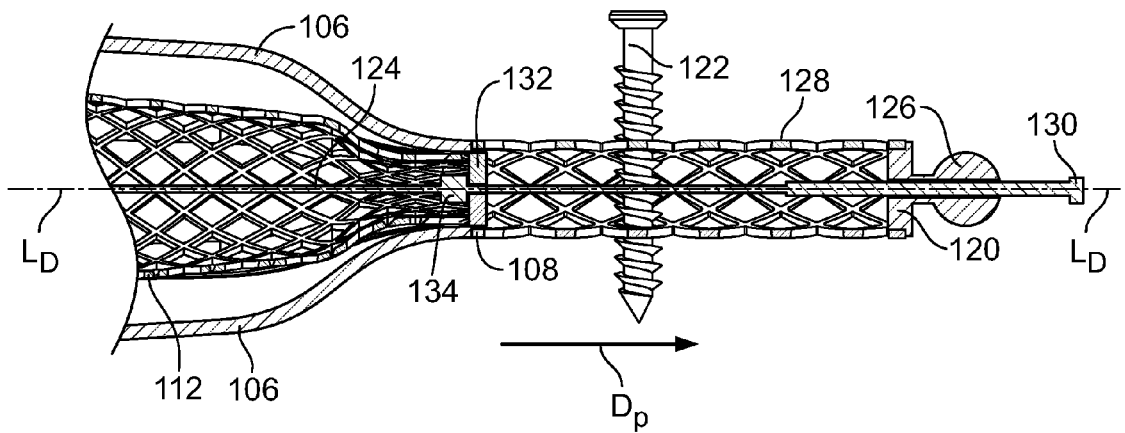
FIG. 1B is a partial sectional view of the apparatus shown in FIG. 1A.

FIG. 1B is a cross-sectional view taken along lines 1B-1B (shown in FIG. 1A). FIG. 1B shows central axis member 124 running from hub 110 (not shown) through anchoring substrate base 132 (which is concentrically within cage base 108), stem 128, proximal base 120 and device retention member 126.

Central member hub 130 protrudes proximally from device retention member 126. Central member hub 130 may be configured to be engaged to adjust or control tension and or rotation of central member 124. Manipulation of central member hub 130 may facilitate delivery and expansion of structural cage 105, and or anchor substrate 112. Central member hub 130 may maintain tension between distal and proximal ends of structural cage 105 or anchoring substrate 112.

Device retention member 126 may be used to in connection with delivery, manipulation and or removal of device 100.

Stop 134 on central axis member 124 may be drawn in proximal direction $D_P$ by pulling central member hub 130 in direction $D_P$ relative to stem 128. In some embodiments, this may be accomplished by pushing device retention member 126 distally ($-D_P$) while pulling central member hub 130 proximally. The pushing and pulling may be accomplished using apparatus and methods shown and described herein or known grasping device instruments.

Stop 134 will urge anchoring substrate base 108 in direction $D_P$. Anchoring substrate base 108 will then draw anchoring substrate 112 in direction $D_P$. Motion of anchoring substrate 112 in direction DP will apply force to anchors 114 and 116. The force may have a distal component and a radially inward ($-R_D$) component. The force may thus compress bone segments Pa and Ph against bone segment $P_B$ (shown in FIG. 1).

Stop 134 may transfer longitudinal force from device retention member 126 in a proximal direction to anchor substrate 112 through the coupling mechanism between device retention member 126, proximal base 120 and central member hub 130. Alternatively central axis member 124 may be coupled mechanically to cage base 108 by a ratchet, screw or other suitable mechanism.

Figure 1C:
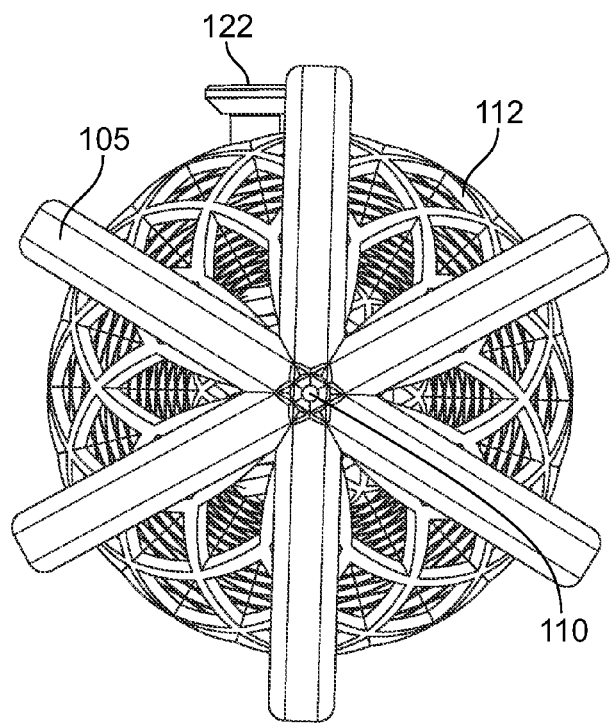
FIG. 1C is front view of the apparatus shown in FIG. 1A in accordance with the principles of the invention.

FIG. 1C shows a view taken along lines 1C-1C (shown in FIG. 1A). FIG. 1C shows expanded support cage 105 (including hub 110) and expanded anchoring substrate 112. Locking anchor 122 is also shown.

One or more of the surfaces or elements of device 100 may include a coating. The coating may include an agent. The agent may provide a bone growth promotion agent, a bone growth inhibition or prohibition agent, a drug eluting agent or any other suitable agent.

Figures 2, 3:
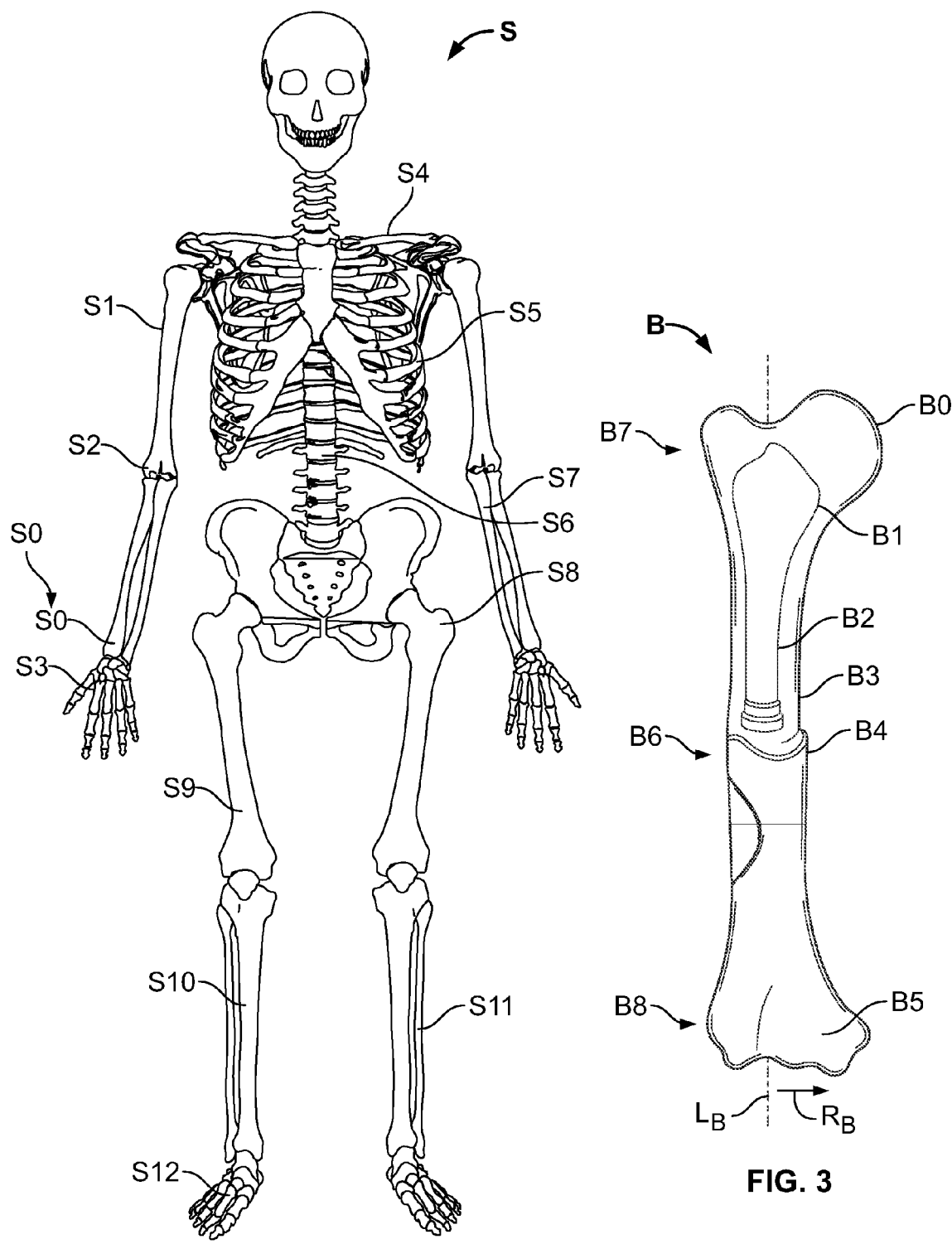
FIG. 2 is a front view of an illustrative human skeleton.
FIG. 3 is a partial sectional view of a fractured bone.

FIG. 2 shows illustrative skeleton S. Skeleton S includes illustrative bones $S_i$ in which device 100 (shown in FIG. 1) may be used as shown and described in connection with bone B (shown in FIG. 1). Table 2 includes a partial list of bones $S_i$.

TABLE 2

Bones $S_i$.

| Bone | Reference numeral in FIG. 2 |
|---|---|
| Distal Radius | $S_0$ |
| Humerus | $S_1$ |
| Proximal Radius and Ulna (Elbow) | $S_2$ |
| Metacarpals | $S_3$ |
| Clavicle | $S_4$ |
| Ribs | $S_5$ |
| Vertebrae | $S_6$ |
| Ulna | $S_7$ |
| Hip | $S_8$ |
| Femur | $S_9$ |
| Tibia | $S_{10}$ |
| Fibula | $S_{11}$ |
| Metatarsals | $S_{12}$ |

FIG. 3 schematically shows anatomy of bone B (shown in FIG. 1). Anatomical features of bone B are listed in Table 3. Apparatus and methods in accordance with the principles of the invention may involve one or more of the anatomical features shown in Table 3. Features of bone B may be described in reference to bone axis $L_B$ (in which B indicates bone) and radius $R_B$ (in which B indicates bone).

TABLE 3

Anatomical features of some of the bone types that may be treated by the apparatus and methods.

| Anatomical feature | Reference numeral in FIG. 3 |
|---|---|
| Articular surface | $B_0$ |
| Cancellous, spongy or trabecular bone | $B_1$ |
| Medullary cavity | $B_2$ |
| Cortical or dense bone | $B_3$ |
| Periosteum | $B_4$ |
| Proximal articular surface | $B_5$ |
| Diaphysis or midshaft | $B_6$ |
| Metaphysis or end region | $B_7$ |
| Epiphysis | $B_8$ |
| Articular surface | $B_9$ |

The terms "end-bone" and "end-bone fracture" may be used to refer to fractures that occur in the epiphyseal or metaphyseal region of long bones. Such fractures include peri-articular and intra-articular fractures.

Figure 4:
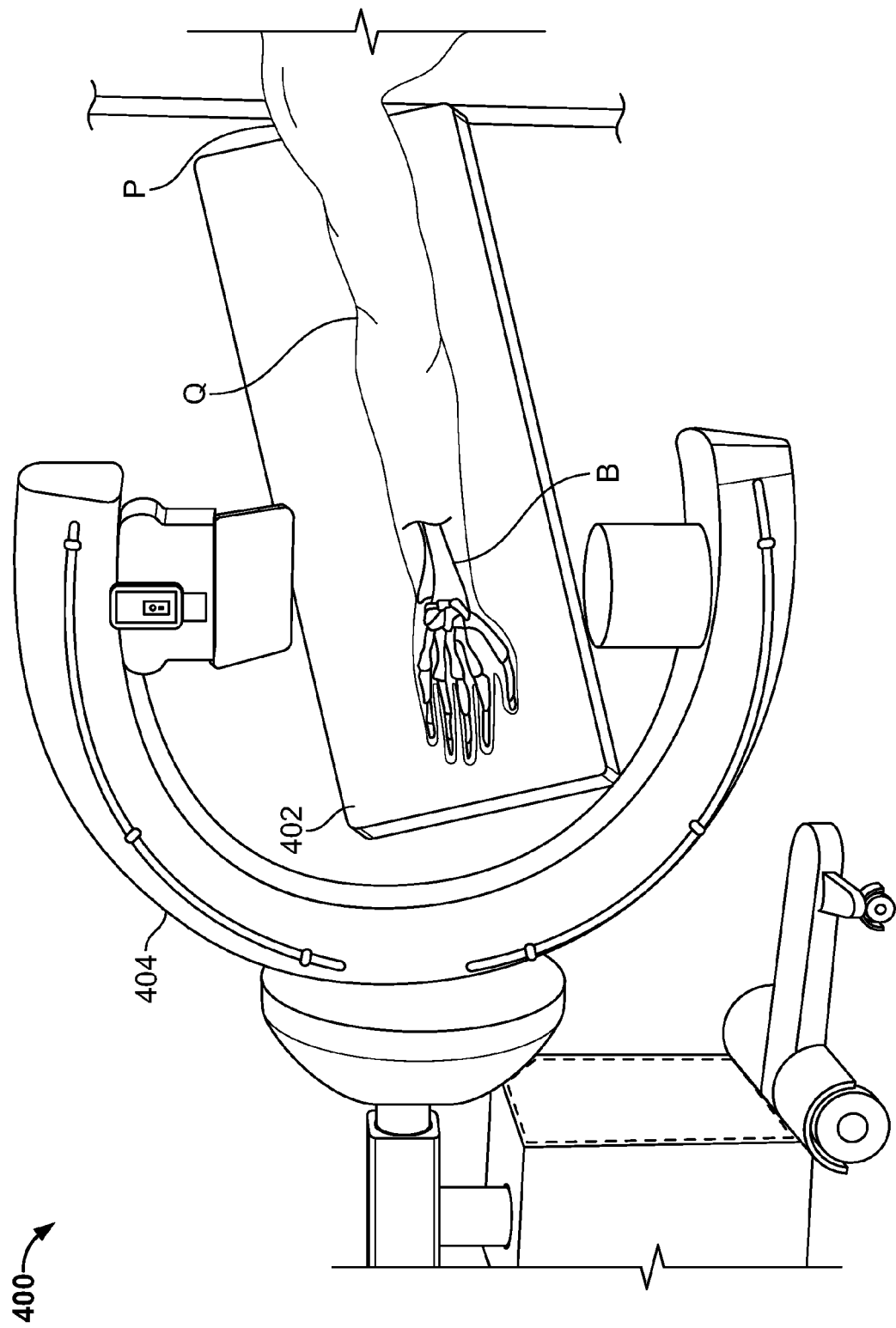
FIG. 4 is a perspective view showing a body portion that may be treated using the apparatus shown in FIG. 1.

FIG. 4 shows portion 400 of an illustrative surgical environment in which a fracture in bone B may be diagnosed and treated. Patient P may be sedated appropriately. A limb nerve block may be administered. A pressure cuff may be used to maintain limb Q in a relatively blood-free state. Limb Q may be supported by procedure table 402 and any other appropriate supports to manage the position of bone B during surgery. Environment 400 may include imaging system 404.

Figure 5:
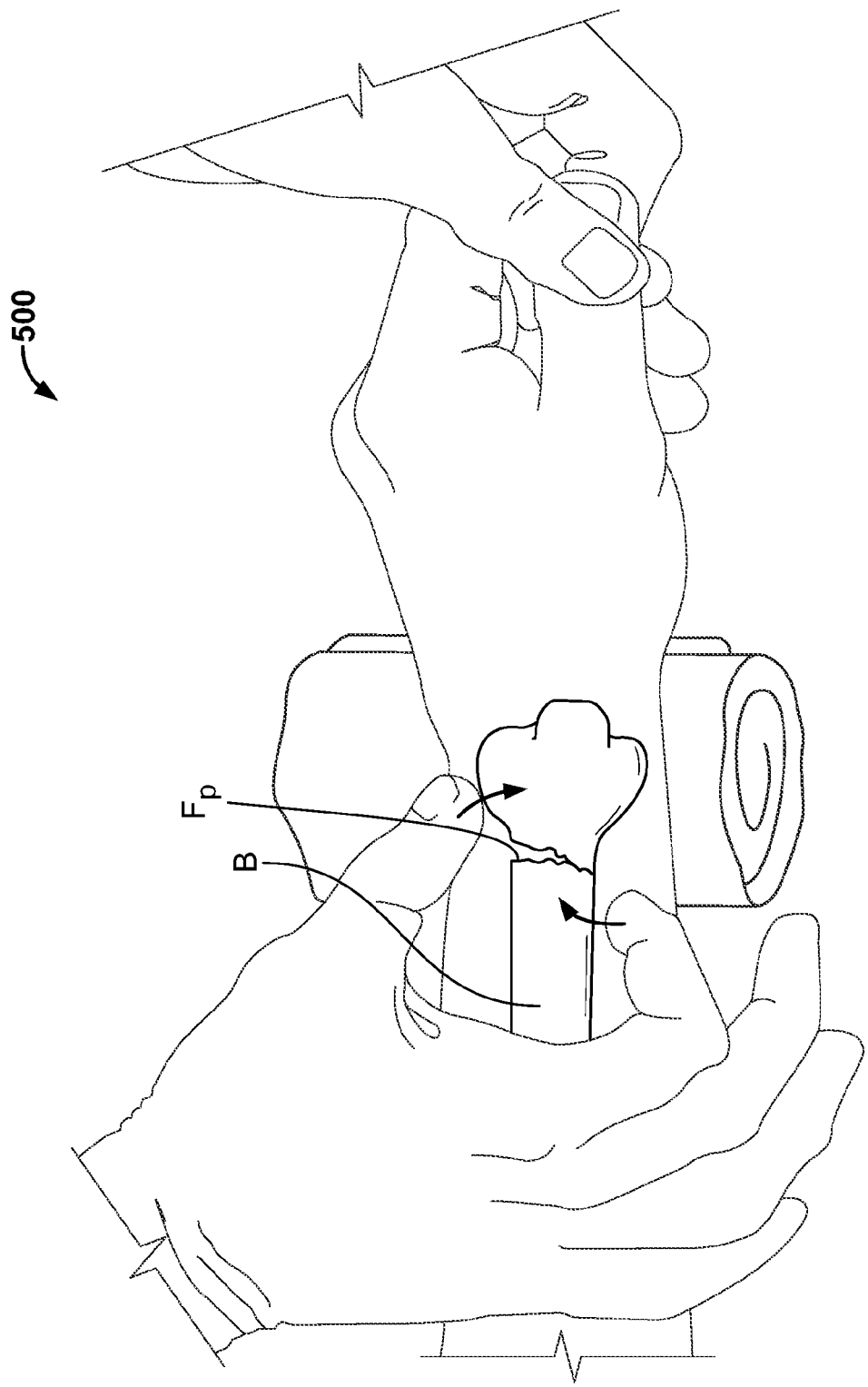
FIG. 5 is a perspective view showing the a portion of the body portion shown in FIG. 4.

FIG. 5 shows illustrative therapeutic scenario 500. In scenario 500, manual traction techniques are applied to reestablish anatomic reduction in fracture $F_p$ in bone B.

Provisional or temporary reduction is often undertaken in fracture repair to restore bone segments to their normal positions before they are anchored.

When the number of bone segments is small and/or the dislocation of the bone segments is modest, closed reduction techniques may be employed. Closed reduction does not include incisions and utilizes manual traction by one or more physicians. The physicians will utilize different tension, compression, and bending motions to reestablishing normal bone segment positioning. A physician or assistant may maintain the normal bone segment positions during an implant procedure.

For more displaced fracture patterns, a limited open reduction can be utilized. K-Wires, external probes, and special clamps can be employed for the provisional reduction. Small incisions can be made allowing the probes and clamps to aid in repositioning the fracture segments. Once the bone segments are in position k-wires can be utilized to maintain the reduction. K-Wires are approximately 1-2 mm in diameter metallic wires that can be driven across fracture lines to provide temporary support. The k-wires may be positioned and then removed strategically to facilitate the procedure in a way that reduces interference with bone cavity preparation or implant deployment.

Figure 6:
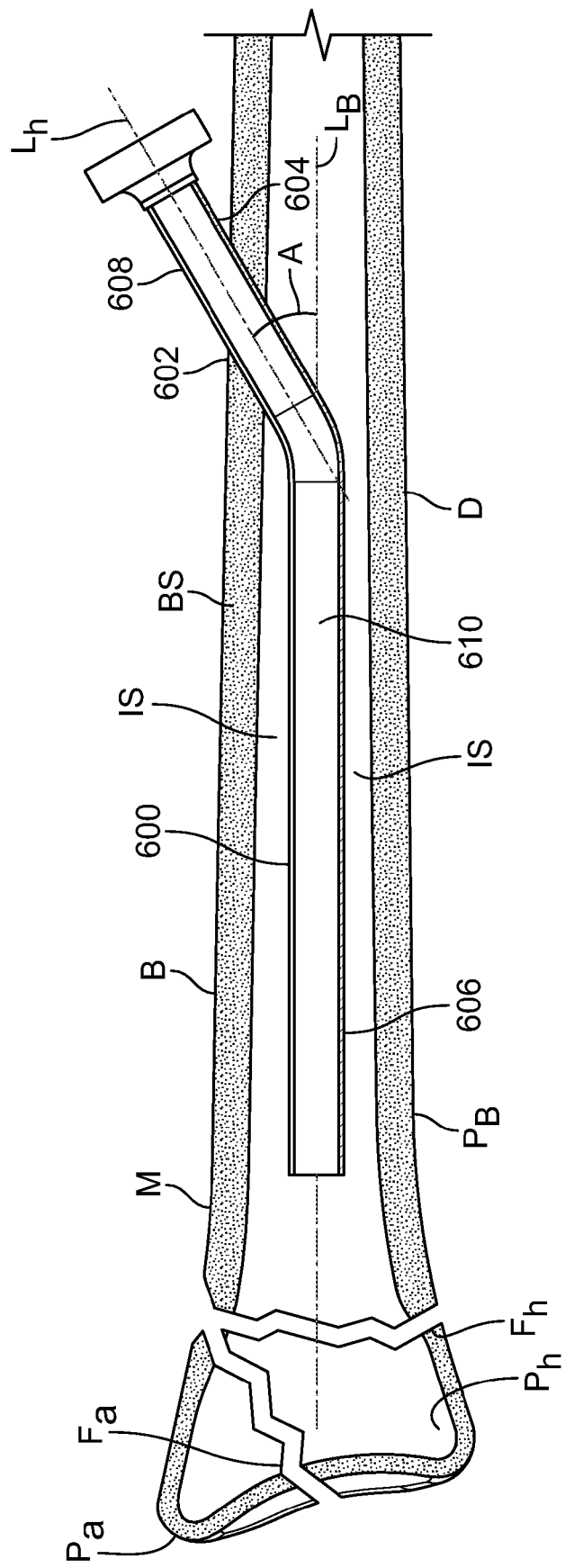
FIG. 6 is a sectional view of apparatus in accordance with the principles of the invention.

FIG. 6 shows illustrative sheath 600. Hollow sheath 600 is shown entering intramedullary space IS of bone B. Sheath 600 may include lumen 610. Lumen 610 may provide access to intramedullary space IS. Sheath 600 enters intramedullary space IS at position 602. Position 602 may be in diaphyseal section D of bone B. Position 602 may be selected to minimize soft tissue damage. Near position 602, a small incision may be made in the soft tissue (not shown). The tissue may be displaced to reveal bone surface BS.

A standard orthopaedic drill instrument may be used to create access hole 604 in bone B. Axis hole 604 may be drilled along axis $L_h$. Axis $L_h$ may form an angle A with bone axis $L_B$. Angle A may be an acute angle.

Hole 604 may be similar to commonly drilled bone access holes. Hole 604 may be sufficiently small that hole 604 does not cause stress risers at position 602. Distal end 606 of sheath 600 may be advanced, through intramedullary canal IC, into metaphyseal region M of bone B. Proximal end 608 of sheath 600 may be positioned in hole 604. Distal end 606 may be disposed in any portion of intramedullary space IS, such as in the end-bone.

Sheath 600 may be a thin-walled flexible cannula. Sheath 600 may be similar to the cannulas that are commonly used in minimally invasive or percutaneous interventional procedures elsewhere in the body. Sheath 600 may be made of rigid metal that is shaped to promote access to intramedullary space IS.

Figure 7:
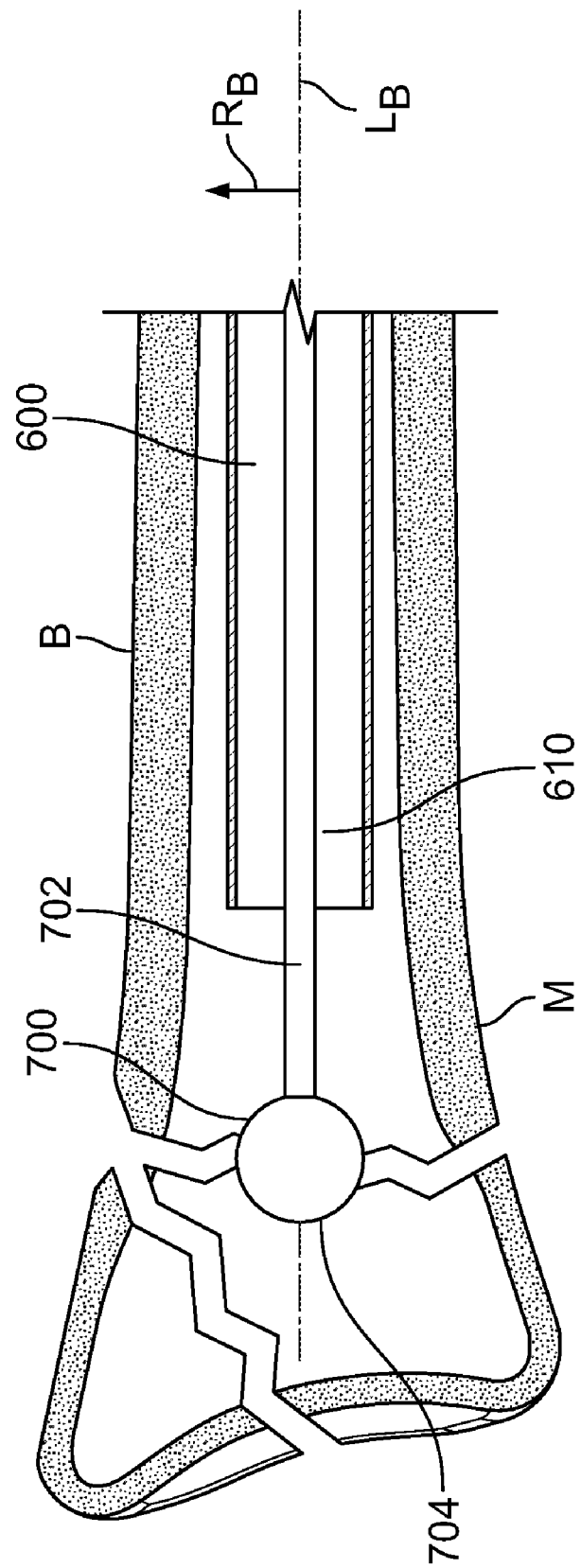
FIG. 7 is a sectional view of apparatus shown in FIG. 6 along with additional apparatus in accordance with the principles of the invention.

FIG. 7 shows illustrative intramedullary space reamer 700. Reamer 700 may be expandable and contractible. Reamer 700 may in a contracted state be inserted in proximal end 608 of sheath 600 (shown in FIG. 6). Reamer shaft 702 may be used to advance reamer 700 through lumen 610 into metaphyseal region M of bone B. Reamer 700 may have suitable features at or about surface 704 for removing undesirable tissue, such as cancellous bone, from the end-bone. Reamer shaft 702 may rotate reamer surface 704 about, and translate it along, bone axis L as appropriate to prepare the end-bone for further treatment.

In some embodiments, the use of reamer 700 may be consistent with procedures that are used in the implantation of intramedullary nails. Such procedures include the application of one or more of ultrasonic energy, vibration, RF energy, pressure, rotation, water jetting, suction and other suitable mechanisms to remove the undesirable tissue. In some embodiments, reamer 700 may have one or more of the following features: expansion, fixed size (non-expanding), unidirectional reaming, multi-directional reaming, rigid reamer shaft 702, flexible reamer shaft 702 and steerability.

Figure 8:
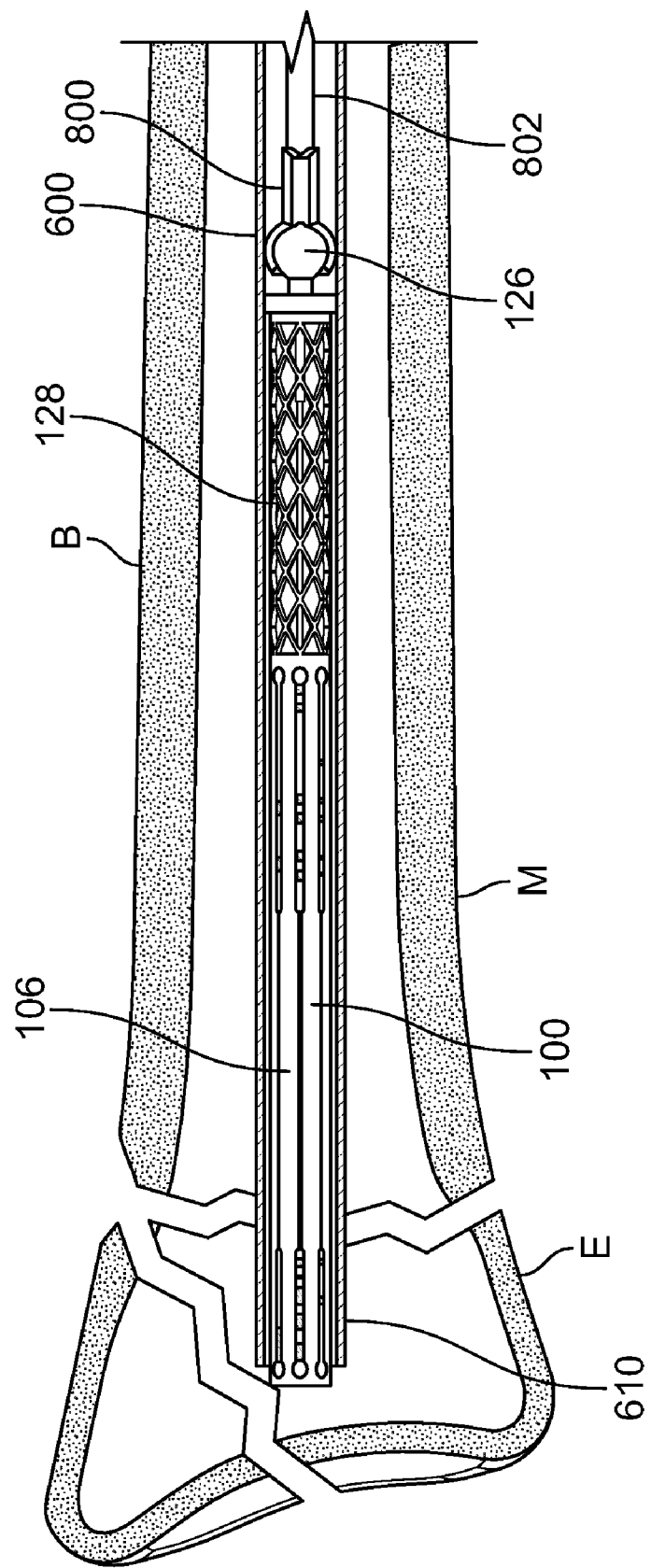
FIG. 8 is a sectional view of apparatus shown in FIG. 1 along with additional apparatus in accordance with the principles of the invention.

FIG. 8 shows a stage in the delivery of device 100 to end-bone of bone B. In FIG. 8, device delivery apparatus 800 is engaged with device retention element 126 at the proximal end of device 100. Shaft 802 may control positioning and rotation of device delivery apparatus 800. Delivery apparatus 800 may include a keyed grasper for engagement and disengagement of portions of device 100 (shown in FIG. 1). Device 100 is in a compressed state. Device 100 is positioned within lumen 610 of sheath 600. Distal hub 110 of device 100 is in epiphyseal region E of bone B. Support members 106 and stem 128 are also shown within lumen 610.

Figure 9:
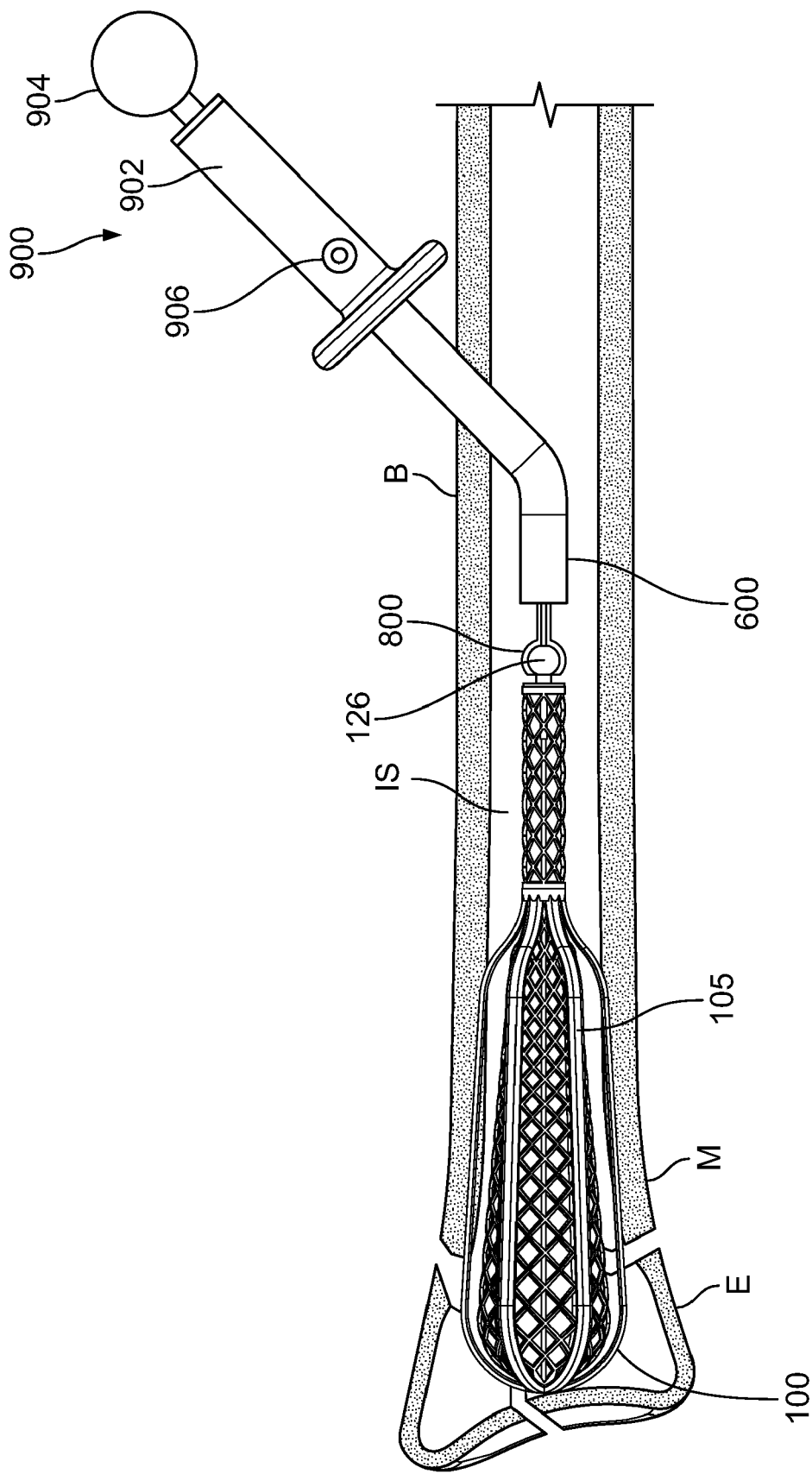
FIG. 9 is a partial sectional view of apparatus shown in FIG. 1 along with additional apparatus in accordance with principles of the invention.

FIG. 9 shows a subsequent step in the delivery of device 100 to the end-bone of bone B. In FIG. 9, device delivery apparatus 800 has moved device 100 distally out of sheath 600. Structural cage 105 has been expanded in the end-bone. In the example illustrated, the end-bone spans from the bone segments to midshaft D of bone B intramedullary space IS.

FIG. 9 also shows proximal delivery apparatus controller 900. Controller 900 may include handle 902, trigger mechanism 904 and set screw 906. Handle 902 may be used to apply, via shaft 802, the forces that are necessary to position and expand device 100. Trigger mechanism 904 may be used to engage or disengage device retention member 126.

Figure 10:
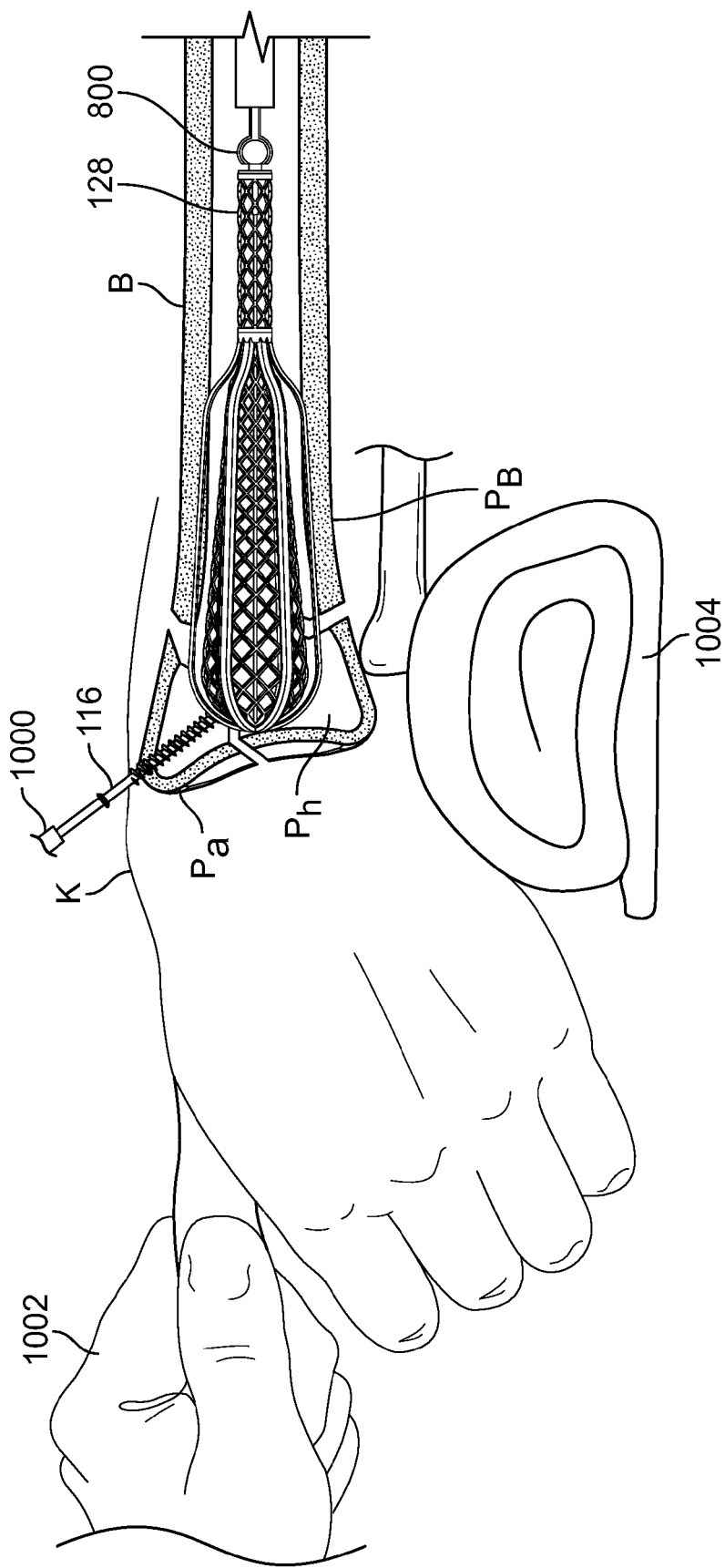
FIG. 10 is a partial sectional view showing the use of the apparatus shown in FIG. 1 along with additional apparatus in accordance with the principles and methods of the invention.

FIG. 10 shows the fastening of bone segment $P_a$ to anchoring substrate 112. A small incision may be made in skin K in an optimal location. Then, a small pilot hole may be made in the bone segment $P_a$. Provisional reduction may be maintained by assistant's hand 1002, tong/clamp type instruments, k-wires or other known methods. Support 1004 may be provided to position bone segments $P_a$, $P_h$ and $P_B$ for the insertion of anchor 116. Then, instrument 1000 may be used to drive anchor 116 through bone segment $P_a$. Instrument 1000 may be a screwdriver or other suitable instrument.

Figure 11:
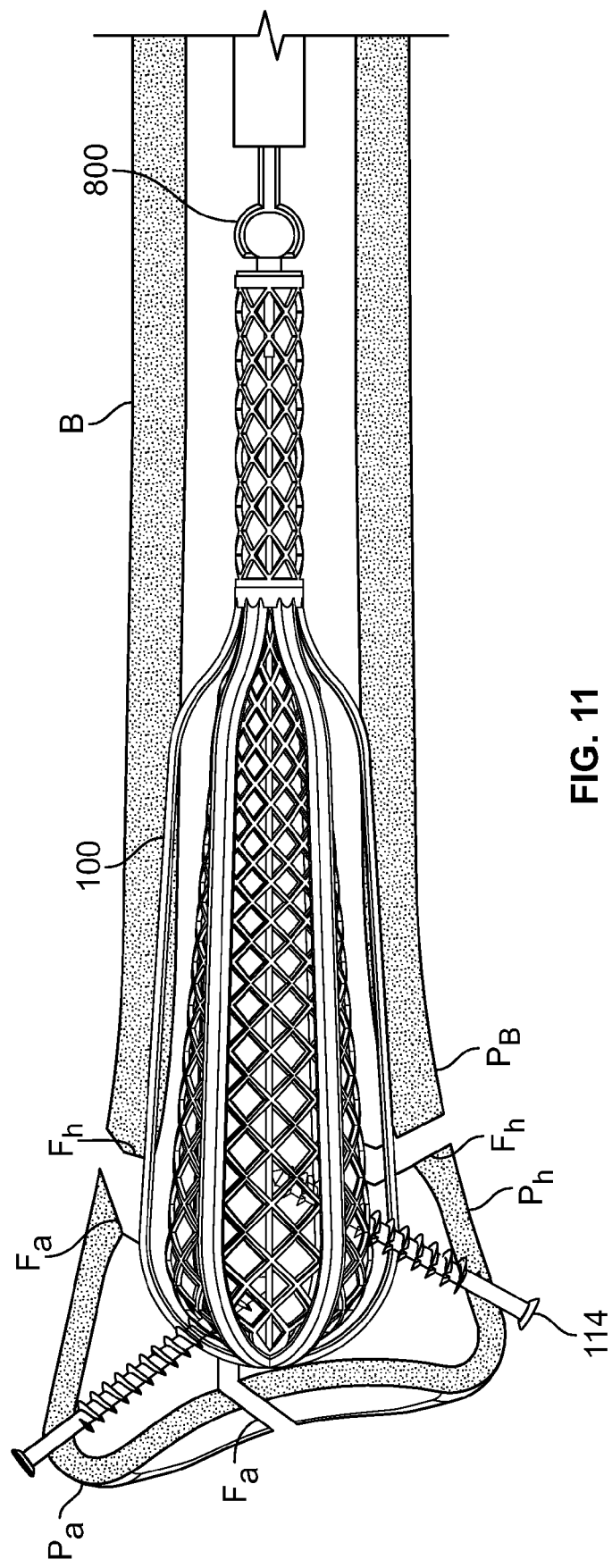
FIG. 11 is a partial sectional view of the apparatus shown in FIG. 1 along with additional apparatus in accordance with the principles of the invention.

FIG. 11 shows anchor 114 fastening bone segment Ph to anchoring substrate 112. Device 100 may be stabilized in bone B using device delivery apparatus 800.

Figure 12:
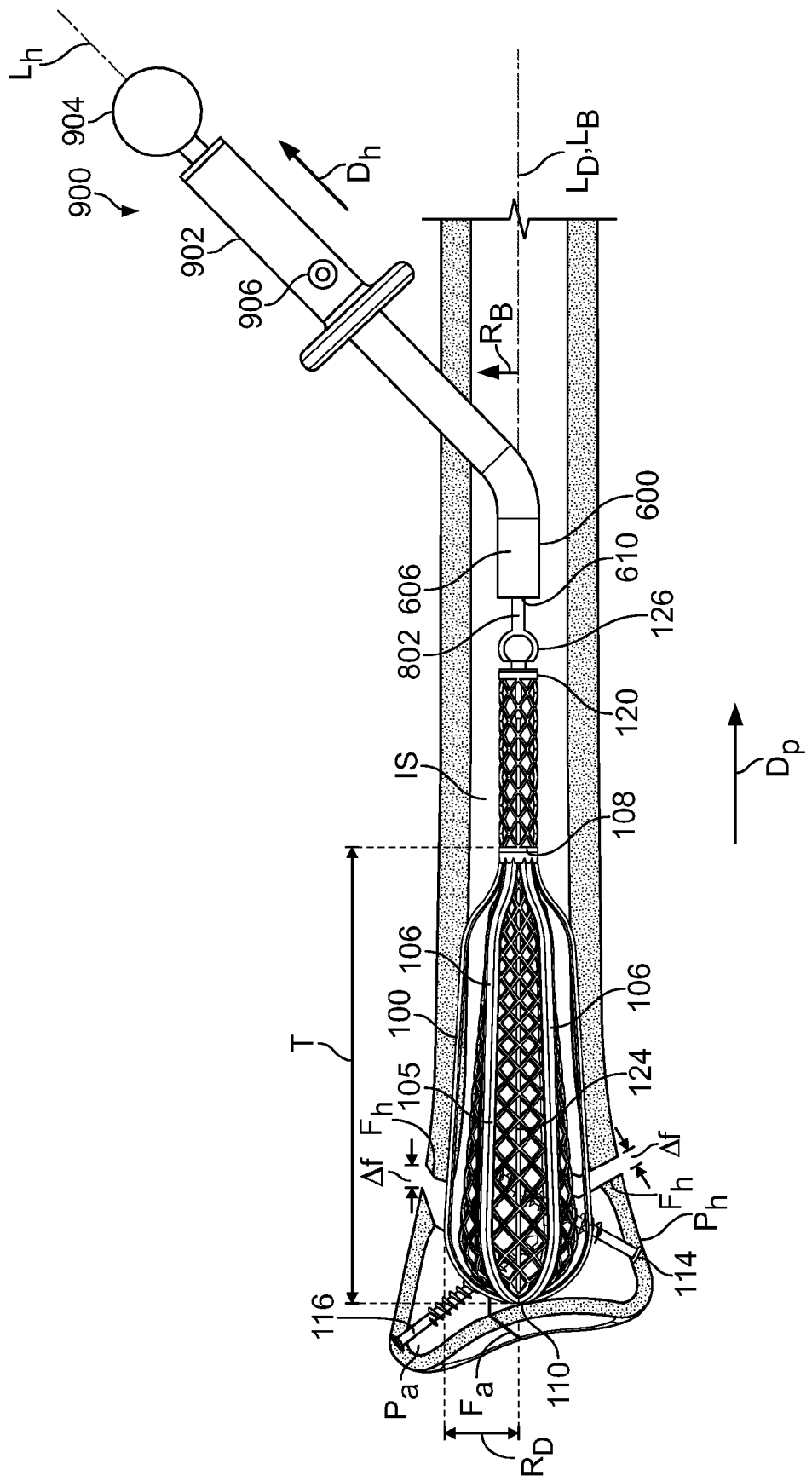
FIG. 12 is a partial sectional view of the apparatus shown in FIG. 1 along with additional apparatus in accordance with the principles of the invention.

FIG. 12 shows tensioning device 100 in intramedullary space IS of bone B. Anchors 114 and 116 have been completely or almost completely driven into bone segments $P_h$ and $P_a$, respectively. Anchors 114 and 116 are secured inside bone B by anchoring substrate 112. The inward forces applied by anchors 114 and 116, in concert with anchoring substrate 112, and the outward forces applied by support members 106 of structural cage 105, have brought bone segments $P_h$ and $P_a$ into alignment along fracture $F_a$ and have closed fracture $F_a$. The torque (applied to the anchors), angle and positioning of anchors 114 and 116 may be selected to provide a desired contact force between bone segments $P_h$ and $P_a$ along fracture $F_a$. The anchors may lock to anchor substrate 112 to prevent unintentional removal.

Fracture $F_h$ remains open by separation amount Δf, which separates $P_a$ and $P_h$ from $P_B$, the main segment of bone B. Intersegment compression of bone segments $P_a$, $P_h$ and $P_B$ may be provided using one or more of device 100, device delivery apparatus 800 and delivery apparatus controller 900. The compression may help reduce or eliminate Δf. The compression may promote healing. The compression may provide stability to the bone segments in rotation and bending.

In some embodiments, the compression may be provided by drawing device 100 in proximal direction $D_P$, substantially. Length T of device 100 may be fixed, at least temporarily. For example, length T may be held fixed using a mechanical relationship of central axis member 124 to cage base 108 and hub 110. Device 100 may then be drawn in direction $D_P$ by device delivery apparatus 800. Device delivery apparatus 800 may be drawn in direction $D_P$ by shaft 802. Shaft 802 may be drawn through lumen 610 using delivery apparatus controller 900.

Device 900 may include a mechanism that may be activated by a trigger or lever such as 904 or 906. Shaft 802 may be drawn by drawing delivery apparatus controller 900 in direction $D_h$ along axis $L_h$. Distal end 606 of sheath 600, to the extent that it remains in intramedullary space IS, will travel generally along direction $D_P$ and draw device 100 in that direction via device delivery apparatus 800.

In some embodiments, length T may be allowed to extend when device 100 is drawn in direction $D_P$. Hub 110 may be substantially retained in position relative to bone segment $P_a$. Cage base 108 may be allowed to be displaced in direction $D_P$. This may reduce radius $R_D$ of structural cage 105. When the radius of structural cage 105 is reduced, radially outward forces on bone may be reduced, canceled or reversed.

As the length of device 100 is increased while its radius decreases, device 100 may collapse partially or completely to its delivered state. Depending on the diameter of intramedullary space IS of bone, B such contraction may be desirable to obtain proper placement of the bone segments. After proper bone segment position is obtained, the radial diameter can be adjusted to achieve the desired shape and radial force. This condition can then be maintained by locking central axis member 124 at distal and proximal ends of device 100.

In some embodiments, a proximal portion of anchoring substrate 112 may be drawn in direction $D_P$. This may draw anchors such as 114 and 116 in direction $D_P$ and direction $-R_B$. Anchoring substrate 112 may be drawn in direction $D_P$ with a force that is greater, lesser or equal to that by which structural cage 105 is drawn in direction $D_P$.

In some embodiments, a physician may assess and, if appropriate, adjust one or more of segments Pa, Ph and PB to achieve a desired alignment. The assessment may be performed using fluoroscopic imaging, for example, using imaging system 404 (shown in FIG. 4). The assessment may be done under direct visualization during a full surgical cut down procedure.

Figure 13:
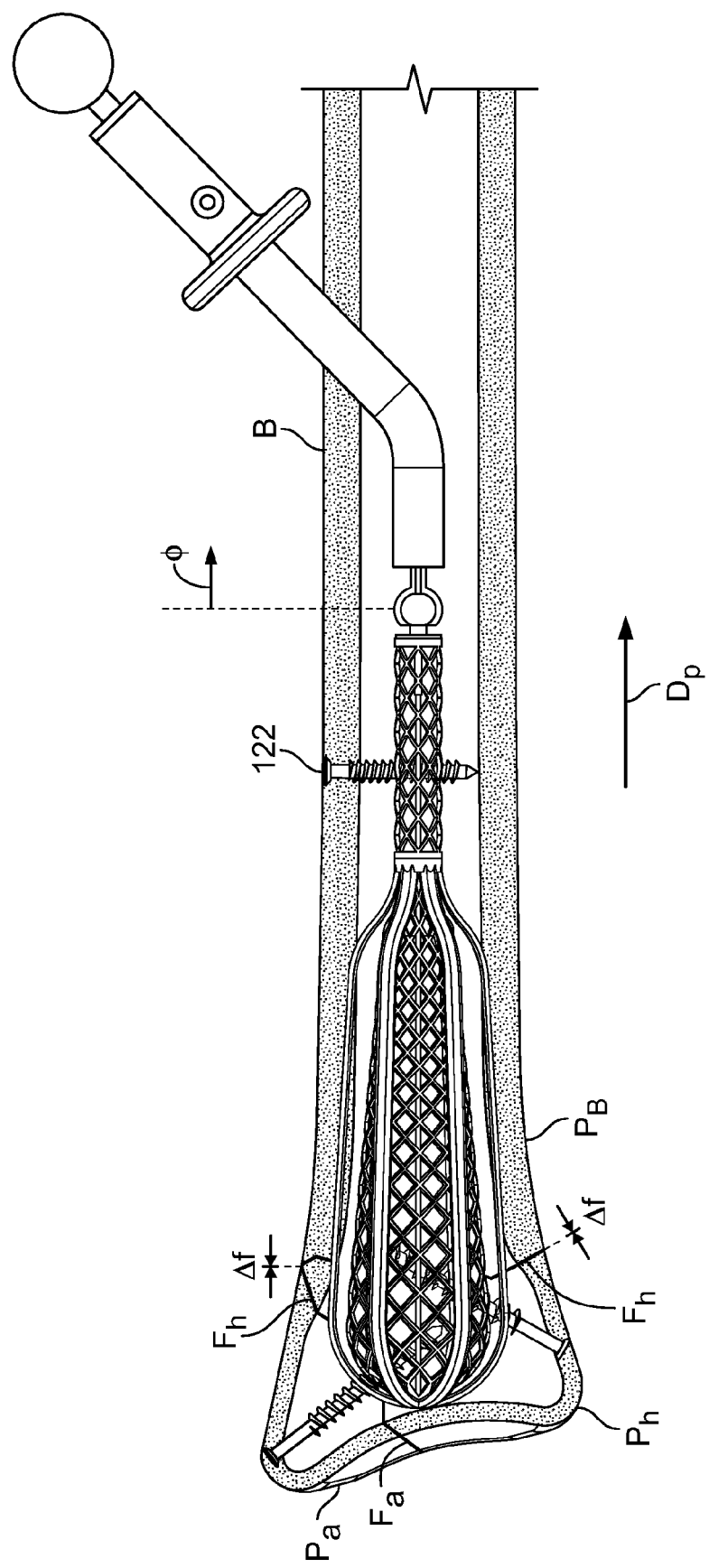
FIG. 13 is a partial sectional view of the apparatus shown in FIG. 1 along with additional apparatus in accordance with the principles of the invention.

FIG. 13 shows the application of force Φ in direction $D_P$. Force Φ is applied to device 100 at device retention member 126 by device delivery apparatus 800. Δf of fracture F has been stabilized, reduced or substantially eliminated. Anchor 122 is now inserted through bone B into stem 128. Anchor 122 may retain proximal portion of device 100 at or near an axial position along bone axis $L_B$. Anchor 122 may prevent device 100 from rotating about bone axis $L_B$. Anchor 122 may preserve the intersegment compression between bone segments $P_a$, $P_h$ and $P_B$. More generally, anchor 122 may preserve one or more of a desired position, orientation and state of stress for each of the individual bone segments. Anchor 122 may carry all or some of the load. Friction between structural cage 105 and other portions of device 100 may bear some of the load.

In some embodiments, the role of anchor 122 may be fulfilled by several anchors that may be used to lock device 100 in bone B while preserving the compression. Proximal anchors may gain purchase from both sides of the bone or just through one side. The angle of the anchors may range from near parallel to axis $L_D$ to perpendicular to axis $L_D$.

Figure 14:
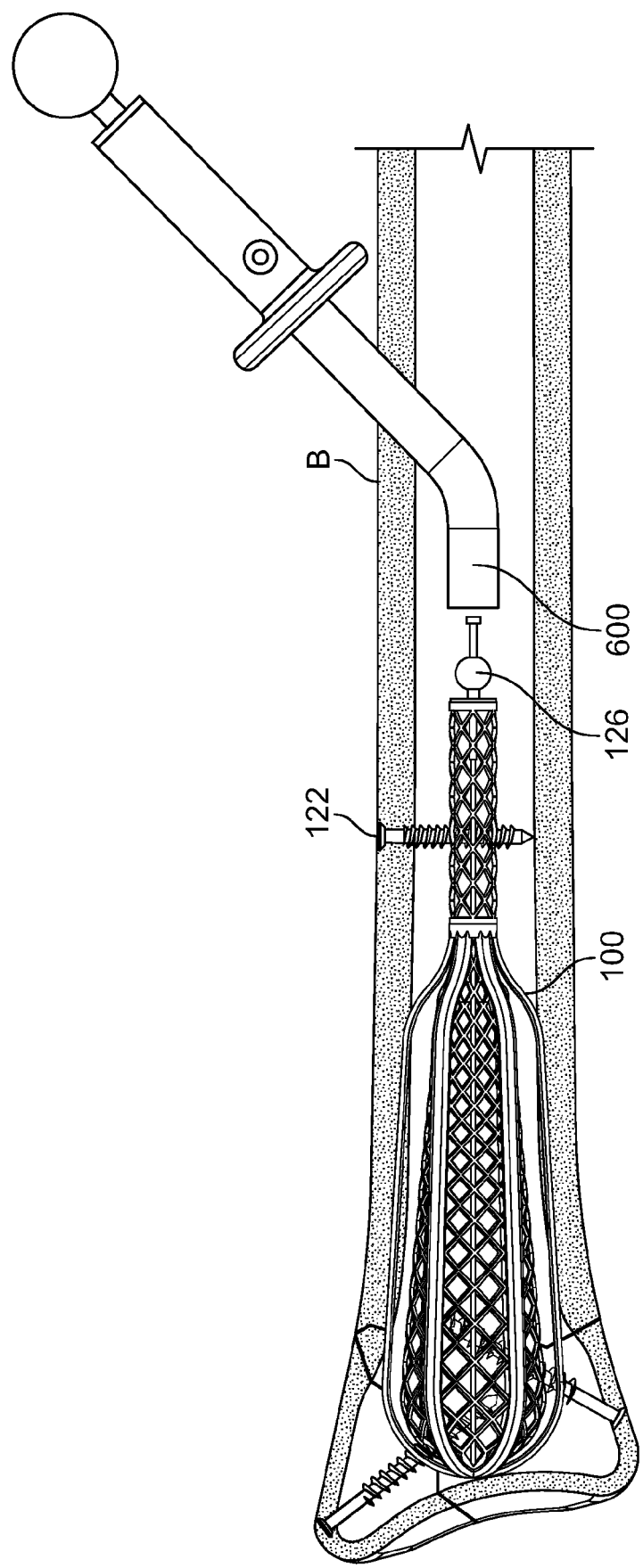
FIG. 14 is a partial sectional view of the apparatus shown in FIG. 1 along with additional apparatus in accordance with the principles of the invention.

FIG. 14 shows the release of device retention member 126 (by device delivery apparatus 800, which in FIG. 14 has been withdrawn into sheath 600). Device retention member 126 is shown as a simple keyed ball end that may be retained with a known grasping instrument. Other types of retention mechanisms are also considered and envisioned with respect to embodiments of the invention including but not limited to; threaded, socket, pinned, snap, collet, and any other mechanism known in the art.

Figure 15:
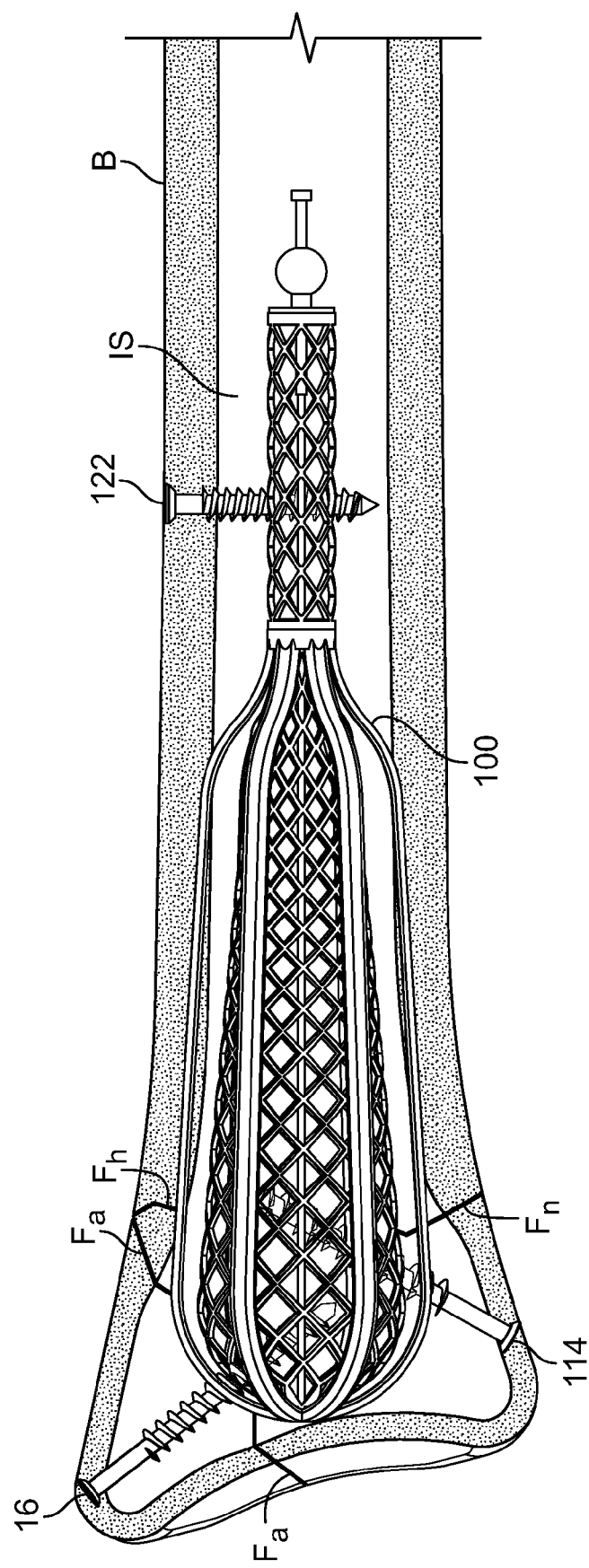
FIG. 15 is a partial sectional view of the apparatus shown in FIG. 1 along with additional apparatus in accordance with the principles of the invention.

FIG. 15 shows device in a final implanted state with sheath 600 (not shown) removed from intramedullary space IS of bone B. Device 100 retains segments $P_a$, $P_h$ and $P_B$ in compression relative to each other. Fractures $F_a$ and $F_h$ are reduced.

Figure 16:
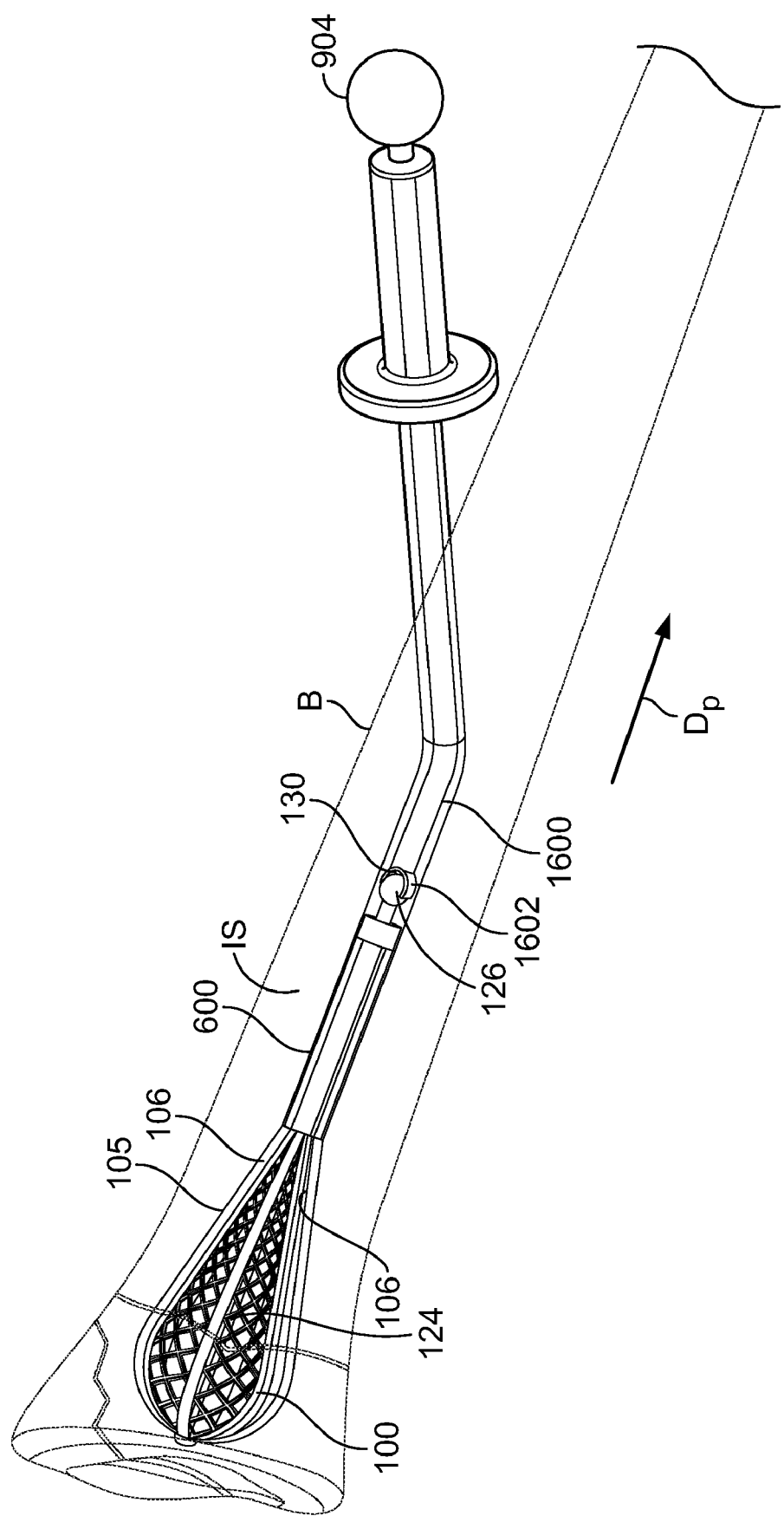
FIG. 16 is a partial sectional view of the apparatus shown in FIG. 1 along with additional apparatus in accordance with the principles of the invention.

FIG. 16 shows that device 100 may be recaptured in intramedullary space IS and removed from bone B. Illustrative delivery/recapture device 1600 may engage central member hub 130. Engagement member 1602 at the distal end of delivery/recapture device 1600 may slide over central member hub 130 and engage device retention member 126. Support members 106 of support cage 105 may contract as they are drawn into sheath 600.

Figure 17:
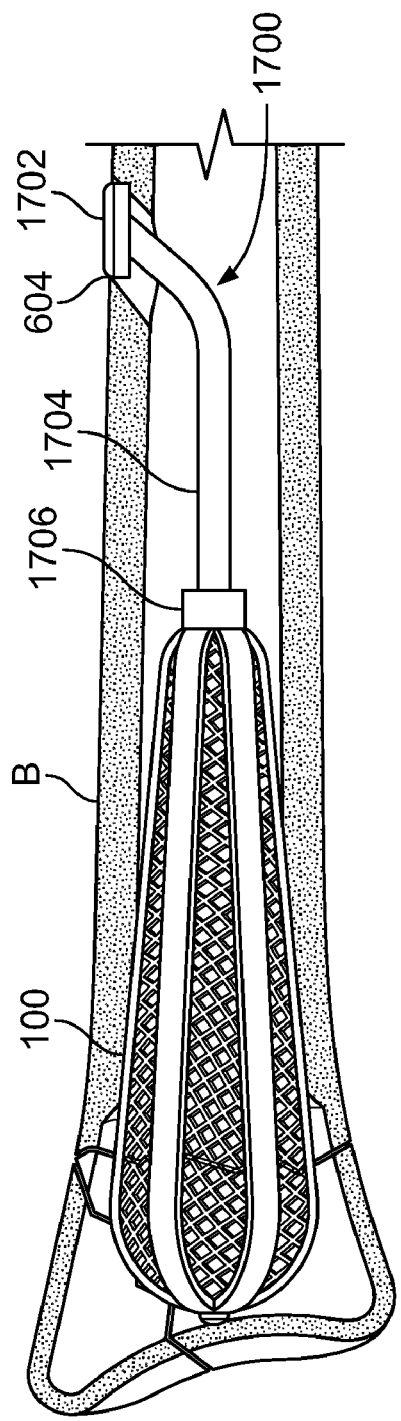
FIG. 17 is a partial sectional view of the apparatus shown in FIG. 1 along with additional apparatus in accordance with the principles of the invention.

FIG. 17 shows closure assembly 1700 that may be used to close hole 604 and preserve access to device 100 in bone B. Closure assembly 1700 may include plug 1702. Plug 1702 may seal or substantially seal hole 604. Plug 1702 may cap cannula 1704. Cannula 1704 may provide access to central member hub 130 (not shown) and device retention member 126 (not shown). Flange 1706 may engage with one or both of central member hub 130 (not shown) and device retention member 126 (not shown). Flange 1706 may be affixed to sheath 1704. Cannula 1704 may be configured to apply force to device 100 to adjust tension or radial diameter in structural cage 105 or anchoring substrate 112.

In some embodiments, some or all of the functionality provided by cannula 1704 may be provided by a cable or a shaft (not shown). In some of those embodiments, plug 1702 may be a threaded or ribbed plug, or a screw-like plug, that is linked to the cable.

Cap 1702 may be removed to insert an instrument such as engagement member 1602 to recapture device 100 in a manner such as that shown in FIG. 16.

Figure 18:
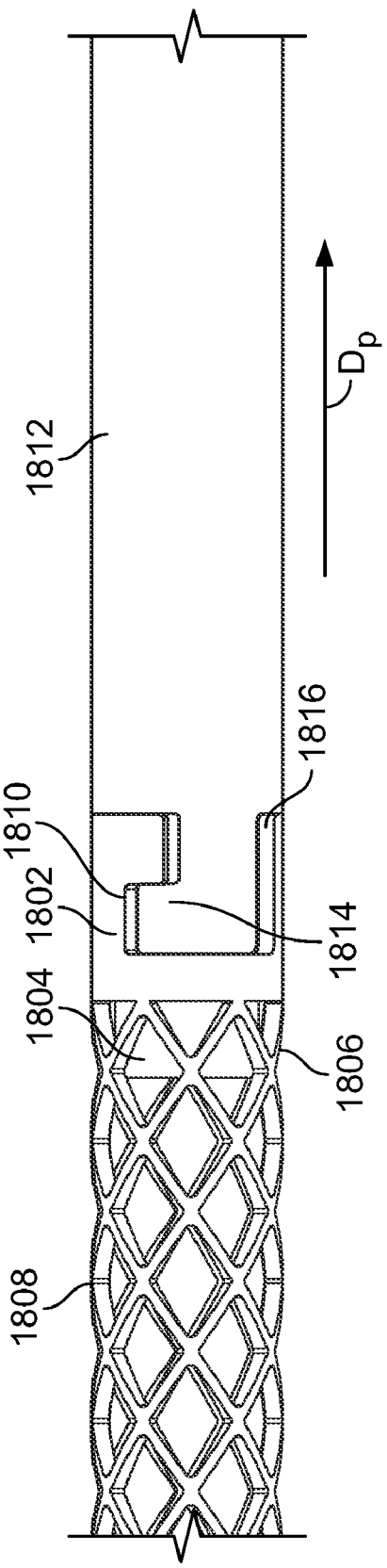
FIG. 18 is a partial sectional view of apparatus in accordance with the principles of the invention.

FIG. 18 shows illustrative delivery/recapture member 1802, which in some embodiments may be an alternative to device retention member 126 in a device such as 100 (shown in FIG. 1). Delivery/recapture member 1802 may be formed from a tube. Notch 1810 may be cut into the tube. Any appropriate number of notches such as 1810 may be present in delivery/recapture member 1802. Delivery/recapture member 1802 may include ferrule 1804, which may be affixed to proximal end 1806 of device stem 1806. Stem 1806 may correspond to stem 128 of device 100 (shown in FIG. 1).

Recapture instrument 1812 may include one or more blades such as blade 1814. Recapture instrument 1812 and blade 1814 may be cut from a tube to match delivery/recapture member 1802 and notch 1810, respectively. Recapture instrument 1812 may be delivered through a sheath such as 600 (shown in FIG. 6) into an intramedullary space to retrieve a device attached to stem 1808.

Recapture instrument 1812 may be aligned with delivery/recapture member 1802. Blade 1814 may be inserted into cut-out 1816 in delivery/recapture member 1802. Recapture instrument 1812 may be rotated such that blade 1814 moves into notch 1810. Recapture instrument 1812 may thus engage delivery/recapture member 1802 to pull the device in proximal direction $D_P$. Blade 1814 and delivery/recapture member 1802 may bend radially out of plane from each other to disengage. The bending may be achieved by bending or releasing a spring-like mechanism or by plastic deformation of recapture instrument 1812.

Figure 19:
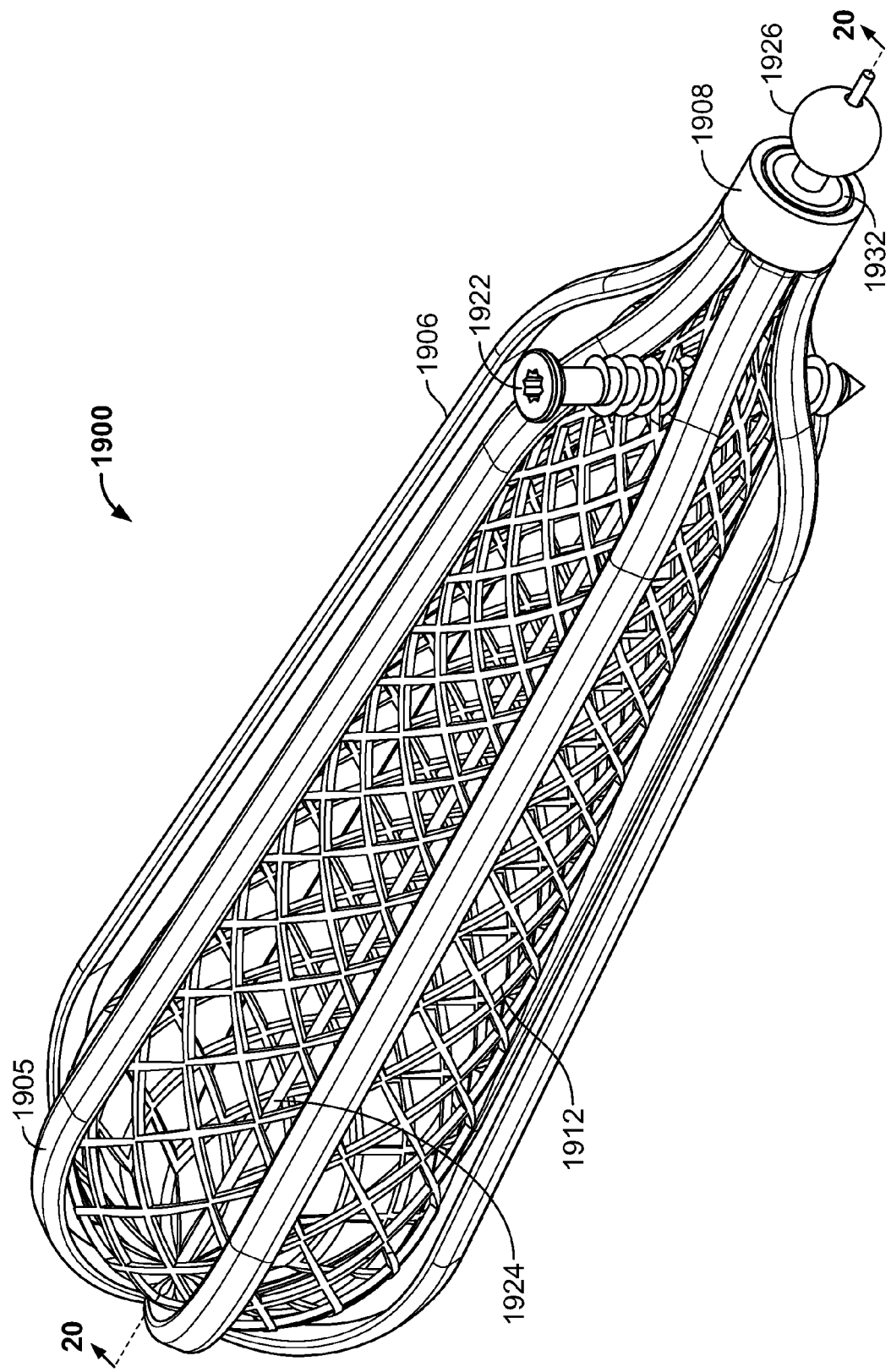
FIG. 19 is a perspective view of apparatus in accordance with the principles of the invention.

FIG. 19 shows illustrative device 1900. Device 1900 may have features that function like some or all of the corresponding features of device 100 (shown in FIG. 1). For example, device 1900 may include supports 1906 that form cage 1905. Cage 1905 may include cage base 1908. Anchoring substrate base 1932 may be present concentrically within cage base 1908. Device retention member 1926 may extend proximally from anchoring substrate base 1932. Device 1900 does not include a stem such as stem 128. Proximal anchor 1932 may be used to engage a bone such as B (shown in FIG. 1) with the proximal end of anchoring substrate 1912.

Figure 20:
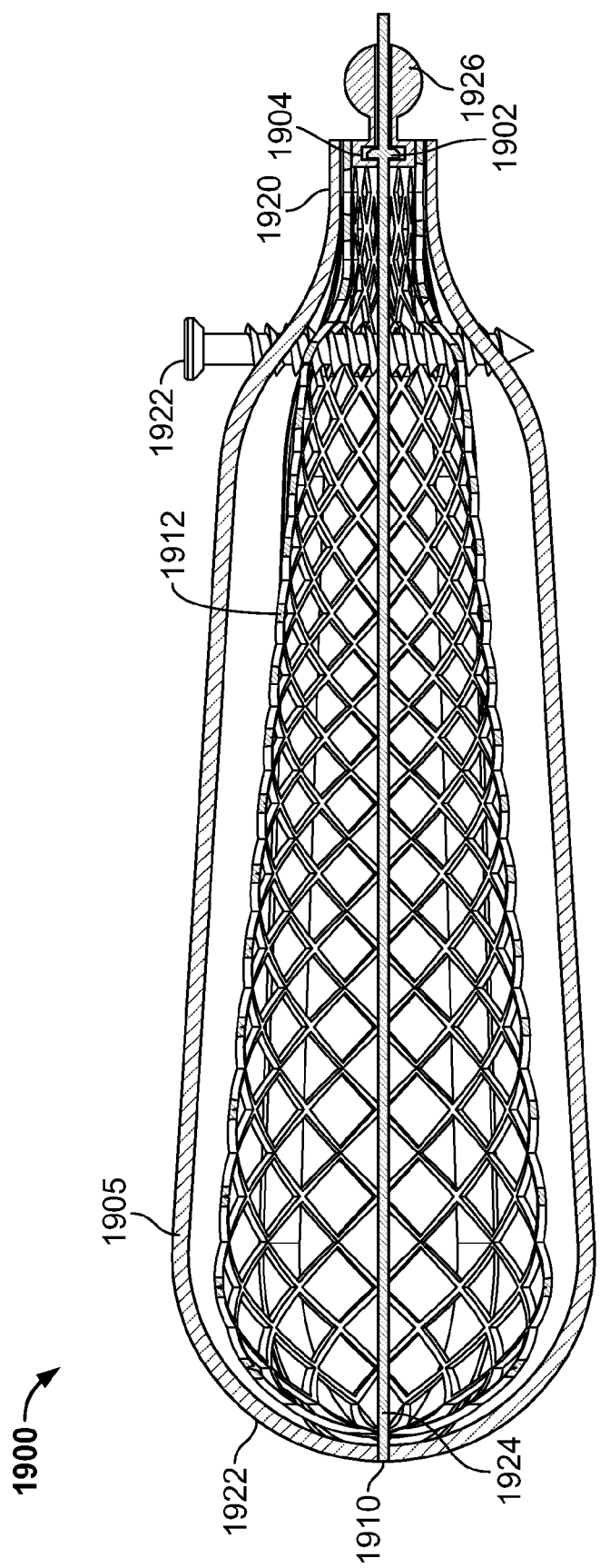
FIG. 20 is a partial sectional view of apparatus in accordance with the principles of the invention.

FIG. 20 shows a cross-section of device 1900 taken along lines 20-20 (shown in FIG. 19). Illustrative central axis member 1924 is fixed at hub 1910 of support cage 1905. Central axis member 1924 may include flange 1902. Flange 1902 may be mechanically locked into chamber 1904 of device retention member 1926. In some embodiments, central axis member 1924 may be moved axially until flange 1902 snaps into chamber 1904. This may lock-in central axis member 1924 between proximal end 1920 and distal end 1922 of device 1900 and thus provide axial tension that may support the radial stiffness of device 1900. Central axis member 1924 may distribute tension that may be applied to device retention member 1926 between proximal end 1920 and distal end 1922 of device 1900.

In some embodiments, device 1900 may be expanded before deployment (as in an open reduction). In such embodiments, structural support 1905 and anchoring substrate 1932 may be longitudinally fixed with respect to each other at proximal end 1920 and distal end 1922 of device 1900.

Figure 21:
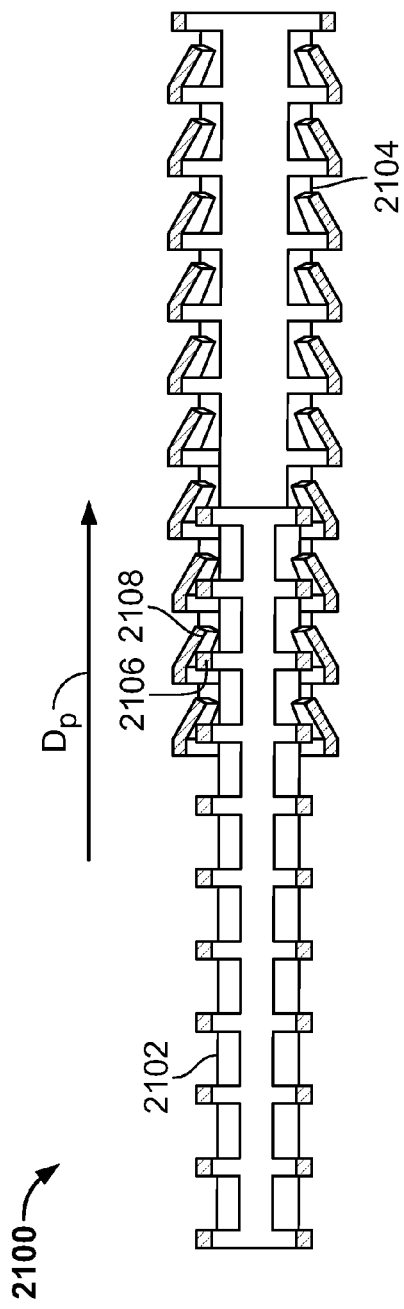
FIG. 21 is an end view of the apparatus shown in FIG. 20.

FIG. 21 shows, in cross-section, illustrative ratchet mechanism 2100. Ratchet mechanism 2100 may be used to preserve tension in a central axis member such as 124 (shown in FIG.

1). A portion of such a central axis member may be embodied as ribbed member 2102. Ribbed member 2102 may be drawn through tabbed member 2104 in proximal direction $D_P$. Rib 2106 may be drawn in direction DP by deflecting annular tab 2108. After rib 2106 passes annular tab 2108, annular tab 2108 moves back to its rest position (as shown) and prevents rib 2106 from moving back to a position that is distal to annular tab 2108.

Ratchet mechanism 2100 may be provided in or about an anchoring substrate base such as 132, in or about a stem such as 128, in or about a proximal base such 120 or in or about device retention member 126 (all shown in FIG. 1). Tabbed member 2104 may be longitudinally fixed to the device. The central axis member may be provided over a portion of its length with ribbed member 2102. The central axis member may thus be drawn in proximal direction $D_P$ and locked in place by annular tabs 2108. This may preserve tension in portions of the central axis member that are distal of tabs 2108.

Ratchet features may take on any shape or form to facilitate one-way locking. The one-way locking may be permanent or releasable. In some embodiments, tabs 2104 may be releasable so that ribbed member 2102 may be adjusted in either longitudinal direction.

The ratchet features may be incorporated into the apparatus. The ratchet features may be integral to one or more portions of the apparatus. For example, device stems, such as those shown in FIG. 25 may include complementary ratchet features so that when the stems are in a concentric relationship, the inner stem can move in only one direction.

Figure 22:
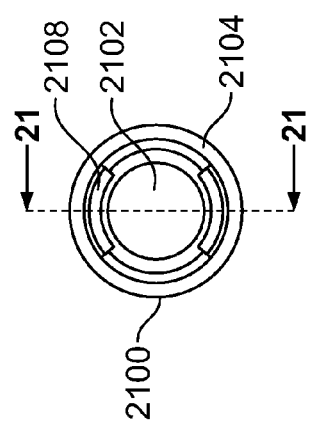
FIG. 22 is a partial sectional view of apparatus shown in FIG. 1.

FIG. 22 shows an end view of ratchet mechanism 2100 (shown in cross section, along lines 21-21, in FIG. 21).

Figure 23:
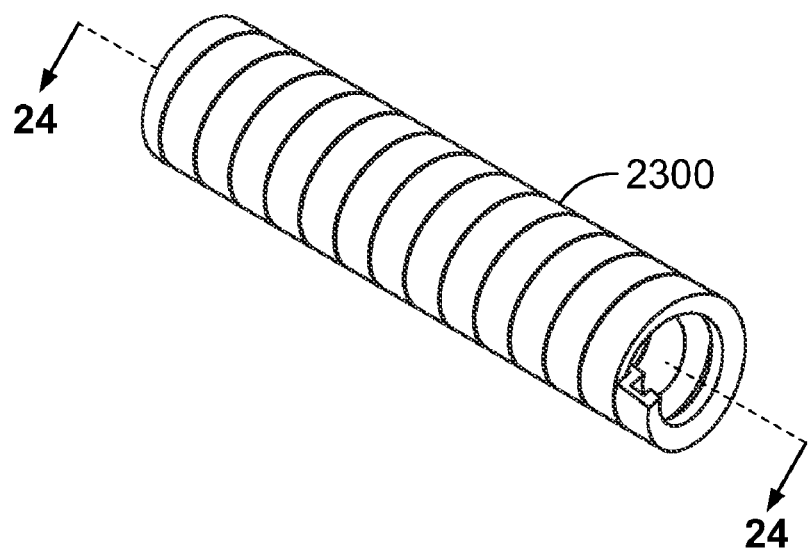
FIG. 23 is a perspective view of apparatus in accordance with the principles of the invention.

FIG. 23 shows illustrative stacking rings 2300 that may form all or a portion of a central axis member such as 124 (shown in FIG. 1). The rings are shown as one continuous helix. In some embodiments, the rings may be individual annular rings with stacking features similar to helical stacking rings 2300.

Figure 24:
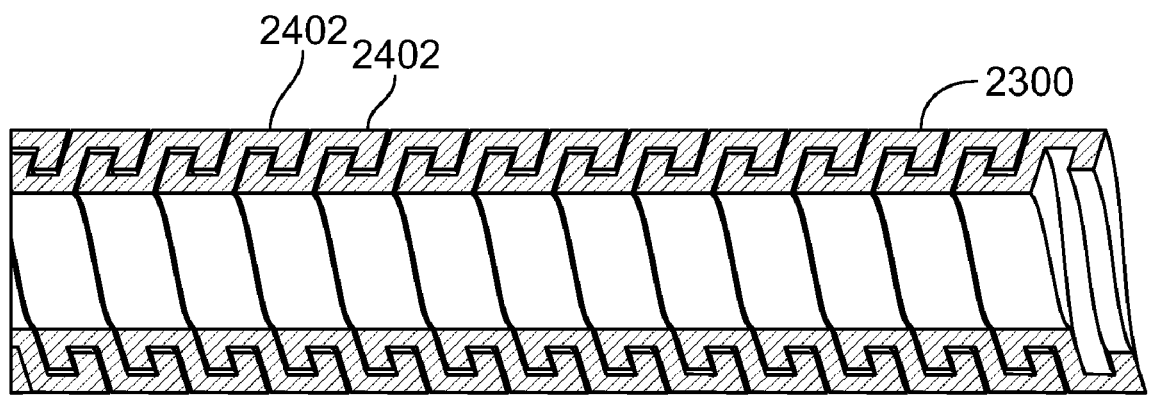
FIG. 24 is a partial sectional view of the apparatus shown in FIG. 23.

FIG. 24 is a cross-sectional view taken along lines 24-24. The helical rings form S-links that interlock with each other under longitudinal loading of the stack—either in compression or in tension. The shape of stacking rings 2300 is such that may they wedge together in either compression or tension and effectively reduce the mechanical degree of freedom to move relative to each other. All or a portion of a central axis member such as 124 (shown in FIG. 1) may include a segment of helical rings 2300. When loaded in tension or compression, the central axis member may become straight and rigid. The straightness and rigidity may increase the amount of load, whether in tension, compression, or bending, that may be supported by a device such as 100.

Figure 25:
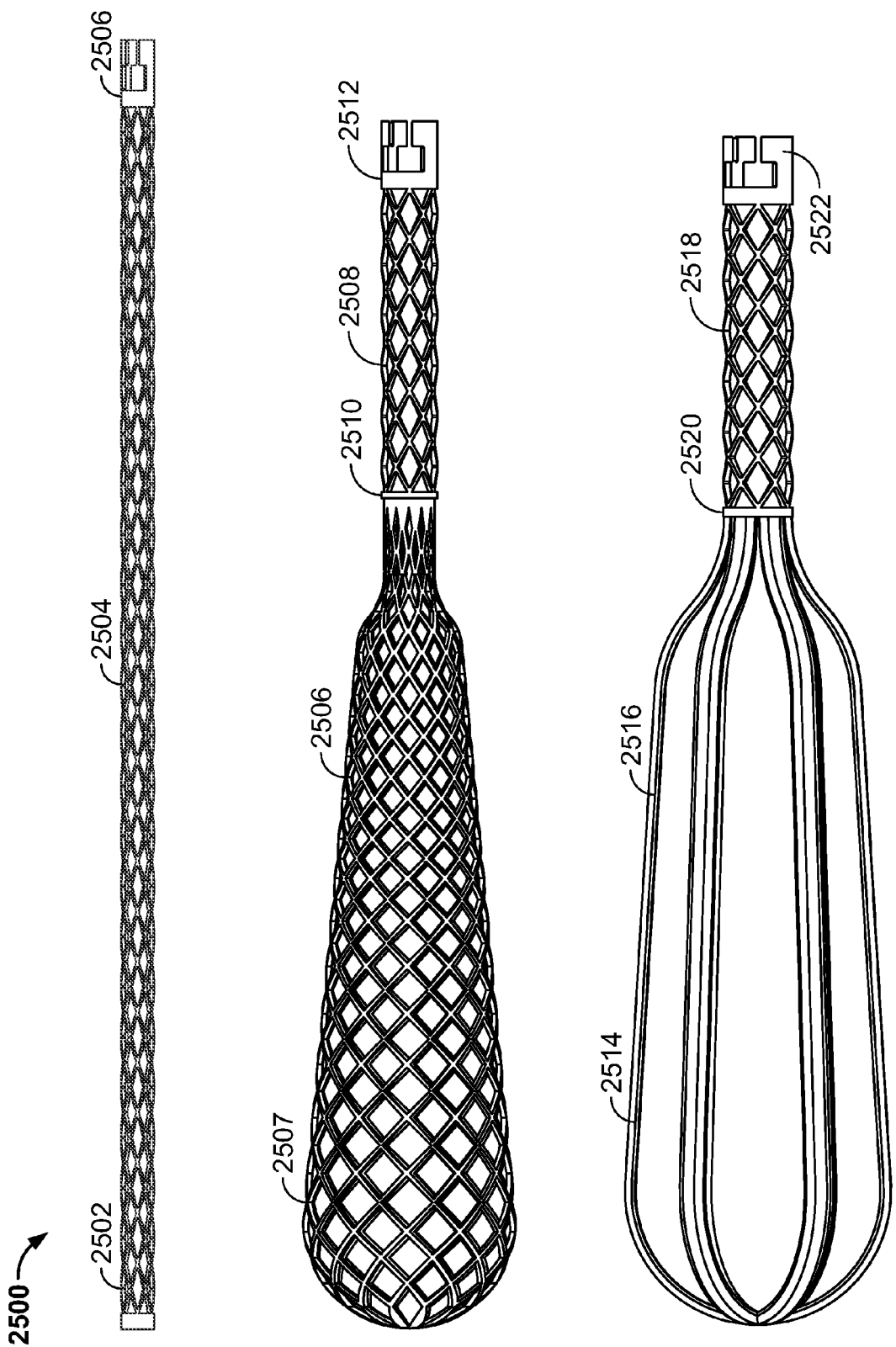
FIG. 25 is a side view of apparatus in accordance with the principles of the invention.

FIG. 25 shows illustrative device 2500, which is in accordance with the principles of the invention. Device 2500 may include central axis member 2502. Central axis member 2502 may include cellular body 2504. Central axis member 2502 may include device retention member 2506.

Device 2500 may include intermediate member 2507. Intermediate member 2507 may include anchoring substrate 2506. Anchoring substrate 2506 is shown in an expanded state. Intermediate member 2507 may include stem 2508. Stem 2508 may be continuous with anchoring substrate 2506. Neck support 2510 may provide structural support and connection between anchoring substrate 2506 and stem 2508. When anchoring substrate 2506 is in a contracted state, intermediate member 2507 may contract to a diameter substantially equivalent to that of stem 2508. Device retention member 2512 may be present at the end of stem 2508.

Device 2500 may include outer member 2514. Outer member 2514 may include support cage 2516. Support cage 2516 is shown in an expanded state. Outer member 2514 may include stem 2518. Stem 2518 may be continuous with support cage 2516. Neck support 2520 may provide structural support and connection between support cage 2516 and stem 2518. When support cage 2516 is in a contracted state, outer member 2514 may contract to a diameter substantially equivalent to that of stem 2528. Device retention member 2522 may be present at the end of stem 2518.

FIG. 25 shows inner member 2502, intermediate member 2507 and outer member 2514 separate from each other, but they may be used together to perform some or all of the functions of device 100 (shown in FIG. 1). Inner member 2502, intermediate member 2507 and outer member 2514 may respectively correspond, at least in part, to a central axis member such as 124, an anchoring substrate such as 112 and a support cage such as 105 (shown in FIG. 1).

One or both of intermediate member 2507 and outer member 2514 may be self-expanding. One or both of intermediate member 2507 and outer member 2514 may be expandable by mechanical actuation.

Figure 26:
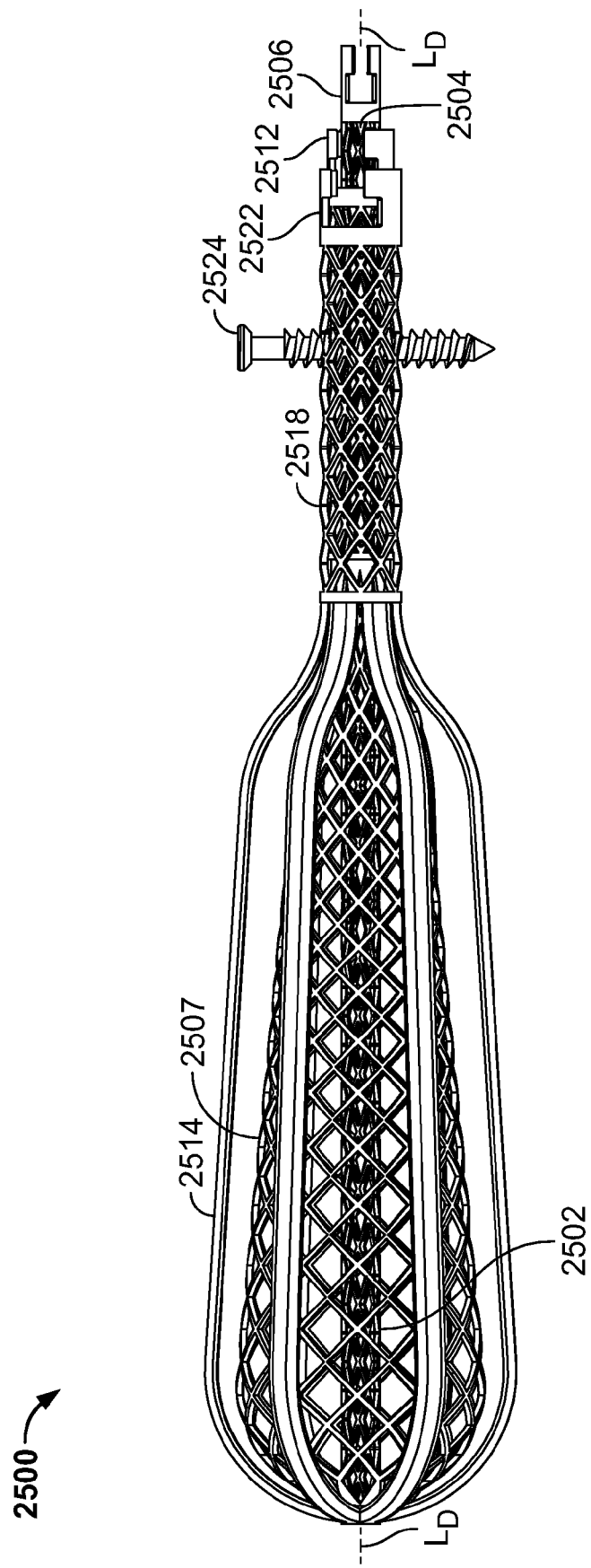
FIG. 26 is a side view of apparatus in accordance with the principles of the invention.

FIG. 26 shows device 2500 in an assembled and expanded configuration. Inner member 2502 extends longitudinally inside intermediate member 2507. Intermediate member 2507 extends longitudinally inside outer member 2514. Device retention members 2506, 2512 and 2522 extend from the proximal end of device 2500. Proximal anchor 2524 transects stems 2518 (of outer member 2514) and 2508 (of intermediate member 2507, not shown) and cellular body 2504 of inner member 2502.

In the absence of proximal anchor 2524, inner member 2502, intermediate member 2507 and outer member 2514 may be moved longitudinally, with respect to each other, along axis LD. The relative motion may be induced by delivery/recapture instruments engaged with each of the device retention members. For example, a delivery/recapture instrument such as 1812 (shown in FIG. 18) may be provided for each of the device retention members. The three recapture instruments may be coaxial with each other.

In some embodiments, one or more of inner member 2502, intermediate member 2507 and outer member 2514 may be coupled to each other at the distal end of device 2500 to obtain an appropriate response to the application of longitudinal and rotational forces that may be applied to one or more of inner member 2502, intermediate member 2507 and outer member 2514. The response may be modified by coupling one or more of inner member 2502, intermediate member 2507 and outer member 2514 to each other at a more proximal portion of device 2500.

Inner member 2502, intermediate member 2507 and outer member 2514 are shown having closed distal ends. In some embodiments, one or more of the members may have an open or free distal end.

In some embodiments of the invention, device 2500 may not include inner member 2502. Those embodiments may include intermediate member 2507 and outer member 2514. In some embodiments, device 2500 may include two or more intermediate members 2507 and or two or more outer members 2514. For example, in some embodiments, device 2500 may include inner member 2502, intermediate member 2507, outer member 2514 and, external to outer member 2514, a fourth member (not shown), that is similar to intermediate member 2507. In some embodiments, device 2500 may include, internal to the other members, a fourth member (not shown) that is similar to outer member 2514. The device may include, radially outside the fourth member, intermediate member 2507, a fifth member (not shown) that is similar to intermediate member 2507, and outer member 2514.

Figure 27:
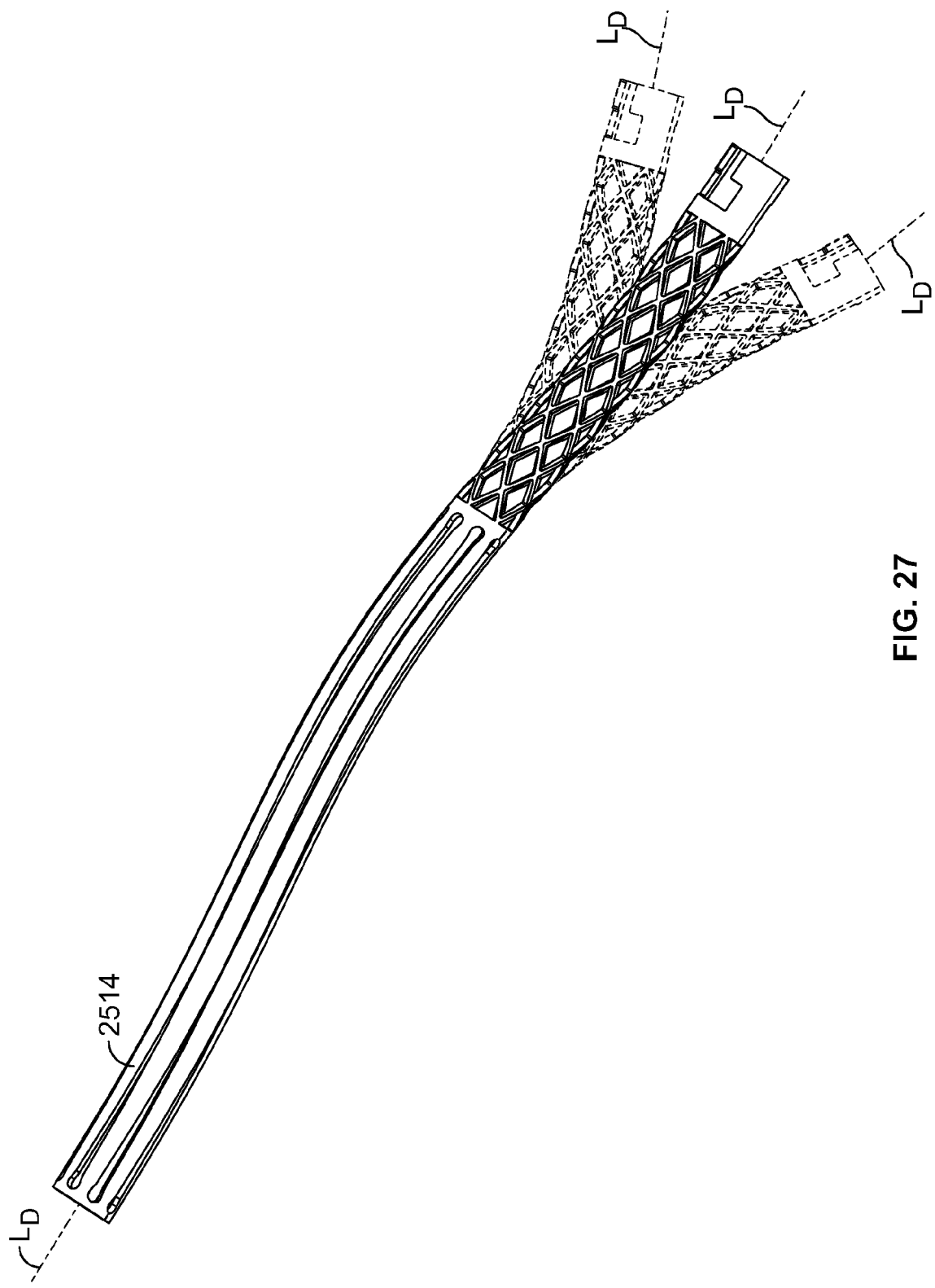
FIG. 27 is a perspective view of apparatus in accordance with the principles of the invention.

FIG. 27 shows outer member 2514 in a contracted state. In some embodiments, outer member 2514 may have bending flexibility along longitudinal axis $L_D$, as shown in FIG. 27. Inner member 2502 and intermediate member 2507 may also have bending flexibility along longitudinal axis LD. The flexibility may facilitate access into intramedullary space IS of bone B. In some embodiments, the contracted configuration of device 2500 may include curvature to facilitate access into intramedullary space IS of bone B.

Figures 28A, 28B, 28C:
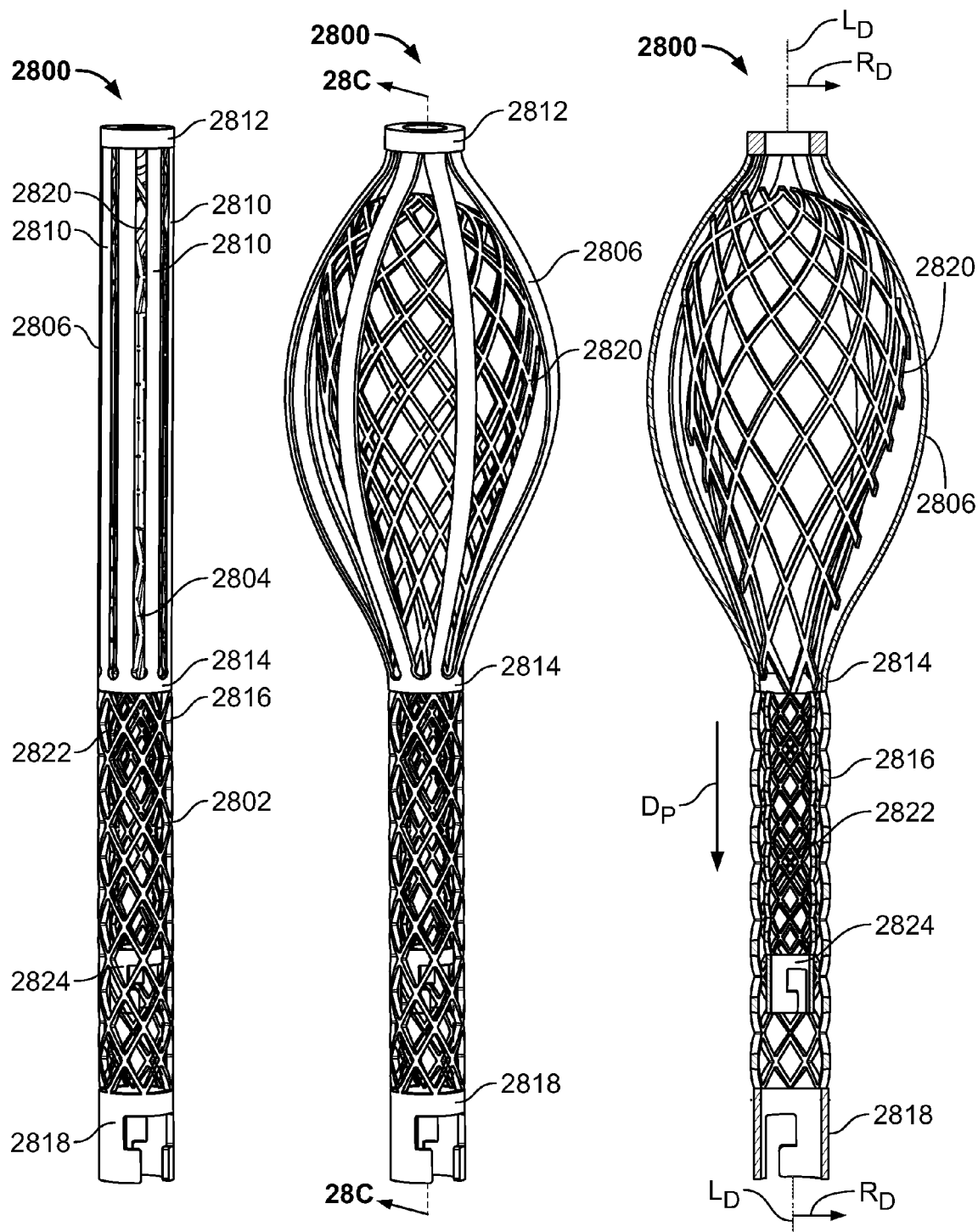
FIG. 28A is a side view of apparatus in accordance with the principles of the invention.
FIG. 28B is a side view of apparatus in accordance with the principles of the invention.
FIG. 28C is a partial sectional view of apparatus in accordance with the principles of the invention.

FIG. 28A shows illustrative two-member fracture repair device 2800. Device 2800 is shown in a contracted state. Device 2800 may be self-expanding or balloon-expanding. Device 2800 may include cage member 2802 and anchoring member (inside cage member 2802) 2804.

Cage member 2804 may include support cage 2806. Support cage 2806 may include support members 2810. Support members 2810 may terminate at distal hub 2812 and cage base 2814. Cage stem 2816 may extend proximally from cage base 2814. Cage stem 2816 may terminate at device retention member 2818. Support cage 2806 may be expanded in an intramedullary space IS (shown in FIG. 1).

Anchoring member 2804 may include anchoring substrate 2820. Anchoring member 2804 may include anchoring stem 2822 and device retention member 2824. In the contracted state, anchoring member 2804 may slide longitudinally within cage member 2804.

FIG. 28B shows device 2800 in the expanded state. Support cage 2806 is expanded. Anchoring substrate 2820 is expanded.

FIG. 28C shows is a partial cross section, taken along lines 28C-28C (shown in FIG. 28B) of device 2800 in the expanded state. Anchoring substrate 2820 is present inside support cage 2806. Anchoring stem 2822 is present inside cage stem 2816. Device retention member 2824 is present inside cage stem 2816.

Distal anchors may attach bone segments to anchoring substrate 2820. Device retention members 2824 and 2818 may be translated longitudinally, together or relative to each other, to apply force to the anchors in proximal direction $D_P$ and inward radial direction $-R_D$.

Device 2800 may be self-expanding. Device 2800 may be plastically deformable and be expanded by an outside force. One or more elements of device 2800 may be made from a unitary member such as a laser cut tube. One or more elements of device 2800 may be made individually and later assembled.

Figure 29:
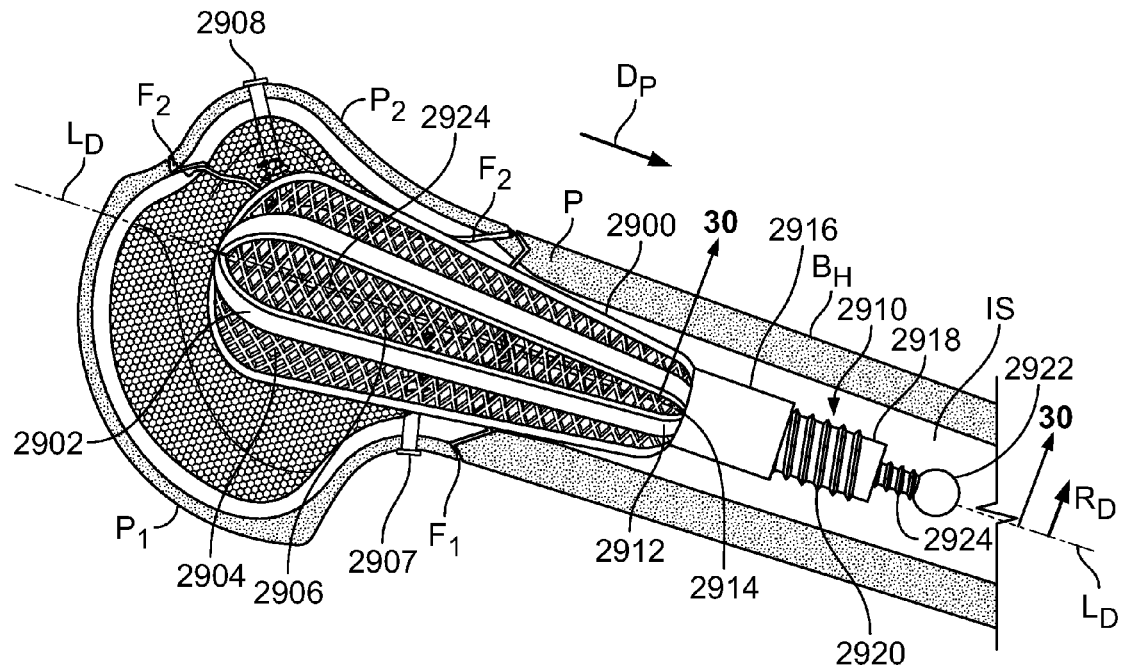
FIG. 29 is a side view of apparatus in accordance with the principles of the invention inside a body portion.

FIG. 29 shows illustrative bone fracture repair device 2900, which is in accordance with the principles of the invention. Device 2900 is shown inserted inside humerus $B_H$. Humerus $B_H$ includes fractures $F_1$ and $F_2$, which separate bone segments $P_1$ and $P_2$, respectively, from bone segment P. Device 2900 may include support cage 2902. Device 2900 may include anchoring substrate 2904. Support cage 2902 and anchoring substrate 2906 are shown in an expanded state. Device 2900 may include central axis member 2924.

Anchor 2907 and 2908 may be present to anchor bone segments $P_1$ and $P_2$, respectively, to anchoring substrate 2904.

Device 2900 may include relative displacement actuator 2910. Actuator 2910 may effect relative displacement of support cage 2902, anchoring support 2904 and central member 2906. During delivery of device 2900 to intermedullary space IS, device 2900 may be in a contracted state (not shown). During deployment, device 2900 may be expanded. The expansion may be performed, for example, by differential movement, along device longitudinal axis LD, of proximal portion 2912 of support cage 2902 and proximal portion 2914 of anchoring substrate 2904. During deployment, anchor 2907 and 2908 may be inserted after expansion of device 2900.

Device 2900 may include relative displacement actuator 2910 for effecting the differential displacement. Actuator 2910 may include threaded support cage base 2916. Threaded support cage base 2916 may be longitudinally fixed to proximal end 2912 of support cage 2902. Threaded support cage base 2916 may include a first threaded longitudinal bore (not shown).

Actuator 2910 may include double threaded anchoring substrate base 2918. Double threaded substrate base 2918 may be fixed to proximal portion 2914 of anchoring substrate 2904. Double threaded substrate base 2918 may have outer threads 2920 that may be screwed into the first longitudinal threaded bore of support cage base 2916. Double threaded substrate base 2918 may include a second threaded longitudinal bore (not shown).

Actuator 2910 may include threaded central axis member base 2922. Threaded central axis member base 2922 may be fixed to the proximal end of central axis member 2906. Threaded central axis member base 2922 may have outer threads 2924 that may be screwed into the second threaded longitudinal bore in double threaded substrate base 2918.

One or more control instruments may be deployed by catheter to rotate one or more of cage base 2916, double threaded anchoring substrate base 2918 and threaded central axis member base 2922 to achieve desired displacement or displacements between the proximal portions of support cage 2902, anchoring substrate 2904 and central axis member 2906. The differential displacements may expand the device during deployment.

After deployment of device 2901, anchors 2907 and 2908 may be inserted through bone segments P1 and P2, respectively, into anchoring substrate 2904. After insertion of anchors 2907 and 2908, relative displacement actuator 2910 may be used to adjust the stress state of bone segments $P_1$ and $P_2$. For example, double threaded anchoring substrate base 2918 may be rotated such that it moves in proximal direction DP relative to support cage base 2916. This relative motion would draw bone segments $P_1$ and $P_2$, relative to support cage 2902, in proximal direction DP and in inward radial direction $-R_D$.

After appropriate positioning of device 2900 and appropriate relative displacement of support cage 2902 and anchoring substrate 2904, a proximal anchor such as 1922 (shown in FIG. 19) may be inserted through femur $B_F$ and anchoring substrate 2904 to hold device 2900 in place.

Figure 30:
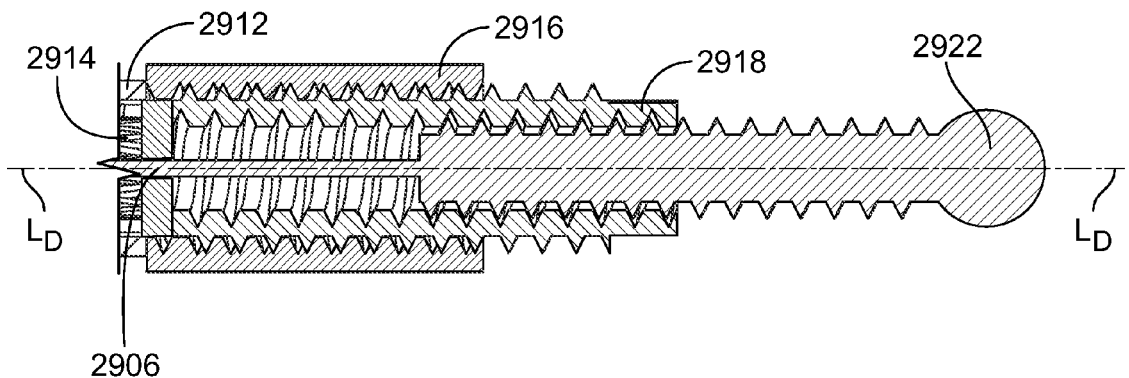
FIG. 30 is sectional view of a portion of the apparatus shown in FIG. 29.

FIG. 30 shows a cross-sectional view of device 2910 taken along lines 29-29 in FIG. 29. FIG. 29 shows threaded support cage base 2916 longitudinally fixed to proximal portion 2912 of support cage 2902. Double threaded anchoring substrate base 2918 is threaded into the first threaded bore of support cage base 2916. Double threaded anchoring substrate base 2918 is longitudinal fixed to proximal portion 2914 of anchoring substrate 2904. Threaded central axis member 2922 is threaded into the second threaded bore of double threaded anchoring substrate base 2918. Central axis member 2906 extends in distal direction $(-D_P)$ from threaded central axis member 2922.

FIG. 31 shows illustrative balloon-expandable fracture repair device 3100. Device 3100 may include outer structural member 3102. Outer structural member 3102 may include structural cage 3104, stem 3106 and device retention member 3108. Device 3100 may include anchoring member 3110.

Anchoring member 3110 may include anchoring substrate 3112, anchoring member stem 3114 and device retention member 3116.

Structural cage 3104 and anchoring substrate 3112 may be positioned in a contracted state in an intramedullary space of a bone using device retention members 3108 and 3116, respectively. The device retention members may be used to position structural cage 3104 and substrate 3112 longitudinally relative to each other.

Balloon 3118 may be present inside anchoring substrate 3112. Catheter 3120 may provide appropriate gas pressure for inflation of anchoring substrate 3112.

Membrane 3130 may be present about outer structural member 3102. Membrane 3130 may substantially entirely cover device 3130. Membrane 3130 may be disposed on the exterior or interior of device 3100, or between described elements of device 3100.

Membrane 3130 may include elastic material. Membrane 3130 may include non-elastic material. Membrane 3130 may include woven polyester, EPTFE film, a PET balloon, a silicon film, a polyurethane film, any suitable material that may be produced in a film form, any suitable material that may inhibit tissue growth, any suitable biocompatible, biodegradable and/or bioabsorbable material, and any other suitable material.

Membrane 3130 may facilitate the removal of the device 100 by inhibiting bone growth into device 100. In some embodiments, membrane 3130 may inhibit ingrowth of tissue in interstitial spaces of device 3100.

In some embodiments, membrane 3130 may facilitate the delivery or recapture of material that may be used in connection with device 3100, such as bone cement.

Membrane 3130 may be structurally integrated into device 3100. Membrane 3130 may be configured to be used with device 3100 as an ancillary or accessory component. The component may be used as needed for fracture repair.

In some embodiments, membrane 3130 may be used to expand structural cage 3104. In some embodiments, membrane 3130 may be used to expand anchoring substrate 3112. In such embodiments, membrane 3130 may be detachable from structural cage 3104 and/or anchoring substrate 3112. Membrane 3130 may then remain implanted in the intramedullary space IS.

In some embodiments, membrane 3130 may be removable independently of other elements of device 3100.

Membrane 3130 may include an agent. The agent may be impregnated in membrane 3130. The agent may be present as a coating on membrane 3130. The agent may provide a bone growth promotion agent, a bone growth inhibition or prohibition agent, a drug eluting agent or any other suitable agent.

FIG. 32 shows a cross sectional view taken along lines 32-32 of device 3100. FIG. 32 shows catheter 3120 entering anchoring substrate 3112. Balloon 3118 may be filled from ports 3122 in catheter 3120. Anchoring substrate contour 3124 may be predetermined by its materials and construction (or both).

Figure 33:
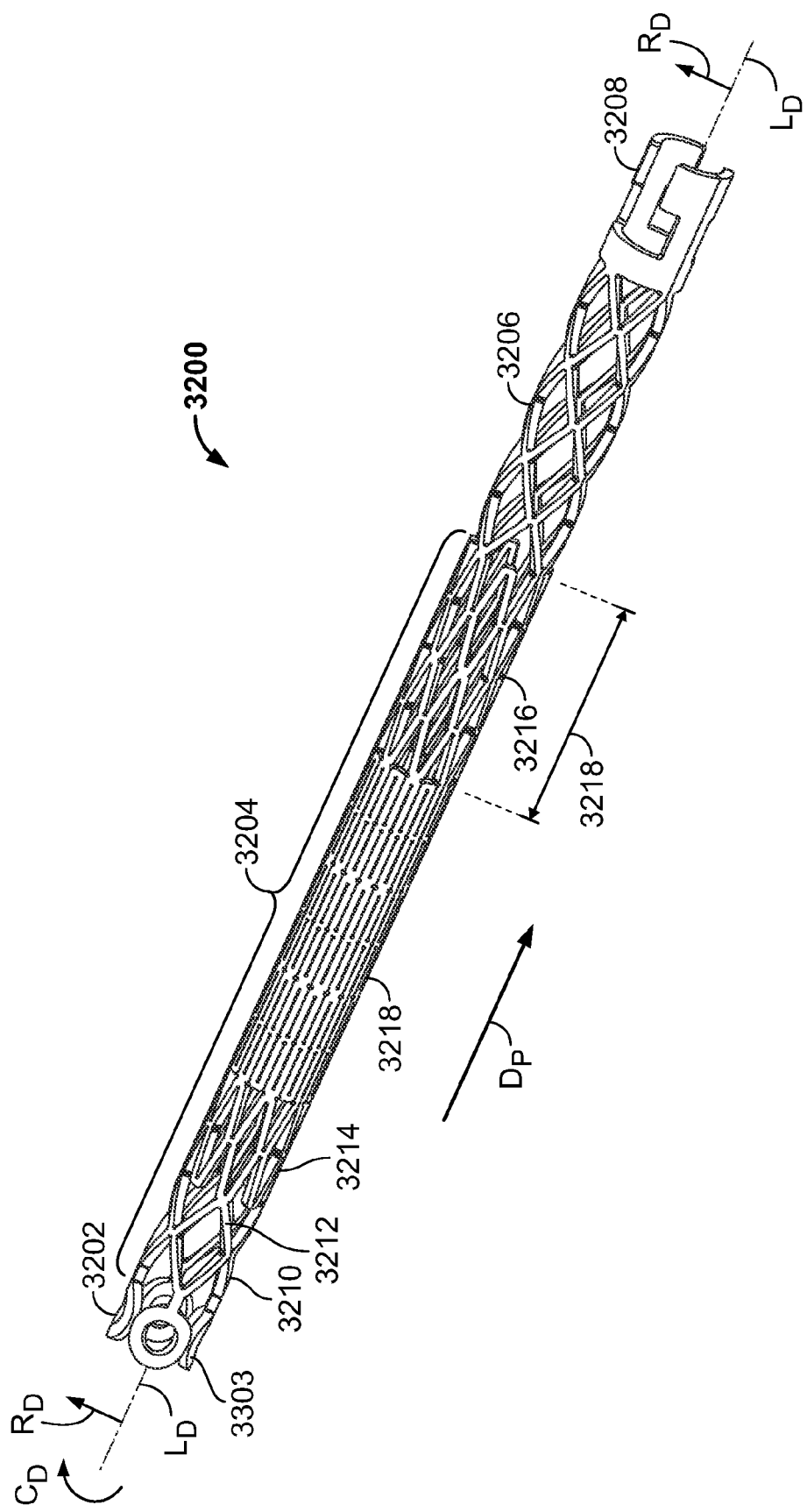
FIG. 33 is a perspective view of apparatus in accordance with the principles of the invention.

FIG. 33 shows illustrative anchoring member 3300. Anchoring member 3300 may be used in a device such as device 3100 (shown in FIG. 31) and may correspond to anchoring member 3110. Anchoring member 3300 may include distal ring 3302, anchoring substrate 3304, stem 3306 and device retention member 3308.

In some embodiments, a balloon such as 3118 (shown in FIG. 31) may be inserted inside anchoring member 3300 to expand anchoring member 200. In some embodiments, device 3300 may be self-expanding.

Collar 3302 has a substantially fixed radius and may not expand. Collar 3302 may include rings 3303. Rings 3303 may be arranged in a nested configuration in which rings 3303 are partially or substantially perpendicular to axis $L_D$. Rings 3303 may be coaxial with axis $L_D$. In such configurations, rings 3303 may facilitate coupling to a central axis member such as 124 (shown in FIG. 1) and/or a structural cage such as 105 (shown in FIG. 1).

When a balloon is used for expansion, the balloon may be situated a sufficient distal distance away from stem 3306 so that the radius of stem 3306 remains substantially the same during expansion of the balloon.

Anchoring substrate 3304 may include expansion band 3310. Expansion band 3310 includes expansion cells such as 3312, which may deform along directions $C_D$ and $-C_D$ under radially outward (direction RD) stress from the expanding balloon. Band 3310 has a number of expansion cells along its circumference. The number of expansion cells along the circumference of a band such as 3310 is referred as the cell density.

Groups of cells that are relatively expandable in response to a longitudinal compression may be considered to have a high "expansion ratio." Groups of cells that are relatively inexpandable in response to the same longitudinal compression may be considered to have a low "expansion ratio." Variations in cell density, cell shape, cell "leg" (material bordering the cell that separates the cell from other cells or material) (or "strut") length, cell leg thickness and other suitable parameters may be used to vary the expansion ration.

Anchoring substrate 3304 may include expansion band 3314. Expansion band 3314 has a cell density that is greater than the cell density of band 3310. When subjected to outward radial force from the balloon, expansion band 3314 will thus expand in radial direction $R_D$ more than expansion band 3310 will expand. Expansion band 3316 has the same cell density as expansion band 3314. Expansion band 3318 has the greatest cell density and therefore may expand in radial direction $R_D$ more than the other expansion bands.

The longitudinal variation in cell density along longitudinal anchoring substrate 3340 may result in a radial expansion that varies. Cell density, band width (such as band 3316 width 3318) and band position along axis $L_D$ may be chosen to provide an expanded contour of anchoring substrate 3304 that conforms in a desired way to a support cage such as 105 (shown in FIG. 1) or an intramedullary space such as IS (shown in FIG. 1). Circumferential variations (in direction $C_D$) in cell density may provide circumferentially varying expansion radii. Such variations may be used to provide an anchoring substrate that has a contour that corresponds to, or contours with, an asymmetric intramedullary cavity, such as at the end of a humerus.

Figures 34, 35:
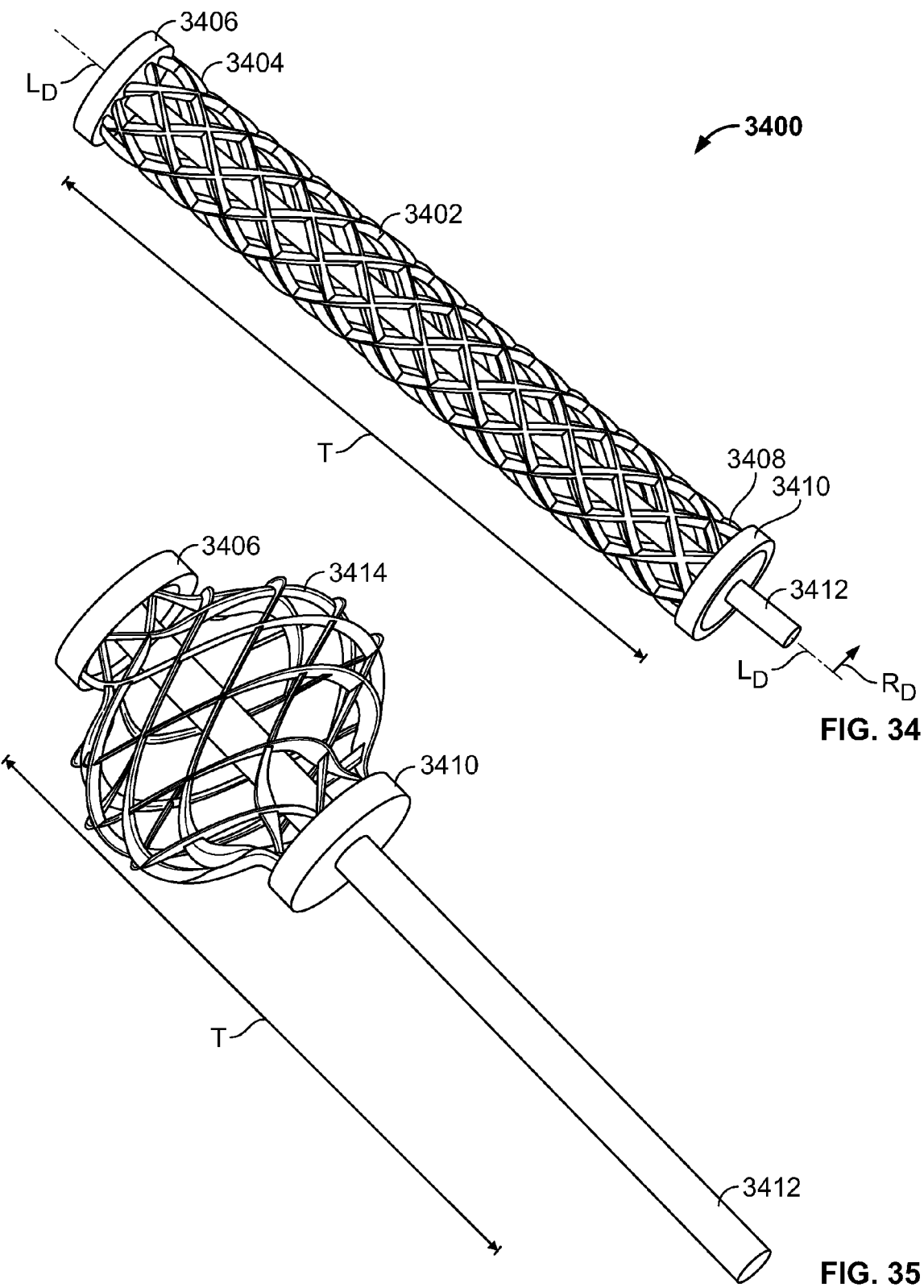
FIG. 34 is a perspective view of apparatus in accordance with the principles of the invention.
FIG. 35 is a perspective view of apparatus in accordance with the principles of the invention.

FIG. 34 shows illustrative anchoring substrate 3402 for a fracture repair device in accordance with the principles of the invention. Anchoring substrate 3402 may be supported at distal end 3404 by flange 3406. Anchoring substrate 3402 may be supported at proximal end 3408 by flange 3410. Central axis member 3412 may be longitudinally fixed to flange 3406. Flange 3410 may be substantially free to translate with respect to central axis member 3412. This allows distance T between the flanges to decrease so that anchoring substrate 3402 can expand in radial direction $R_D$.

Device 3400 may be self-expanding. Anchoring substrate 3402 may include braided mesh. In some embodiments, device 3400 may include multiple anchoring substrates.

FIG. 35 shows anchoring substrate 3414 in an expanded state between flanges 3406 and 3410. Flange 3410 has been moved distally up central axis member 3412. Anchoring substrate 3414 corresponds to anchoring substrate 3402 (shown in FIG. 34), but may have a longitudinally varying cell density and may therefore expand to a greater radius then can anchoring substrate 3402.

After anchors are attached to anchor substrate 3414, flange 3410 may be drawn proximally to reduce the diameter of the substrate and apply a tensile force to the attached anchor elements. During such diameter reduction, the shape of the cells in anchoring substrate 3414 may change. For example, the cells may, in the expanded state, be generally square. In the contracted (or relatively contracted) state, the cells may be diamond-shaped or trapezoidal. The shape change may increase the strength of the engagement between the anchoring substrate 3414. The shape change may effectively lock the anchor into anchoring substrate 3414.

Figure 36:
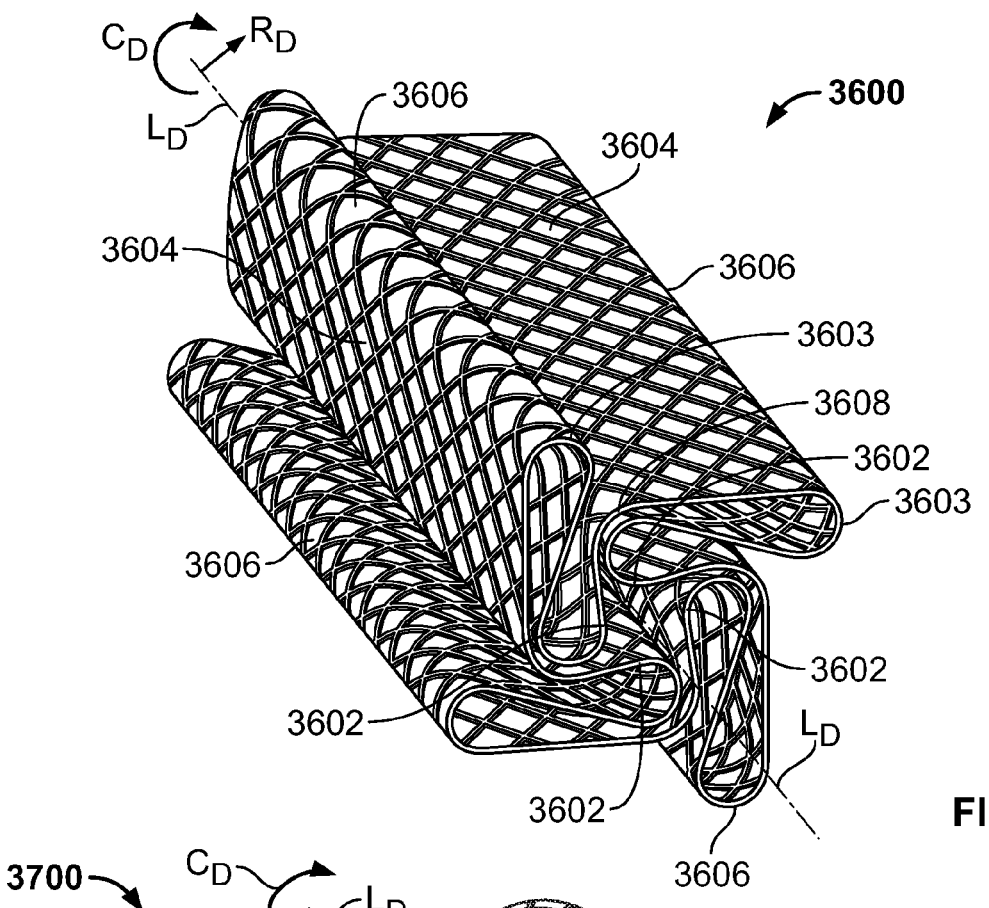
FIG. 36 is a perspective view of apparatus in accordance with the principles of the invention.

FIG. 36 shows illustrative anchoring substrate 3600 for a fracture repair device in accordance with the principles of the invention. Anchoring substrate 3600 may be attached to a central axis member (not shown). Anchoring substrate 3600 may be welded, crimped, woven or otherwise attached to the central axis member along the length of the central axis member. For example, radially inner portions 3602 may be attached to the central axis member.

In some embodiments, anchoring substrate 3600 may be attached at its distal and proximal ends to a central member such as 124 (shown in FIG. 1) and along its length to a structural cage such as 105 (shown in FIG. 1). This type of attachment may to facilitate wrapping or folding through relative rotation between the cage and central member. In some embodiments, anchoring substrate 3600 may be present within a structural cage such as 105 (shown in FIG. 1), but may be unattached or uncoupled to the structural cage.

Anchoring substrate 3600 may have sufficient elasticity to retain folds 3603. Surfaces 3604 and radially outer portions 3606 may engage anchors that press bone segments against a support cage such as 105 (shown in FIG. 1). Anchoring substrate 3600 may include secondary folds 3608 to increase the availability of surfaces 3604 to receive anchors.

The central axis member may be rotated in direction $-C_D$ to draw the anchors inward in direction $-R_D$ approximately toward the central axis member. The central axis member may be drawn proximally to apply longitudinal force to the bone segments.

Figure 37:
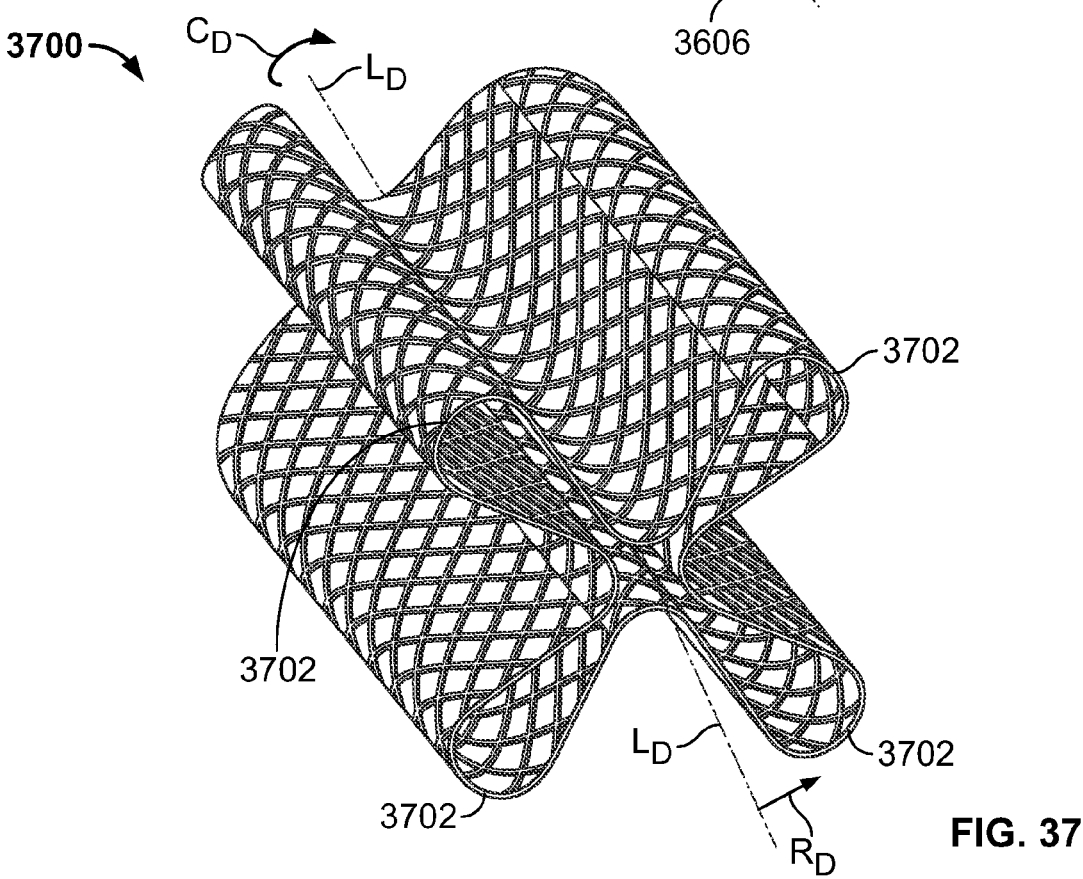
FIG. 37 is a perspective view of apparatus in accordance with the principles of the invention.

FIG. 37 shows illustrative anchoring substrate 3700 for a fracture repair device in accordance with the principles of the invention. Anchoring substrate 3700 may be constructed, attached to a central axis member and actuated as is anchoring substrate 3600 (shown in FIG. 36). Anchoring substrate 3700 may include primary folds 3702. Anchoring substrate 3700 may not include secondary folds such as 3608 in anchoring substrate 3600.

Some embodiments may include threadlike elements that are intertwined with anchoring substrate 3600 and/or a structural cage such as 105 (shown in FIG. 1). The threadlike elements may be connected to the central axis member to facilitate drawing portions of the anchoring substrate or structural cage toward the device axis. In some embodiments, the threadlike elements may be pulled through the central axis member by a delivery instrument.

Figure 38:
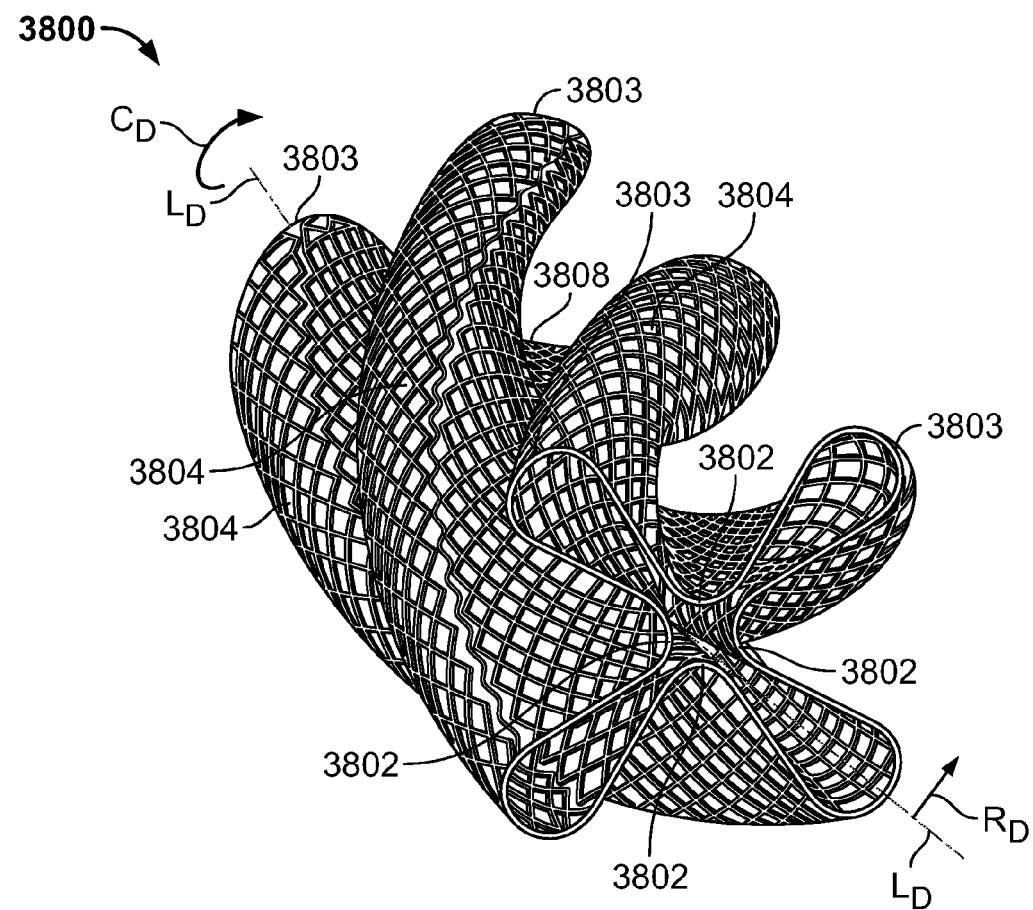
FIG. 38 is a perspective view of apparatus in accordance with the principles of the invention.

FIG. 38 shows illustrative anchoring substrate 3800 for a fracture repair device in accordance with the principles of the invention. Anchoring substrate 3800 may be attached to a central axis member (not shown). Anchoring substrate 3800 may be welded, crimped or otherwise attached to the central axis member near a proximal end of the central axis member. For example, radially inner and proximal portions 3802 may be attached to the central axis member. Anchoring substrate may have sufficient elasticity to retain helical folds 3803. Folded surfaces 3804 may engage anchors that press bone segments against a support cage such as 105 (shown in FIG. 1).

Distal end 3808 of anchoring member 3800 may be fixed to a flange, such as 3406 (shown in FIG. 35). The central axis member may be free to rotate in direction $-C_D$ with respect to the flange. When the central axis member is so rotated, it may tighten helical folds 3803 and draw the anchors inward in direction $-R_D$ approximately toward the central axis member. The central axis member may be drawn proximally to apply longitudinal force to the bone segments.

Figure 39:
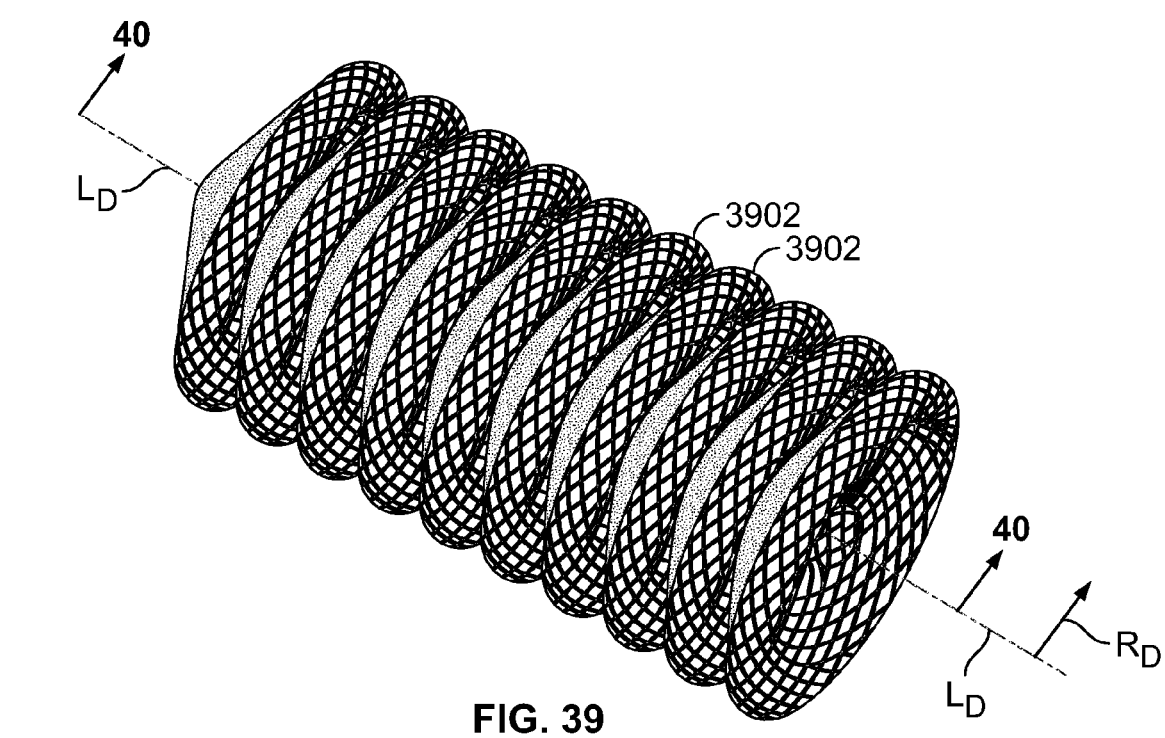
FIG. 39 is a perspective view of apparatus in accordance with the principles of the invention.

FIG. 39 shows illustrative anchoring substrate 3900 for a fracture repair device in accordance with the principles of the invention. Anchoring substrate may include stacked disc-like folds 3902. Disc-like folds may expand and contract longitudinally and radially in an accordion-like fashion.

Figure 40:
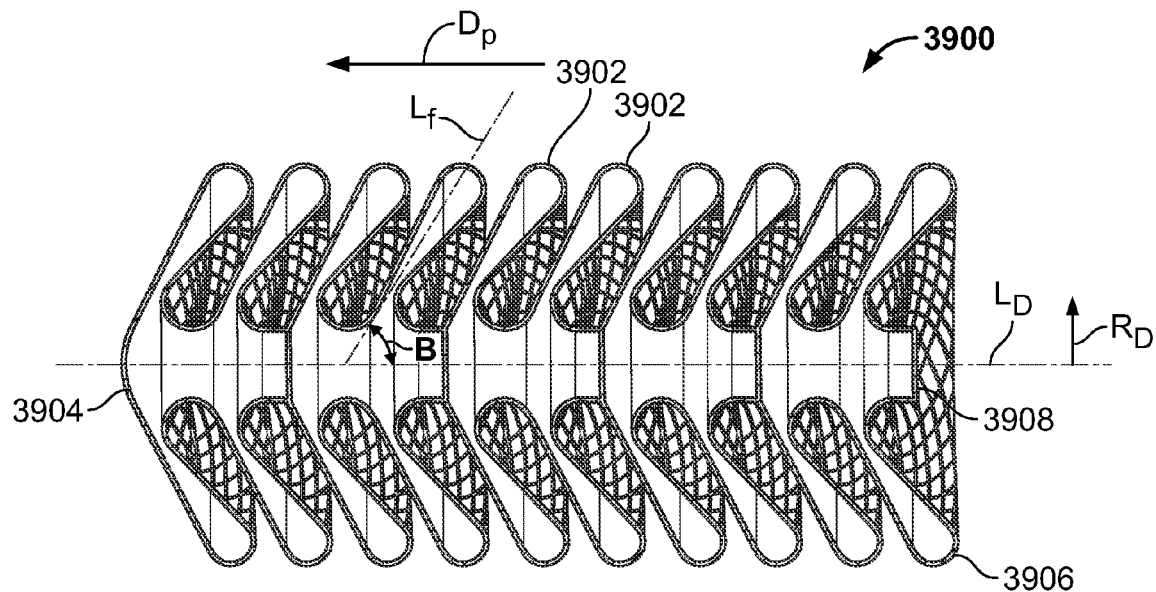
FIG. 40 is a partial sectional view of apparatus shown in FIG. 39.

FIG. 40 shows anchoring substrate 3900 in cross-section as viewed along lines 40-40 (shown in FIG. 39). When proximal end 3904 and distal end 3906 (e.g., at flange 3908) are displaced longitudinally toward each other, anchoring substrate 3900 may compress longitudinally and disc-like folds 3902 may expand in direction $R_D$. When proximal end 3904 and distal end 3906 (e.g., at flange 3908) are displaced longitudinally away from each other, anchoring substrate 3900 may extend longitudinally and disc-like folds 3902 may contract in direction $-R_D$.

The longitudinal extension may be used to deploy anchoring substrate in a radially compressed state. After deployment, anchoring substrate may be longitudinally compressed so that folds 3902 expand in radial direction $R_D$. Anchors may then be engaged with folds 3902. Anchoring substrate 3900 may then be longitudinally extended to apply radially inward force to the anchors. Tension in direction DP may then be applied to the anchors by pulling proximal end 3904. Folds 3902 may be biased at angle B in direction $-D_P$ so that when end 3904 is pulled, fold axes Lf are pre-aligned with the anchors.

Proximal portion 3904 may be attached to a pull member (not shown) that may be similar to a portion of a central axis member such as 124 (as shown in FIG. 1B). Distal end 3906, at flange 3908, may be attached to a portion of the device that remains substantially longitudinally stationary when the pull device pulls on proximal portion 3904. For example, flange 3908 may be fixed to the distal end of a corresponding support cage such as 105 (shown in FIG. 1).

Figure 41:
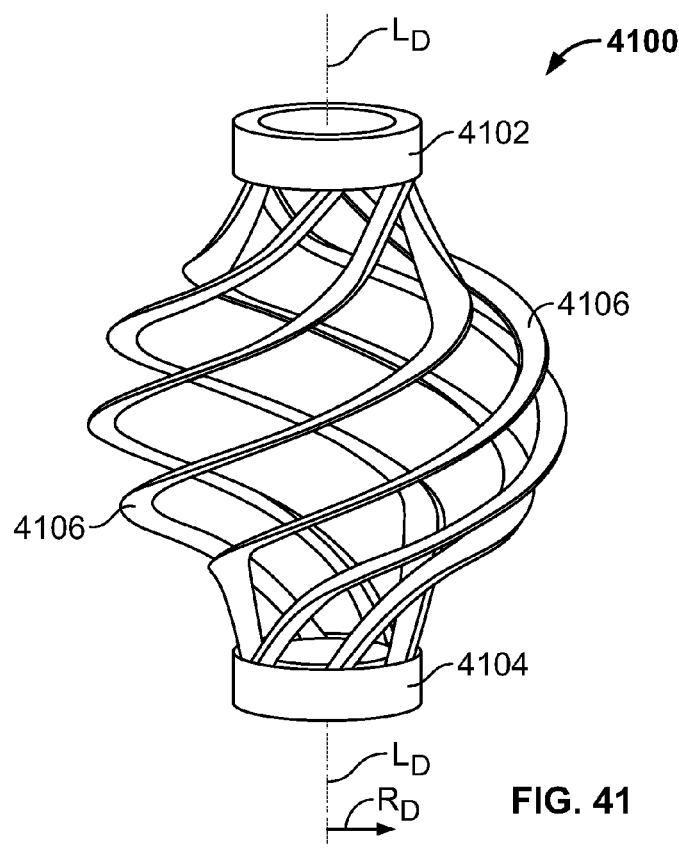
FIG. 41 is a perspective view of apparatus in accordance with the principles of the invention.

FIG. 41 shows illustrative support cage 4100 for a fracture repair device in accordance with the principles of the invention. Support cage 4100 may include hub 4102 and base ring 4104. Spiral support members 4106 extend between hub 4102 and base ring 4104. A central axis member (not shown) may extend along device axis $L_D$. The central axis member may have a distal end that is longitudinally fixed to hub 4102. The central axis member may extend through base ring 4104. Base ring 4104 may be moved along the central axis member. When base ring 4104 is moved away from hub 4102, spiral support members 4106 may extend longitudinally and straighten. As spiral support members 4106 straighten, ring 4104 may rotate.

Longitudinal extension of support cage 4100 may configure support cage 4100 for deployment. Longitudinal compression of support cage 4100 may configure support cage 4100 for deployment and engagement with bone segment anchors. In some embodiments, support cage 4100 may be expanded and collapsed by application of an external rotational force.

In some embodiments, support cage 4100 may be self-expanding. In those embodiments, support cage 4100 may have a relaxed state that is longitudinally compressed. Support cage 4100 may be longitudinally extended for deployment. Support cage 4100 may then return to its relaxed state after deployment.

Figure 42:
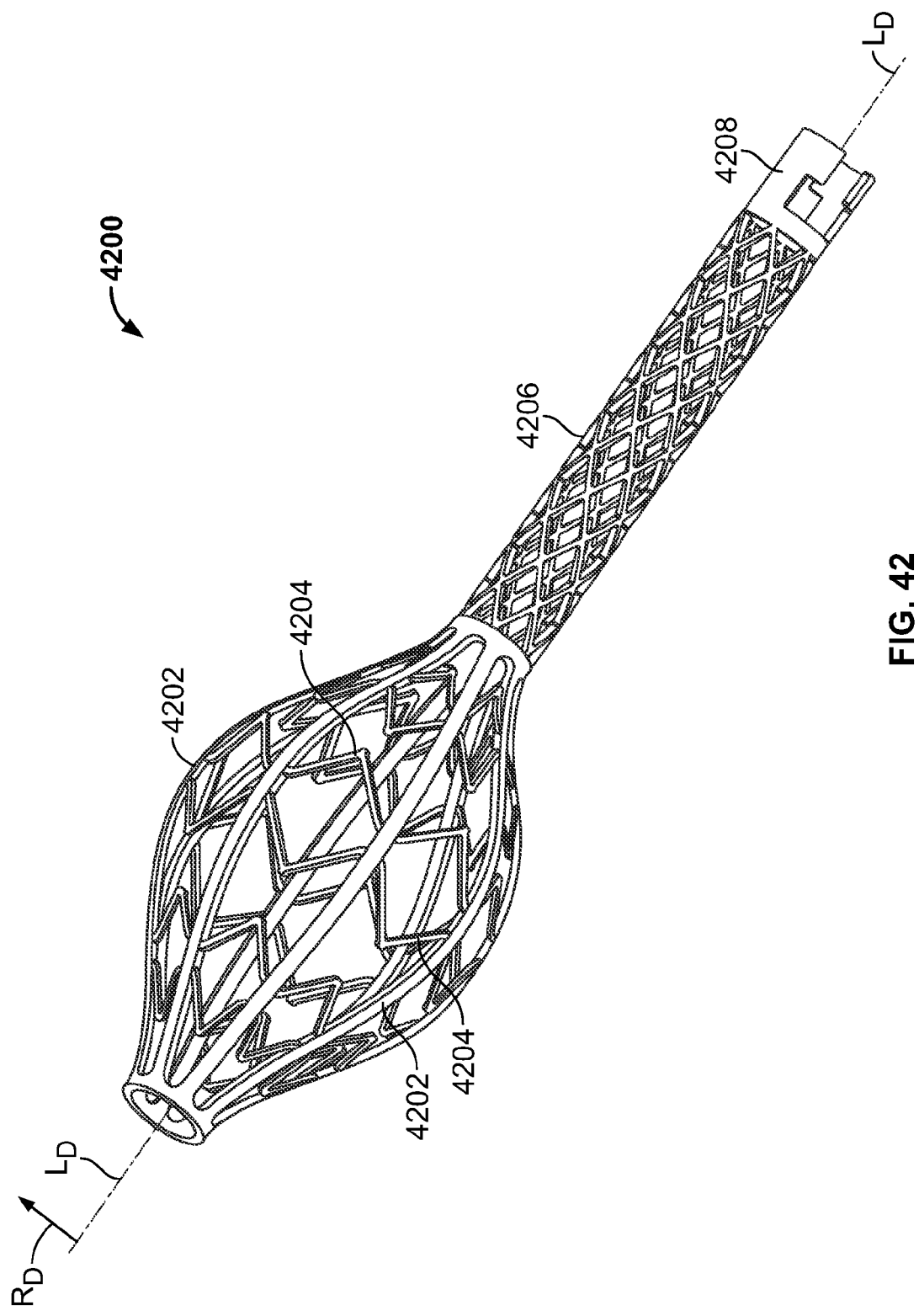
FIG. 42 is a perspective view of apparatus in accordance with the principles of the invention.

FIG. 42 shows illustrative hybrid support cage and anchoring substrate 4200. Hybrid cage/substrate 4200 may include support members 4202. Support members 4202 may support bone segments such as $P_a$, $P_h$ and $P_B$ (shown in FIG. 1). Hybrid cage/substrate 4200 may include substrate members 4204 for engaging anchors such as 114 and 116 (shown in FIG. 1). Substrate members 4204 may be supported by support members 4202. Substrate members 4204 and 4202 may expand and contract radially as a single unit.

Hybrid cage/substrate 4200 may include stem 4206 and device retention member 4208. Support members 4202 may be integrated with substrate members 4204 in a single-layer structure. Substrate members 4204 may have features that are described herein in connection with anchoring substrates such as 112 (shown in FIG. 1). For example, the substrate members 4204 may be formed to facilitate anchor mating and retention. Hybrid cage/substrate 4200 may be used alone or in concert with layers of other hybrid cage/substrates like 4200 or with layers of other constructs such as devices previously described herein like central axis member 2502 (shown in FIG. 25), intermediate member 2507 (shown in FIG. 25), anchoring member 3300 (shown in FIG. 33) and outer member 2514 (shown in FIG. 25).

Figure 43:
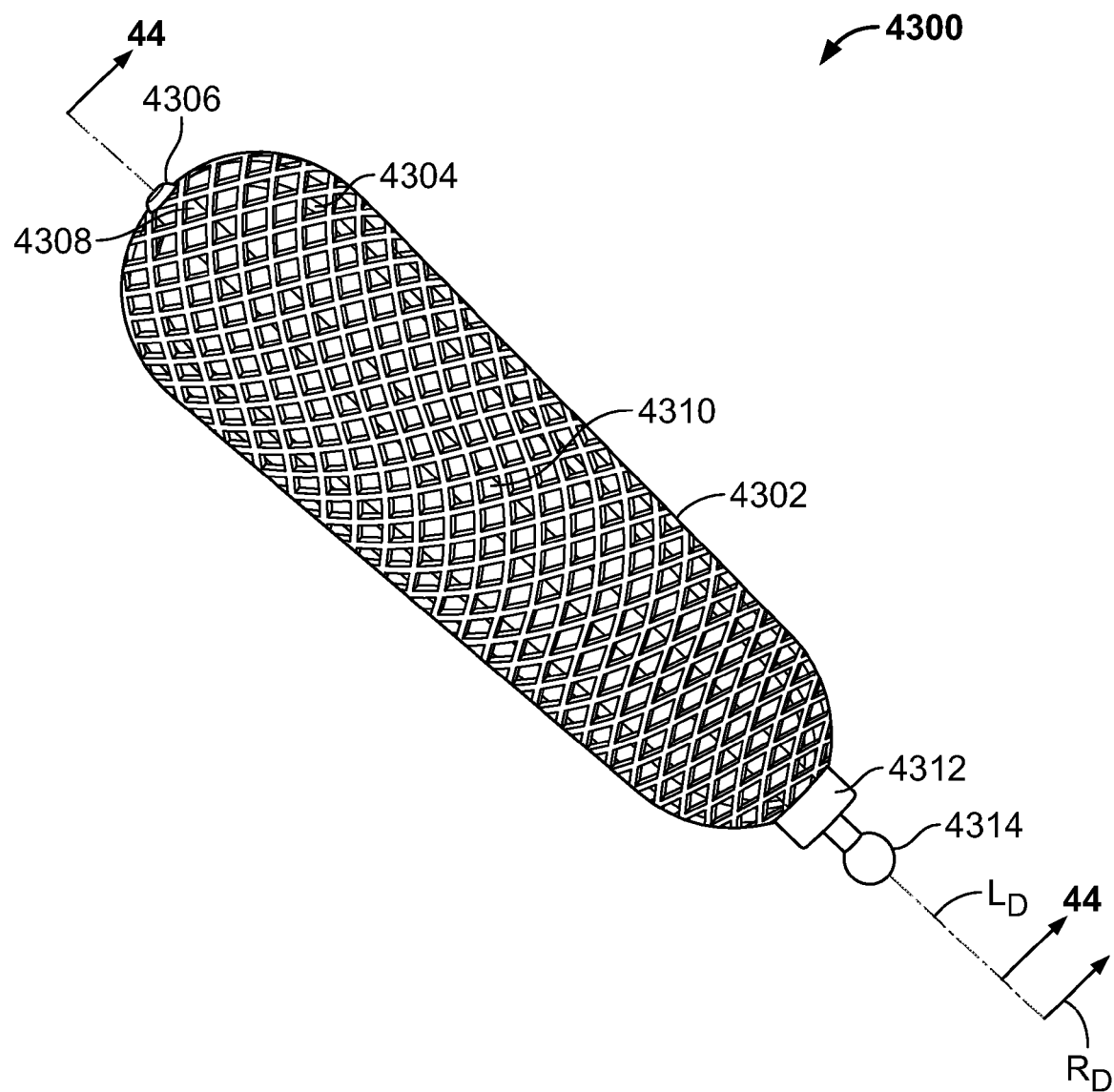
FIG. 43 is a perspective view of apparatus in accordance with the principles of the invention.

FIG. 43 shows illustrative fracture repair device 4300 in accordance with the principles of the invention. Device 4300 includes anchoring substrate 4302 and support cage 4304. Anchoring substrate 4302 is radially outside support cage 4304. Device 4300 may include distal hub 4306. Distal hub 4306 may provide support for proximal end 4308 of central axis member 4310. Proximal base 4312 may support proximal portions of anchoring substrate 4302 and support cage 4304. Central axis member 4310 may pass through proximal base 4312. Central axis member 4310 may support device retention member 4314.

Figure 44:
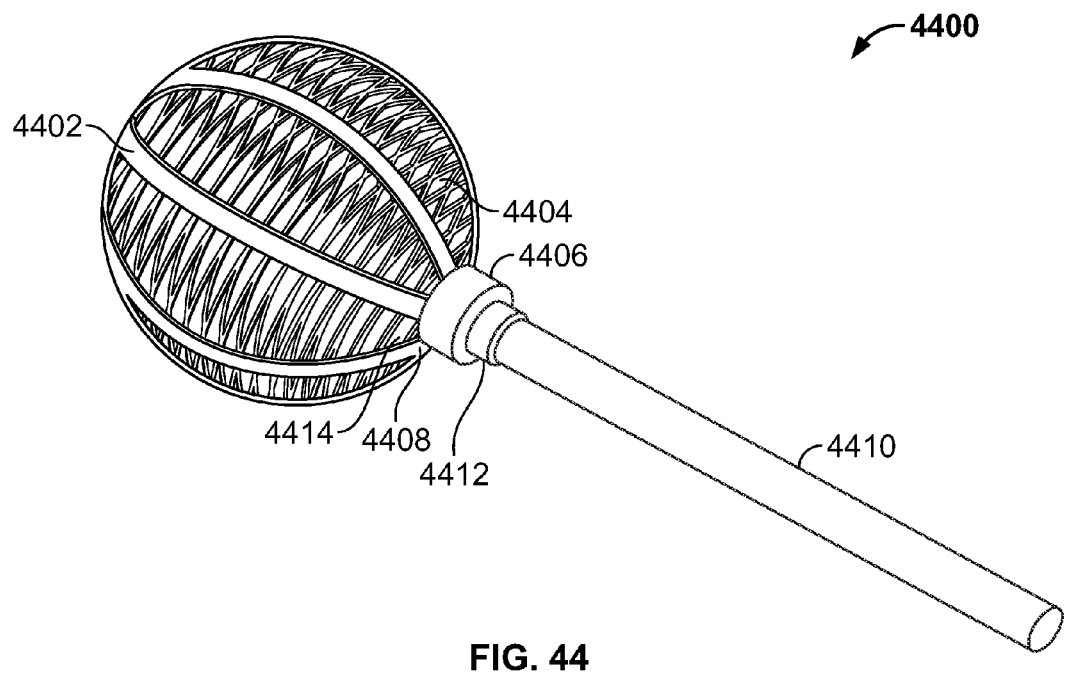
FIG. 44 is a perspective view of apparatus in accordance with the principles of the invention.

FIG. 44 shows illustrative fracture repair device 4400 in accordance with the principles of the invention. Device 4400 may include structural cage 4402 and anchoring substrate 4404. Device 4400 may include bushing 4406 for sliding proximal portion 4408 of structural cage 4402 along central axis member 4410. Device 4400 may include bushing 4412 for sliding proximal portion 4414 of anchoring substrate 4404 along central axis member 4410. The bushings may support device retention members such as 1802 (shown in FIG. 18). The device retention members may be used to expand and contract device 4400. Spherical or sphere-like embodiments of device 440 may provide a high radial compression strength, and generate high radial compression forces, based on the shape.

Figure 45:
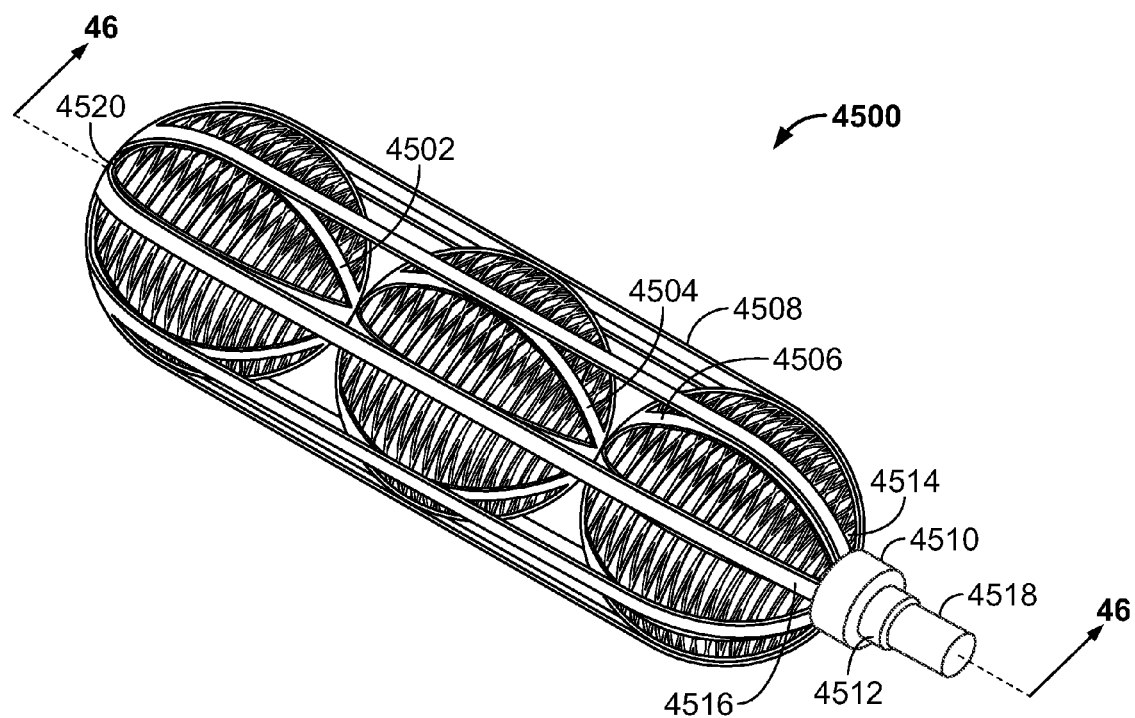
FIG. 45 is a perspective view of apparatus in accordance with the principles of the invention.

FIG. 45 shows illustrative fracture repair device 4500 in accordance with the principles of the invention. Device 4500 may include a train of substantially spherical or sphere-like structural cages 4502, 4504 and 4506 inside outer structural cage 4508. Device 4500 may include as many cages as desired to make a train of a desired length. In some embodiments, an anchoring substrate like 4300 (shown in FIG. 43) may be present. The anchoring substrate may be present within or outside of structural cage 4508.

In some embodiments, the cages may be partially spherical. An anchoring substrate is present inside each of the structural cages. Device 4500 may include bushings 4510 and 4512 for positioning proximal end 4516 of outer structural cage 4508 and proximal end 4514 of the train, respectively, along central axis member 4518. Central axis member 4518 may be rigidly fixed at outer structural cage hub 4520. Structural cages 4502, 4504 and 4506, outer structural cage 4508 and the anchoring substrates may be expanded and collapsed by sliding bushings 4510 and 4512 along central axis member 4518.

Figure 46:
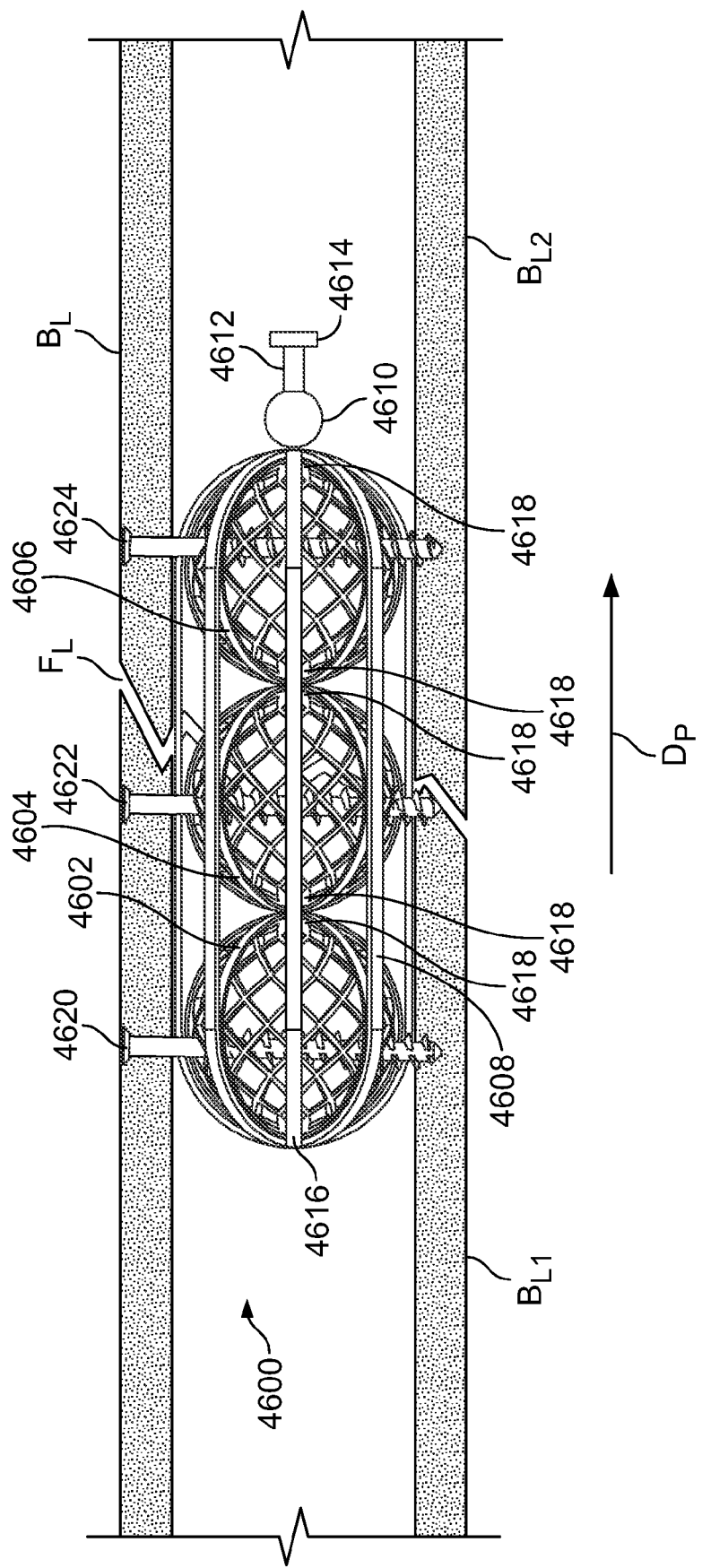
FIG. 46 is a side view of apparatus in accordance with the principles of the invention inside a body portion.

FIG. 46 shows illustrative fracture repair device 4600 in accordance with the principles of the invention. Device 4600 is shown in long bone $B_L$ in a view that is similar to the view of device 4500 along lines 46-46 that is shown in FIG. 45. Device 4600 may include a train of substantially spherical structural cages 4602, 4604 and 4606 inside outer structural cage 4608. Device 4600 may transect fracture $F_L$.

An anchoring substrate may be present inside each of structural cages 4602, 4604 and 4606. Device 4600 may include device retention member 4610. Device retention member 4610 may be configured to slide relative to central axis member 4612. Central axis member 4612 may terminate proximally at device recapture member 4614. Central axis member 4612 may terminate distally at outer structural cage hub 4616, to which central axis member 4612 may be rigidly fixed.

Structural cages 4602, 4604 and 4606, outer structural cage 4608 and the anchoring substrates may be expanded and collapsed by sliding device retention member 4610 relative to device recapture member 4614. Ratcheted bushings 4618 may be present to retain device 4600 in an expanded state. After device 4600 is expanded, anchors 4620, 4622 and 4624 may be inserted through bone segments $B_{L1}$ and $B_{L2}$ to engage the anchoring substrates.

A compressive traction may be applied to fracture FL by initially inserting anchors 4620 and 4622, drawing device 4600 in proximal direction $D_P$ relative to bone segment $B_{L2}$, and subsequently inserting anchor 4624.

Figure 47:
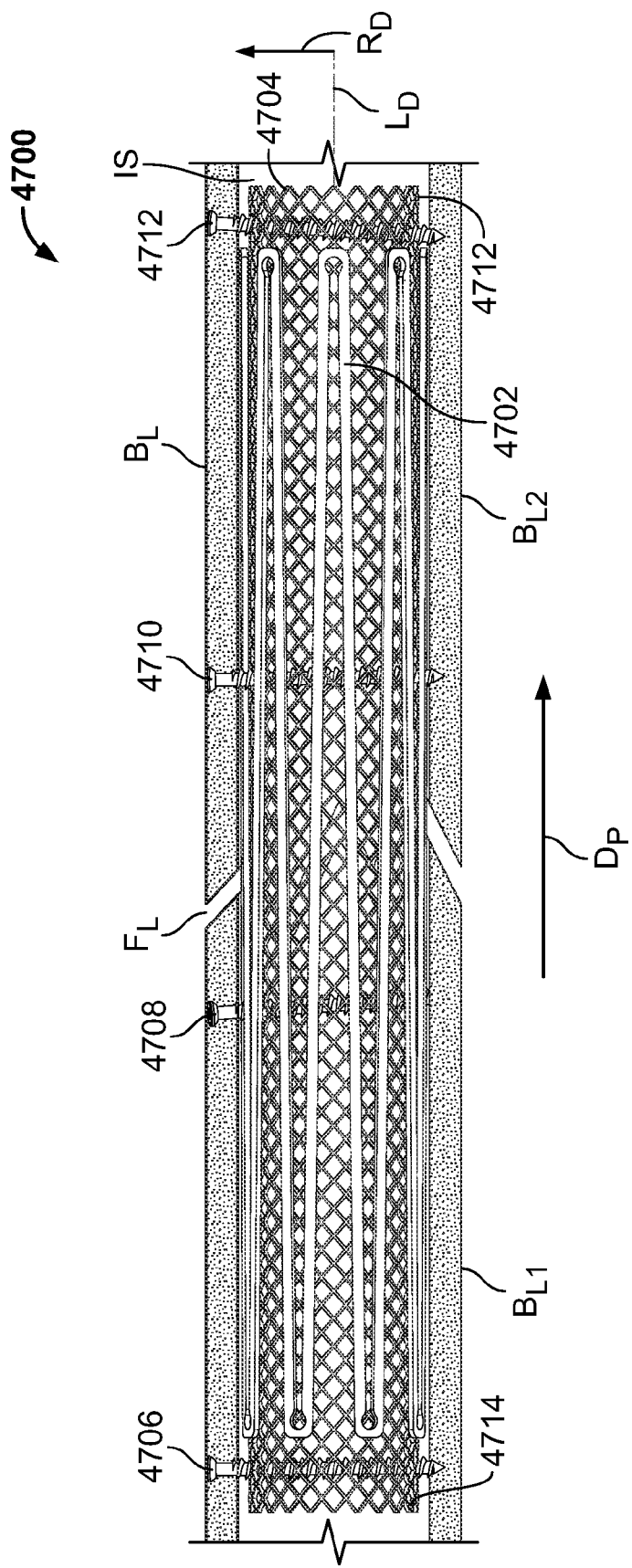
FIG. 47 is a side view of apparatus in accordance with the principles of the invention inside a body portion.

FIG. 47 shows illustrative fracture repair device 4700 in accordance with the principles of the invention. Device 47 is shown deployed in intramedullary space IS of long bone $B_L$. Device 47 bridges across fracture $F_L$. Device 47 may include structural cage 4702. Device 47 may include anchoring substrate 4704. Structural cage 4072 may be deployed in intramedullary space IS. Structural cage 4072 may provide radially outward support to bone segments $B_{L1}$ and $B_{L2}$. Anchoring substrate 4704 may be deployed within structural cage 4072.

Anchoring substrate 4704 may be engaged by anchors 4706, 4708, 4710 and 4712 to stabilize bone segments $B_{L1}$ and $B_{L2}$ against structural cage 4702. A compressive traction may be applied to fracture FL by initially inserting anchors 4706 and 4708, drawing device 4700 in proximal direction DP relative to bone segment $B_{L2}$, and subsequently inserting anchors 4710 and 4712.

Device 4700 is shown with substantially open ends. In some embodiments, device 4700 may have ends that terminate at a hub or a base, such as are shown and described herein. Device 4700 may be used as shown or in conjunction with other devices that are shown and described herein.

Figure 48:
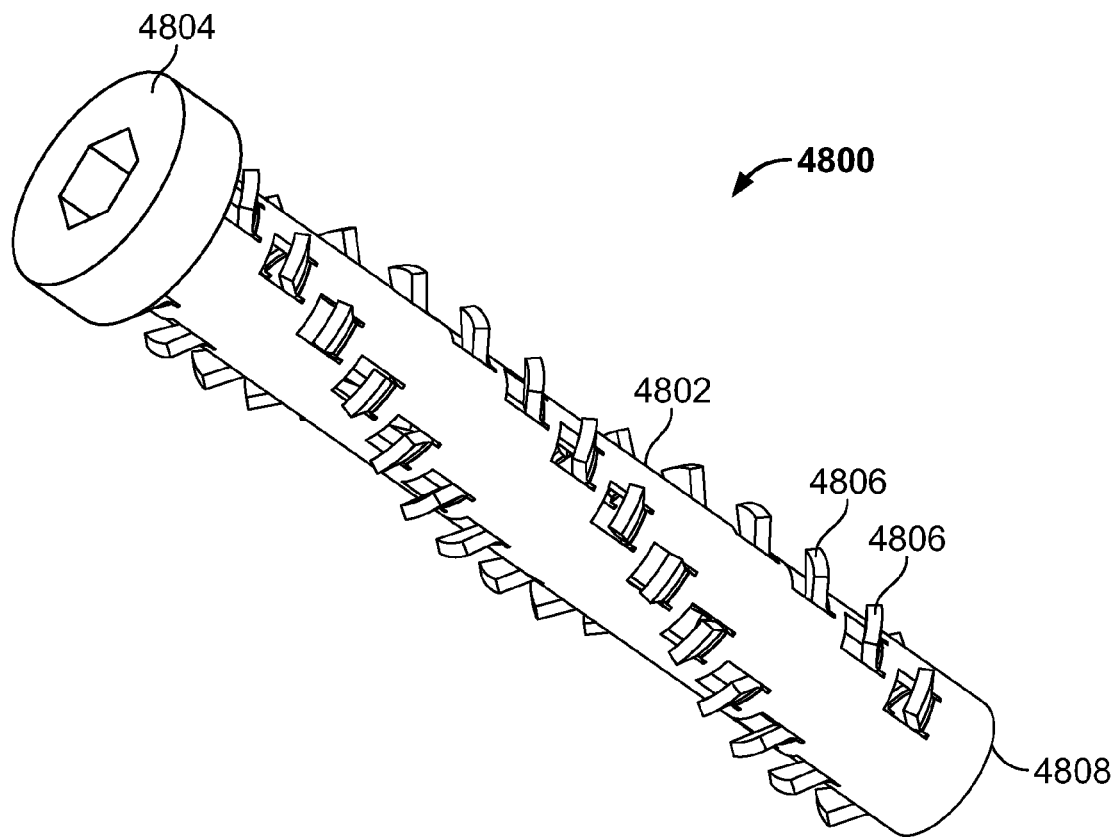
FIG. 48 is a perspective view of apparatus in accordance with the principles of the invention.

FIG. 48 shows illustrative anchor 4800 that may be used with a fracture repair device in accordance with the principles of the invention. Anchor 4800 may include elongated member 4802, head 4804 and tabs 4806. Anchor 4800 may be deployed using torque, axial pressure or both. Elongated member 4802 may be inserted through a bone segment. Tabs 4806 may be elastically deformable so that when anchor 4800 is inserted through the bone segment, tabs 4806 lie substantially even with the outer surface of elongated member 4802.

End 4808 may pass through a cell in an anchoring substrate such as 112 (shown in FIG. 1). One or more of tabs 4806 may engage the anchoring substrate and prevent anchor 4800 from being disengaged from the anchoring substrate. Tabs 4806 may deflect to lie substantially even with the outer surface of elongated member 4802 when anchor 4800 penetrates the anchoring substrate.

In some embodiments, tabs 4806 may have a predeployment state in which tabs 4806 may lie substantially even with the outer surface of elongated member 4802. Tabs 4806 may be deployed after anchor 4800 is inserted through the bone and the anchoring substrate. Tabs 4806 may be deployed by inserting an actuator shaft (not shown) in the lumen of elongated member 4802. The actuator shaft may push tabs 4806 radially outward.

Tabs 4806 may include an extensions (not shown) that extend into the lumen of anchor 4800. The extensions may be extend away from the "plane" of the tabs. The extensions may facilitate the deployment of the tabs when the actuator shaft is driven down the lumen and contacts the extensions.

Elongated member 4802 may be constructed from tube stock. Tabs 4806 may be punched or laser cut from the tube. Head 4804 may be welded to elongated member 4802. Head 4804 may include driver receptacle 4804. The diameter of the tube stock may be selected to correspond to that of the anchoring substrate cells to maximize the interference (and between tabs 4806 and the anchoring substrate. Such selection may provide suitable retention of the anchors.

Figure 49:
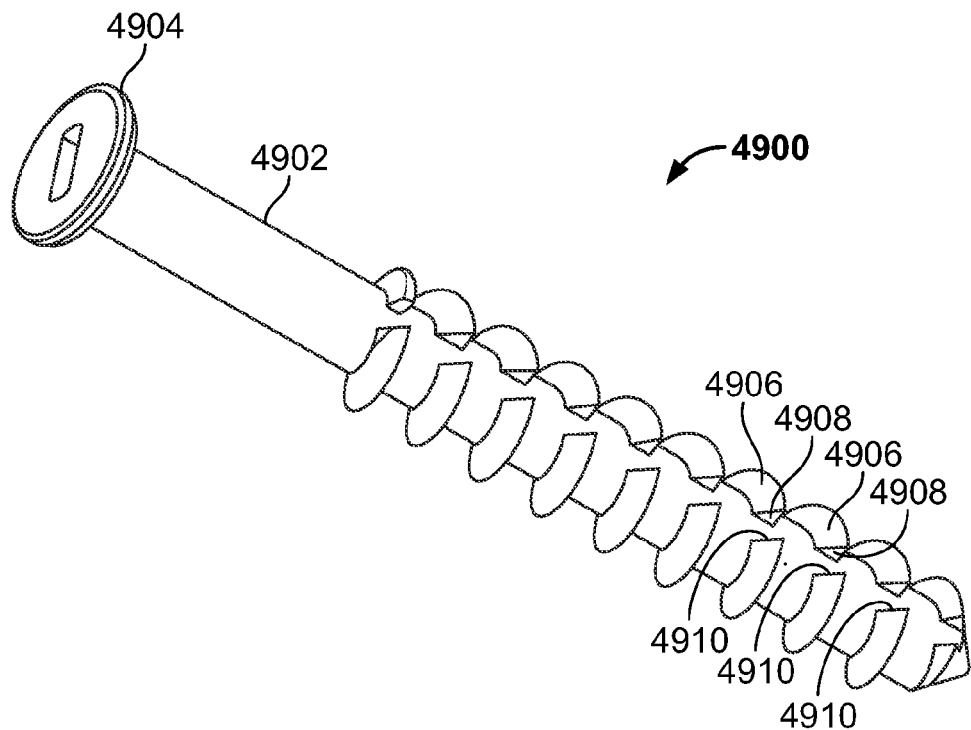
FIG. 49 is a perspective view of apparatus in accordance with the principles of the invention.

FIG. 49 shows illustrative anchor 4900 that may be used with a fracture repair device in accordance with the principles of the invention. Anchor 4900 may include elongated member 4902, head 4904 and thread segments 4906. Anchor 4900 may be deployed using torque, axial pressure or both. Elongated member 4902 may be inserted through a bone segment. Thread segments 4906 may be elastically deformable to ease insertion in the bone segment and engagement with the anchoring substrate. Parameters of thread segments 4906 may be selected for engagement with an anchoring substrate. The parameters may include minor diameter, major diameter, pitch and any other suitable parameters.

Thread segments 4906 may include circumferential faces 4908 and corresponding circumferential locking faces 4910. Circumferential locking faces 4910 may catch in the anchoring substrate and prevent anchor 4900 from unscrewing from the anchoring substrate.

Figure 50:
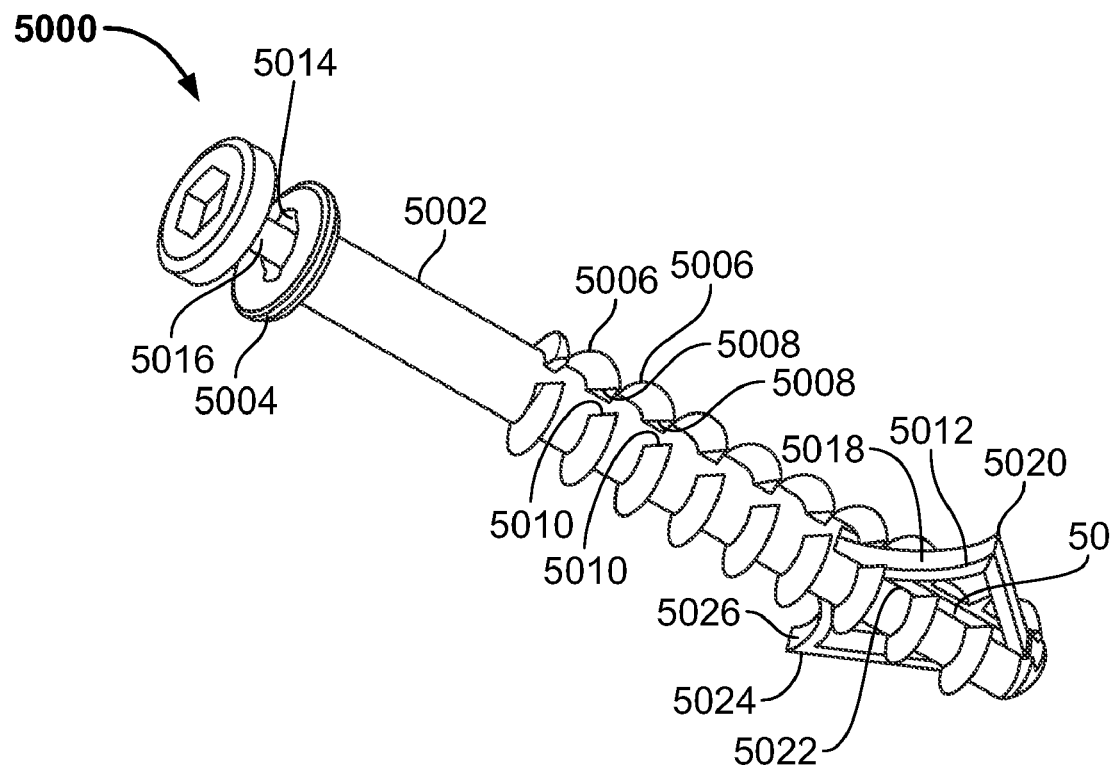
FIG. 50 is a perspective view of apparatus in accordance with the principles of the invention.

FIG. 50 shows illustrative anchor 5000 that may be used with a fracture repair device in accordance with the principles of the invention. Anchor 5000 may include elongated member 5002, head 5004 and thread segments 5006. Thread segments 5006 may have some or all of the features of thread segments 4906 (shown in FIG. 49). For example, thread segments 5006 may include circumferential faces 5008 and corresponding circumferential locking faces 5010. Circumferential locking faces 5010 may catch in the anchoring substrate and prevent anchor 5000 from unscrewing from the anchoring substrate.

Anchor 5000 may be deployed using torque, axial pressure or both.

Anchor 5000 may include articulating catch 5012. Articulating catch 5012 may in a non-deployed state be present in lumen 5014 of elongated member 5002. Rod 5014 may be depressed in lumen 5014 and may push on leg 5018 of catch 5012. Leg 5018 may urge hinge 5020 out of port 5022 in elongated member 5002. Corresponding catch 5024 may be deployed in a similar fashion. Legs 5018 and 5026 may catch in the anchoring substrate after deployment of catches 5012 and 5024. Anchor 5000 may thus be locked to the anchoring substrate.

Figure 51:
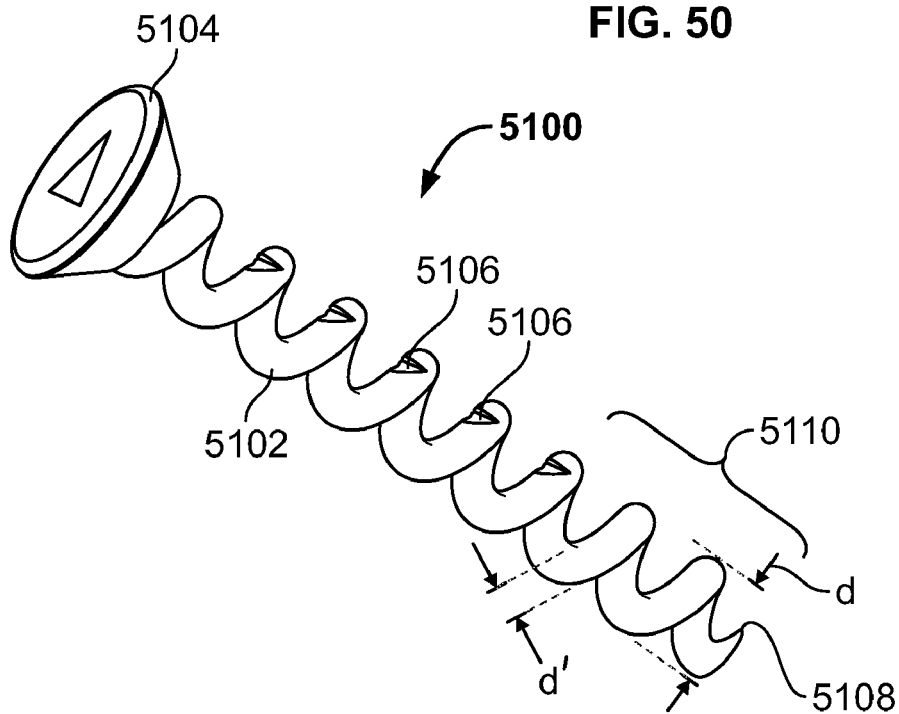
FIG. 51 is a perspective view of apparatus in accordance with the principles of the invention.

FIG. 51 shows illustrative anchor 5100 that may be used with a fracture repair device in accordance with the principles of the invention. Anchor 5100 may include spiral member 5102, head 5104 and notches 5106. Anchor 5100 may be deployed using torque, axial pressure or both.

Elongated member 5102 may be inserted through a bone segment. A pilot hole in the bone segment may have a diameter corresponding to diameter d of spiral member 5102. Spiral member 5102 may thus pass through the bone segment without substantial rotation. In some embodiments, an anchor access hole in the bone could be made for anchor 5100. The anchor access hole may have a diameter that is no smaller than diameter d' of elongated member 5102 and is large enough to allow elongated member 5102 to be helically threaded thru the hole. Such an access hole may be smaller than a standard anchor hole.

Tip 5108 may then engage the anchoring substrate. Rotation of anchor 5100 may then drive anchor 5100 relatively deeper into the anchoring substrate. Notches 5106 may catch in the anchoring substrate and prevent anchor 5100 from rotating out of engagement with the anchoring substrate. End portion 5110 may be provided without notches so that anchor 5100 may be backed out of the anchoring substrate, if desired, before driving anchor 5100 into a locked relationship with the anchoring substrate.

Figure 52:
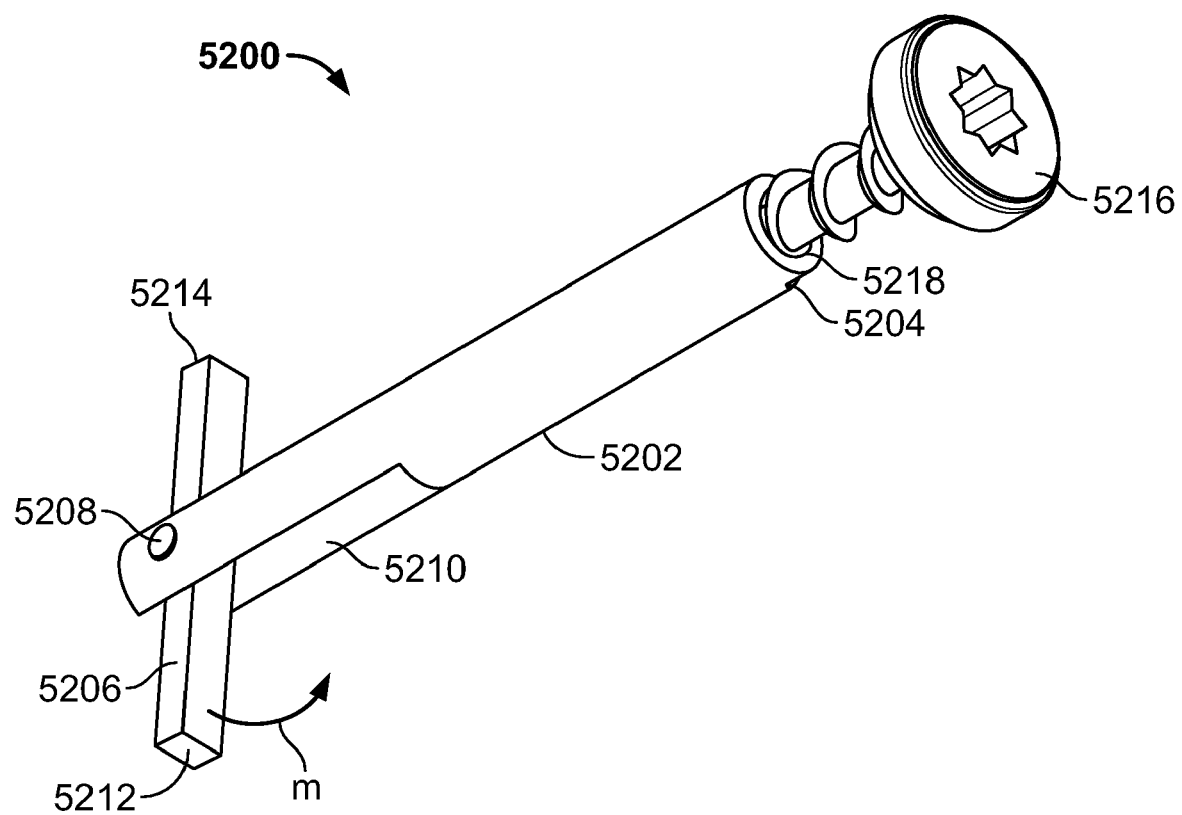
FIG. 52 is a perspective view of apparatus in accordance with the principles of the invention.

FIG. 52 shows illustrative anchor 5200 that may be used with a fracture repair device in accordance with the principles of the invention. Anchor 5200 may include elongated member 5202, head 5204 and catch 5206. Catch 5206 may be supported by and rotatable about pin 5208. Catch 5206 may in a nondeployed state be present or partially present in slot 5210 in elongated member 5202. For example, catch 5206 may rotate in direction m such that tip 5212 rotates into slot 5210 and tip 5214 rotates into a position that extends beyond elongated member 5202.

In such a configuration, elongated member 5202 may be inserted through a bone segment. Tip 5214 may then traverse a portion of the anchoring substrate. After the traverse, tip 5214 may rotate in the −m direction such that anchor 5200 returns to the configuration shown in FIG. 52. The span of catch 5206 may exceed the diameter of a cell in the anchoring substrate. Anchor 5200 may thus be locked to the anchoring substrate.

In some embodiments, screw-actuator 5216 may be present in bore 5218 of elongated member 5202. Screw-actuator 5216 may be screwed into the bore. This action may reduce the effective length of anchor 5200 and, therefore tension the bone segment to the anchor substrate. In some embodiments, a tip (not shown) of screw-actuator 5216 may deflect tip 5212 out of slot 5210 to rotate catch 5206. Tip 5212 may be beveled to facilitate deflection by the tip of screw-actuator 5216.

Figure 53:
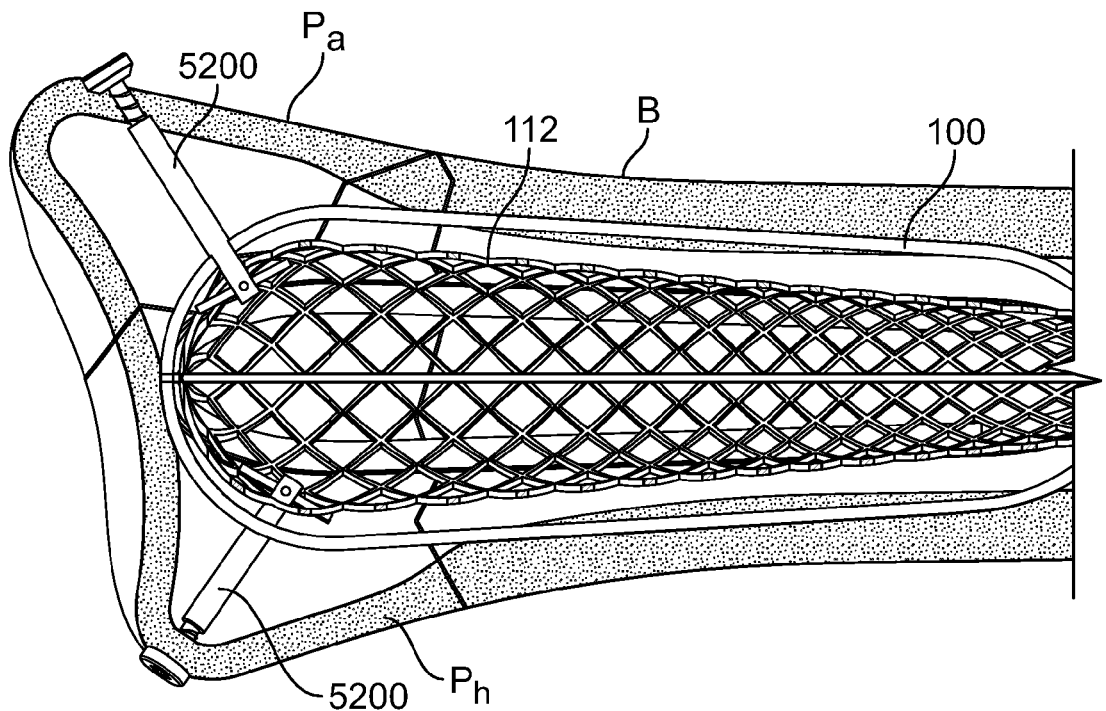
FIG. 53 is a side view of apparatus in accordance with the principles of the invention inside a body portion.

FIG. 53 shows anchors 5200 deployed and locked into anchoring substrate 112 of device 100 (shown also in FIG. 1). Anchors 5200 thus fasten bone segments Pa and Ph to anchoring substrate 112.

Figure 54:
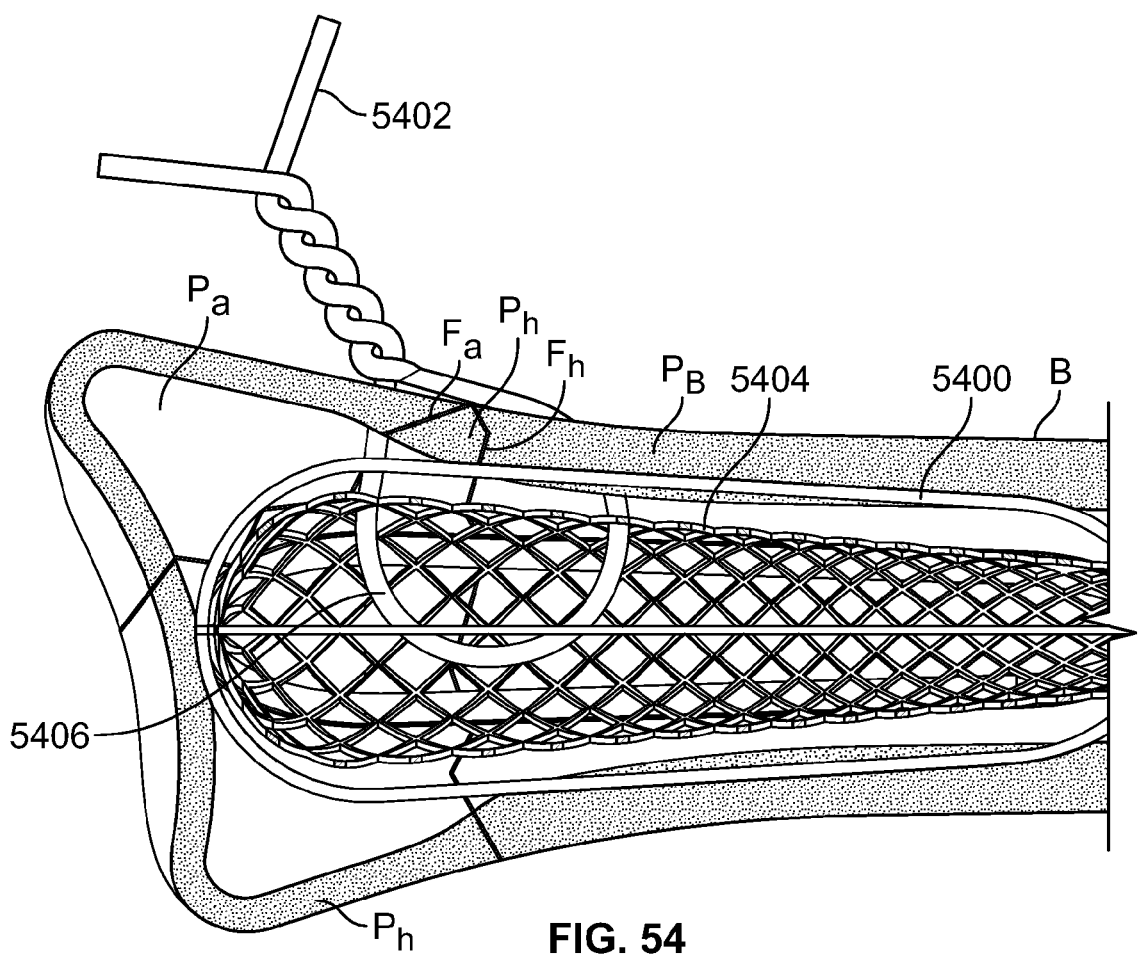
FIG. 54 is a side view of apparatus in accordance with the principles of the invention inside a body portion.

FIG. 54 shows illustrative fracture repair device 5400 in accordance with the principles of the invention. Device 5400 is implanted in bone B. Wire 5402 passes through holes that are drilled through bone segment $P_a$, anchoring substrate 5404 and bone segment PB to form loop 5406. The ends of wire 5402 may be fastened to each other to secure bone portions $P_a$, $P_h$ and $P_B$ to each other.

Figure 55:
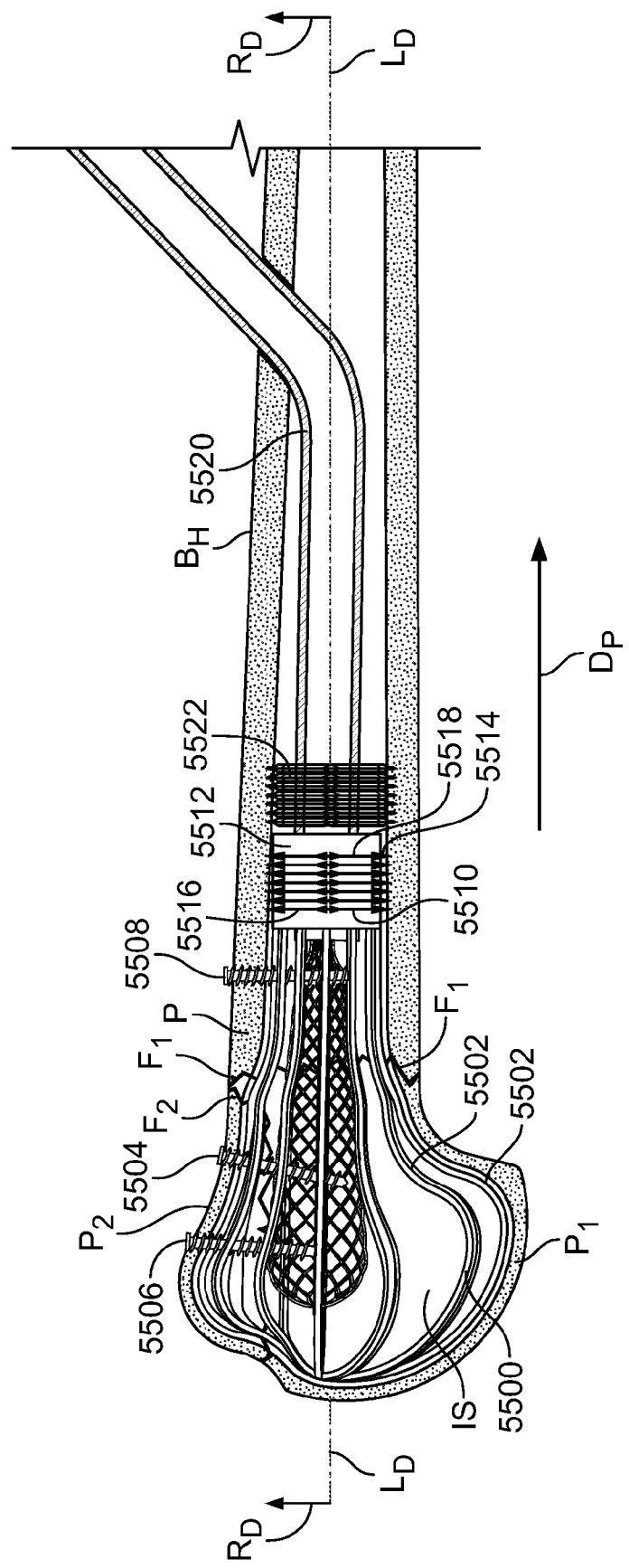
FIG. 55 is a side view of apparatus in accordance with the principles of the invention inside a body portion.

FIG. 55 shows illustrative fracture repair device 5500 in accordance with the principles of the invention. Device 5500 is shown deployed and locked in humerus $B_H$. Support members 5502 generally conform to the contours of intramedullary space IS in bone $B_H$. Anchoring substrate applies tension in direction $D_P$ to anchors 5504 and 5506. Proximal anchor 5508 retains the tension.

Expanding cylindrical anchor 5510 is present coaxially about structural cage base 5512. Anchor 5510 may expand radially when compressed along axis $L_D$. When anchor 5510 expands, circumferential blades 5514 extend radially into bone $B_H$. Anchor 5510 may be compressed by longitudinally fixing distal end 5516 at a position on structural cage base 5512 and pushing distally on proximal end 5518. A detent (not shown) may be provided to prevent anchor 5510 from extending longitudinally. When locked in the compressed state, anchor 5510 cuts into bone $B_H$ and locks device 5500, or parts thereof, longitudinally. Anchor 5510 may be self-expanding when released from constraint. Anchor 5510 may be rotated during expansion to promote engagement with the bone.

Expanding cylindrical anchor 5522 is shown connected directly to anchoring substrate 5530. Anchor 5522 may be locked after a desired tension is obtained in device 5500. Expanding cylindrical anchor 5522 may have some or all of the features of expanding cylindrical anchor 5510.

Figure 56A:
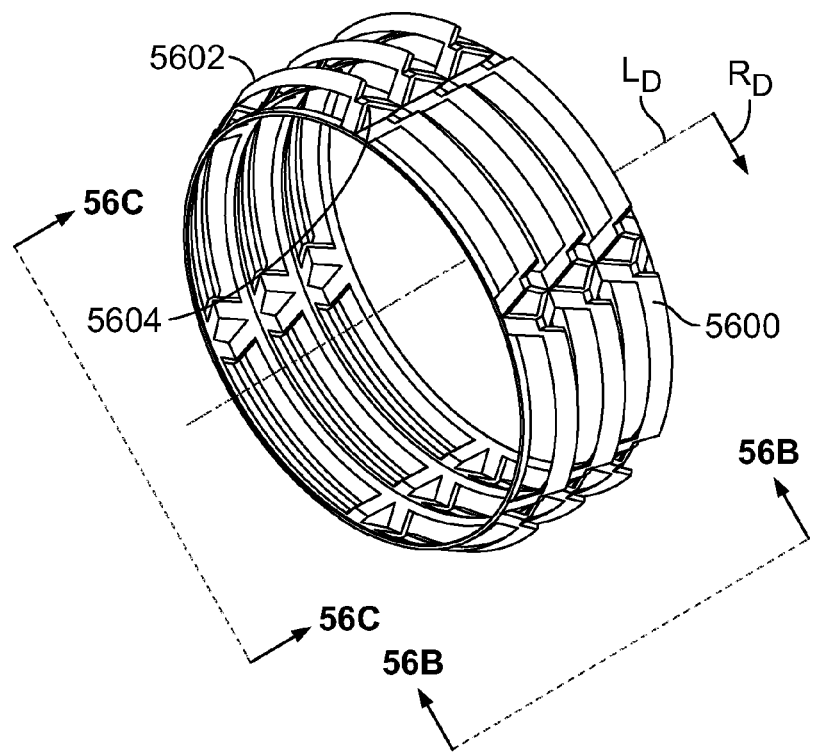
FIG. 56A is a perspective view of apparatus in accordance with the principles of the invention.

FIG. 56A shows illustrative expanding anchor 5600 that may be used in accordance with the principles of the invention. Anchor 5600 may have some or all of the features of anchor 5510 (shown in FIG. 55). Anchor 5600 may be cut from a tube. Compression along axis $L_D$ causes articulation of living hinge 5604. The articulation causes blades 5602 to extend radially away from axis $L_D$. Anchor 5600 may be self-expanding.

Figure 56B:
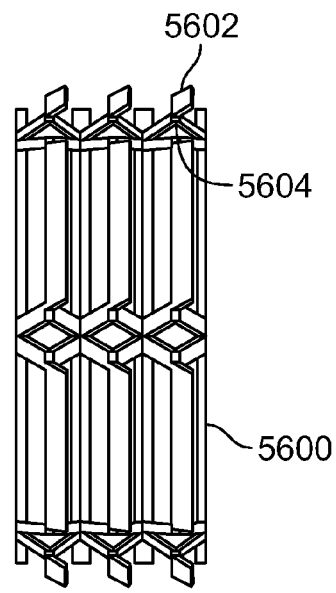
FIG. 56B is a side view of the apparatus shown in FIG. 56A.
Figure 56C:
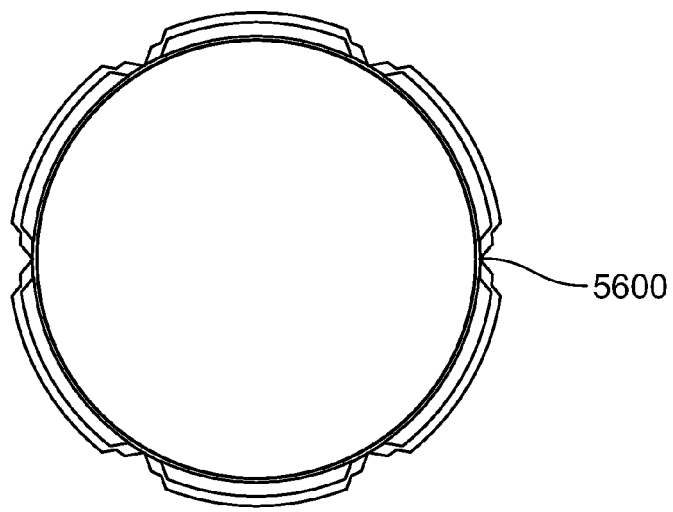
FIG. 56C is an end view of the apparatus shown in FIG. 56A.

FIG. 56B shows a view of anchor 5600 from direction 56B-56B (shown in FIG. 56A). FIG. 56C shows a view of anchor 5600 from direction 56C-56C (shown in FIG. 56A).

Figure 57A:
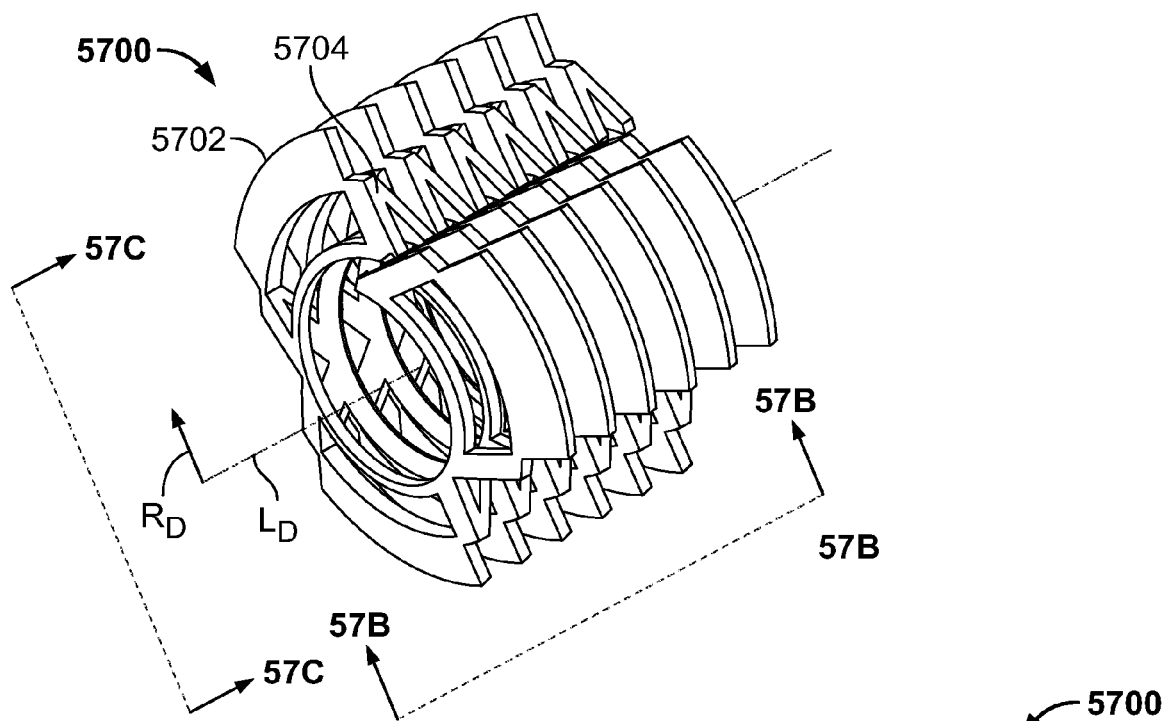
FIG. 57A is a perspective view of apparatus in accordance with the principles of the invention.

FIG. 57A shows illustrative expanding helical anchor 5700 that may be used in accordance with the principles of the invention. Helical anchor 5700 may have some or all of the features of anchor 5510 (shown in FIG. 55). Anchor 5700 may be cut from a tube. Compression along axis $L_D$ causes articulation of living hinge 5704. The articulation causes blades 5702 to extend radially away from axis $L_D$. Anchor 5700 may be self-expanding.

Figure 57B:
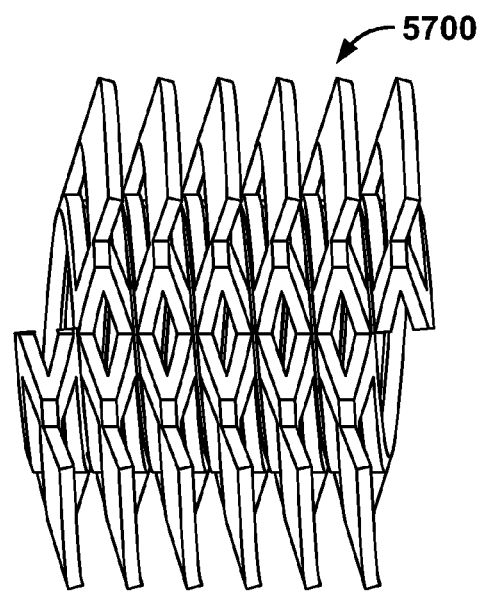
FIG. 57B is a side view of the apparatus shown in FIG. 57A.
Figure 57C:
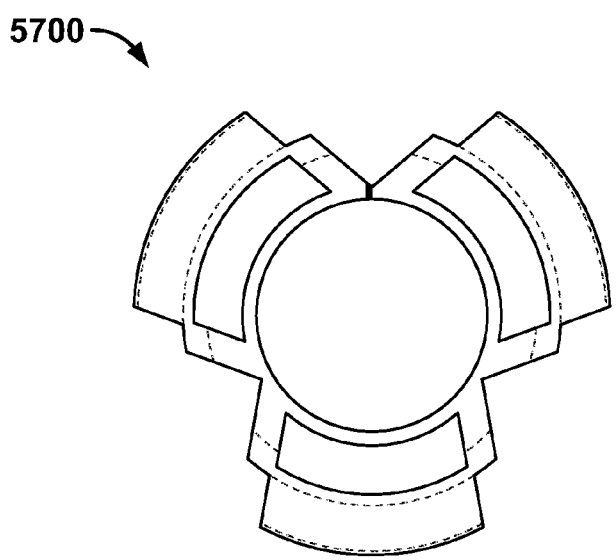
FIG. 57C is an end view of the apparatus shown in FIG. 57A.

FIG. 57B shows a view of anchor 5700 from direction 57B-57B (shown in FIG. 57A). FIG. 57C shows a view of anchor 5700 from direction 57C-57C (shown in FIG. 56A).

When helical anchor 5700 is rotated relative to surrounding bone, it may move like a screw because of the helical form of blades 5702. When helical anchor 5700 is rotated compressed and rotated simultaneously, blades 5702 may carve out bone material while anchor 5700 is being engaged in the bone. Carving out the bone material may reduce hoop stress in the bone.

Figure 58:
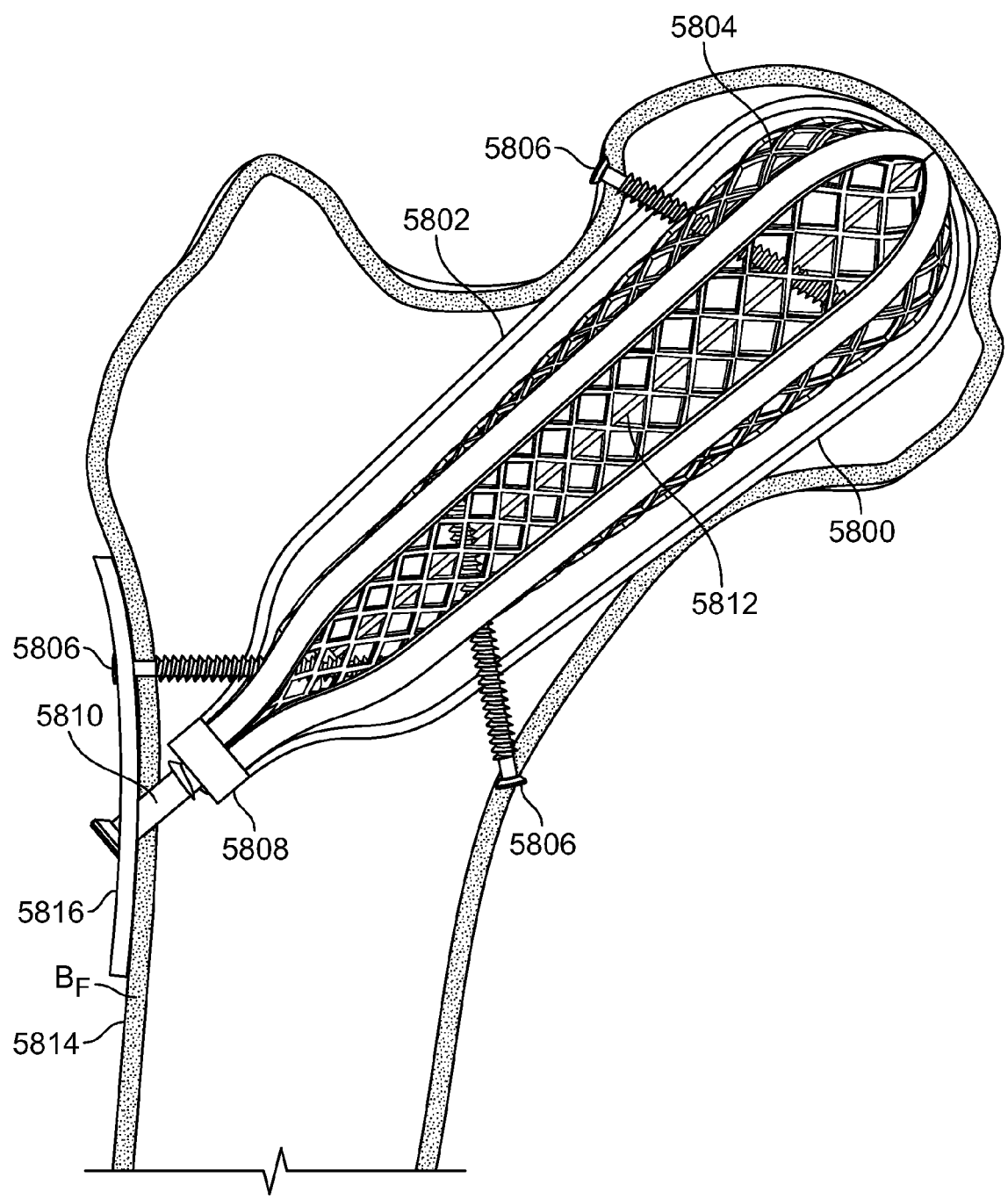
FIG. 58 is a side view of apparatus in accordance with the principles of the invention inside a body portion.

FIG. 58 shows illustrative bone fracture repair device 5800 in accordance with the principles of the invention in femur BF. Device 5800 includes structural cage 5802 and anchoring substrate 5804. Anchors 5806 fasten portions (individual bone segments not shown) of femur $B_F$ to anchoring substrate 5804. Structural cage 5800 may include cage base 5808 which may be configured to receive proximal anchor 5810. Proximal anchor 5810 may apply tension to central axis member 5812. Proximal anchor 5810 may apply tension to anchoring substrate 5804.

Device 5800 may be introduced at a site near point on bone $B_F$ so that device 5800 may be delivered in an orientation and at a position that is close to the desired deployed orientation and position.

Buttress plate 5816 may be present adjacent bone BF. Buttress plate 5816 may provide stability to anchors an 5814. Buttress plate 5816 may distribute forces from anchors 5806 and 5814 to different portions of bone $B_F$. Buttress plate 5816 may accommodate as many anchors 5806 as appropriate to secure the fracture. Buttress plate 5816 may have specially constructed mating features to lock device at a desired angle with respect to buttress plate 5816.

Figure 59:
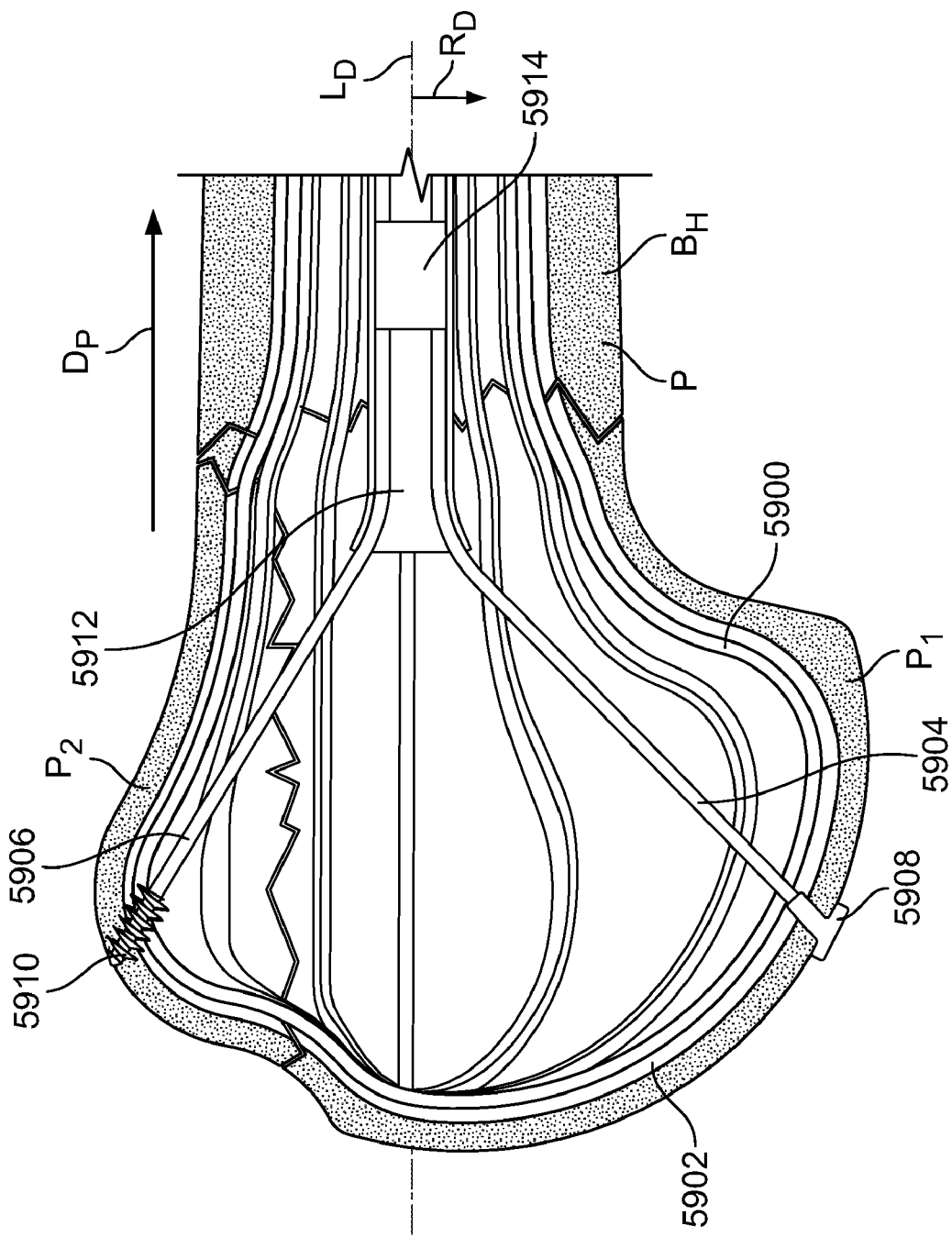
FIG. 59 is a side view of apparatus in accordance with the principles of the invention inside a body portion.

FIG. 59 shows illustrative bone fracture repair device 5900 in accordance with the principles of the invention in humerus $B_H$. In some embodiments, device 5900 may be completely delivered and deployed through a single access hole (not shown). Device 5900 includes structural cage 5902. Structural cage 5902 may provide outward radial and longitudinal support for bone segments P, $P_1$ and $P_2$.

Anchors may be delivered by steerable catheter into bone BH and through a cage base such as 108 (shown in FIG. 1). Tethers 5904 and 5906 may apply inward radial and proximal tension to bone segments $P_1$ and $P_2$, respectively. The tethers may be delivered into humerus BH through an access hole (not shown) that is proximal device 5900. Device may not include an anchoring substrate.

T-bar anchor 5908 may anchor tether 5904 to bone segment $P_1$. T-bar anchor 5908 may have some or all of the features of anchor 5200 (shown in FIG. 52). Screw-type anchor 5910 may anchor tether 5906 to bone segment $P_2$.

The tethers may be delivered through flared support tube 5912. Flared support tube 5912 may include one-way cleat 5914. The tethers may be drawn in proximal direction Pd to apply tension to the bone segments. One-way cleat 5914 may prevent release of the tension.

Figure 60:
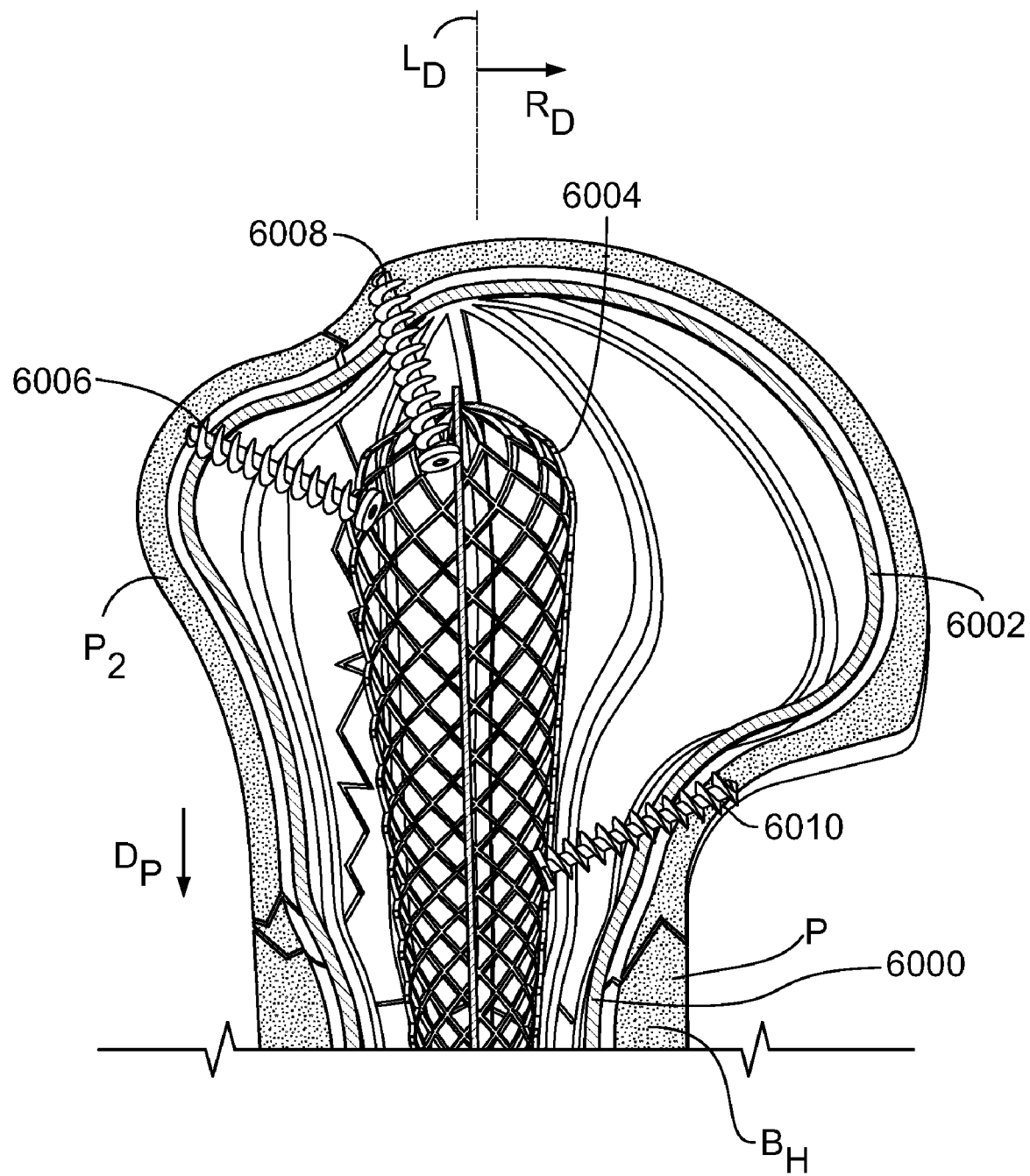
FIG. 60 is a side view of apparatus in accordance with the principles of the invention inside a body portion.

FIG. 60 shows illustrative bone fracture repair device 6000 in accordance with the principles of the invention in humerus $B_H$. Device 6000 includes structural cage 6002. Structural cage 6002 may provide outward radial and longitudinal support for bone segments P, $P_1$ and $P_2$. Structural cage 6002 and anchoring substrate 6004. Anchors 6006, 6008 and 6010 may be delivered by steerable catheter through cage base 6012 and into the interior of anchoring substrate 6004. The anchors may then be inserted in bone segments $P_1$ and $P_2$. The steerable catheter may then be withdrawn. Anchoring substrate 6004 may then be drawn in proximal direction $D_P$ using approaches shown and described herein or other suitable methods. Drawing anchoring substrate 6004 in direction $D_P$ may compress bone segments $P_1$ and $P_2$ against bone segment P.

Figure 61:
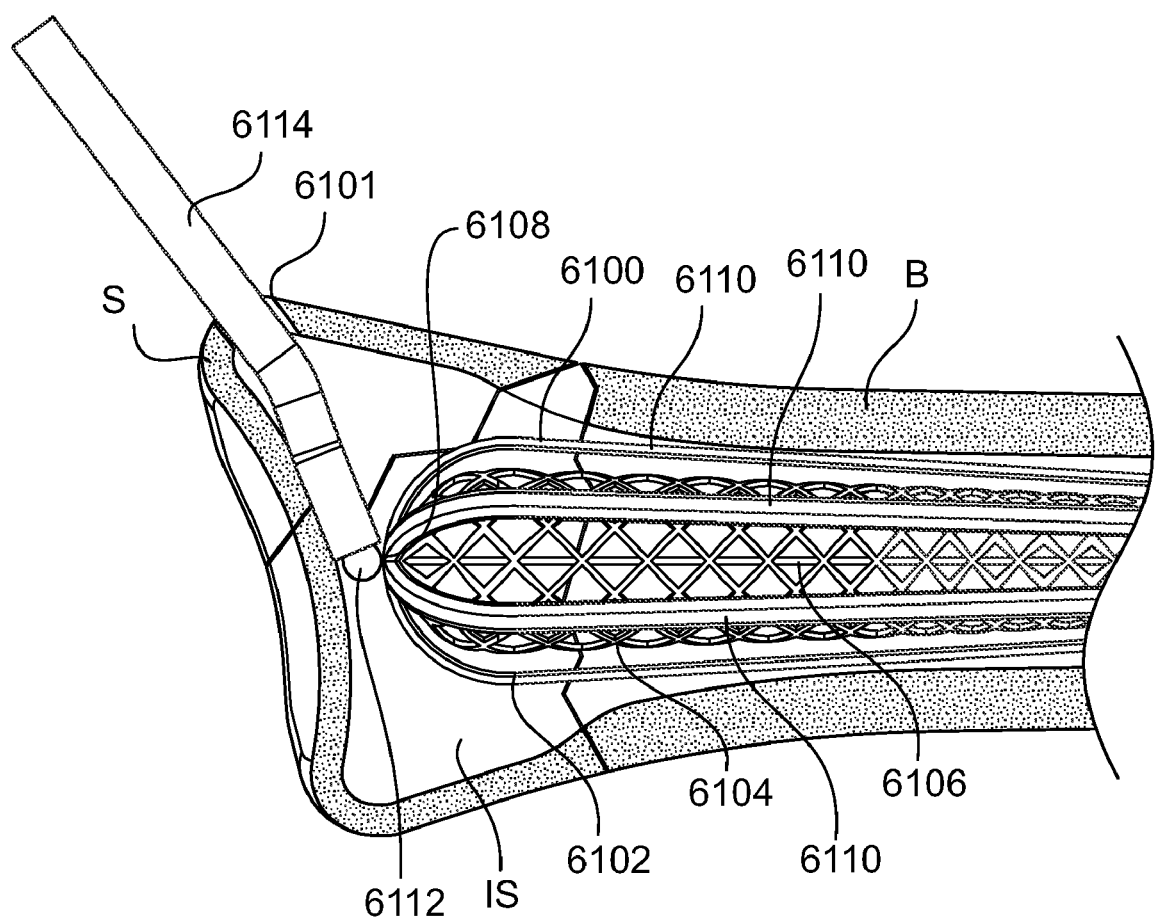
FIG. 61 is a side view of apparatus in accordance with the principles of the invention inside a body portion.

FIG. 61 shows illustrative bone fracture repair device 6100 in accordance with the principles of the invention in bone B. Device 6100 may be delivered to intramedullary space IS of bone B through access hole 6101 in radial styloid S.

Device 6100 may include structural cage 6102, anchoring substrate 6104 and central axis member 6106. Structural cage 6102 may include hub 6108, where support members 6110 rigidly join. Hub 6108 may support device retention member 6112.

Delivery sheath 6114 may provide access to intramedullary space through styloid S. Delivery instruments (not shown) may extend through delivery sheath 6114 and engage device retention member 6112 for positioning and deployment of device 6100.

Figure 62:
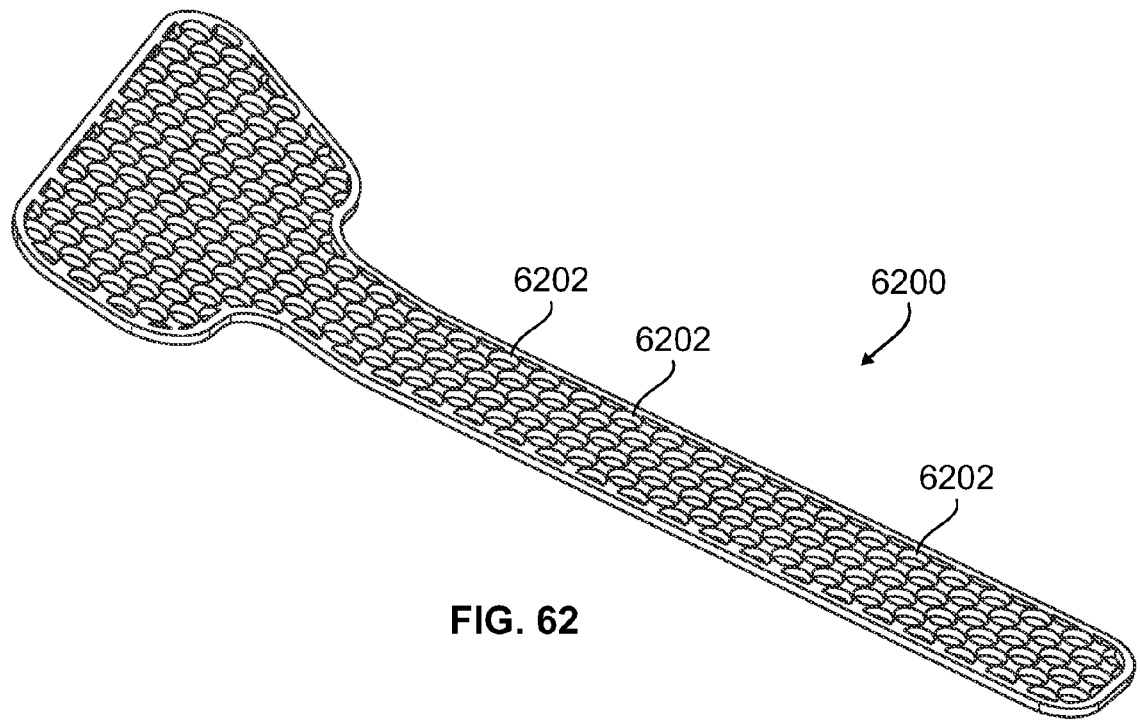
FIG. 62 is a perspective view of apparatus in accordance with the principles of the invention.

FIG. 62 shows illustrative plate 6200 that may be used in connection with a bone fracture repair device in accordance with the principles of the invention. Plate 6200 includes a plurality of holes 6202 for passage of anchors.

Plate 6200 may support bone segments and a device such as 6300 (shown in FIG. 63) that is inside a bone. Plate 6200 may be used during an open surgical procedure on the outer surface of the bone. Plate 6200 may be stiff or flexible. The shape of late 6200 may be selected for the capture of some or all of the bone segments of the bone.

Figure 63:
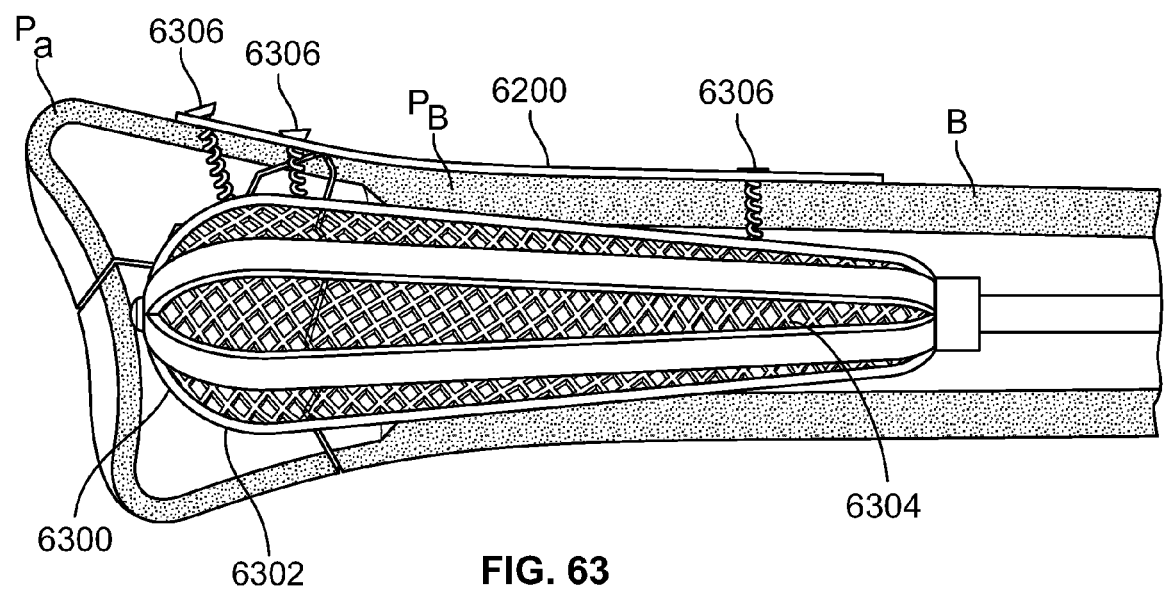
FIG. 63 is a side view of apparatus in accordance with the principles of the invention inside a body portion.

FIG. 63 shows illustrative bone fracture repair device 6300 in accordance with the principles of the invention. Device 6300 may be used in connection with a plate such as 6200 (shown in FIG. 62). Device 6300 may include structural cage 6302 and anchoring substrate 6304. Anchors such as spiral anchors 6306 may be passed through holes 6202 and bone segments $P_B$ and $P_a$. Anchors 6306 may have some or all of the features of anchors 5100 (shown in FIG. 51). Anchors 6306 may anchor in, and lock to, anchoring substrate 6304.

Figure 64:
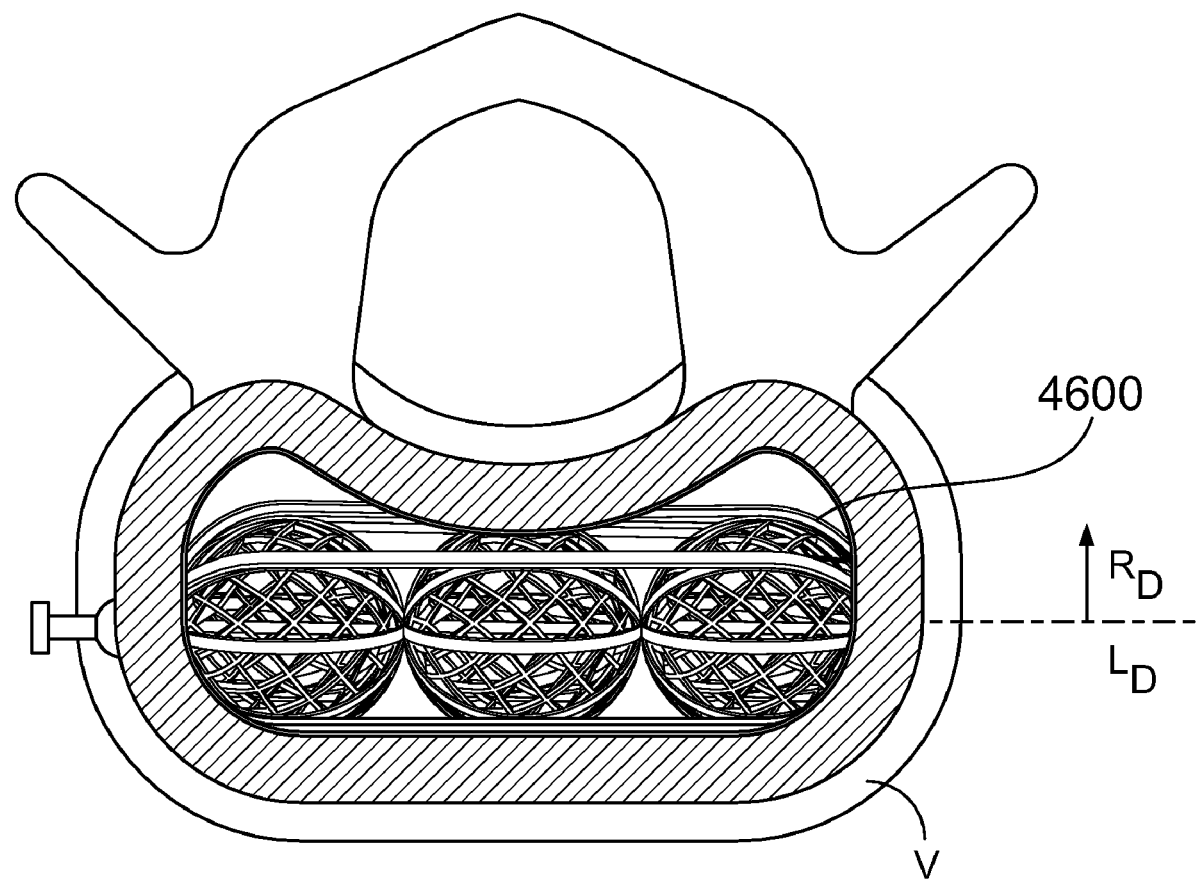
FIG. 64 is a side view of apparatus in accordance with the principles of the invention inside a body portion.

FIG. 64 shows device 4600 (shown in FIG. 46) deployed inside vertebra V. Device 4600 provides outward radial support. Device 4600 may be used in vertebra V without anchors.

Figure 65:
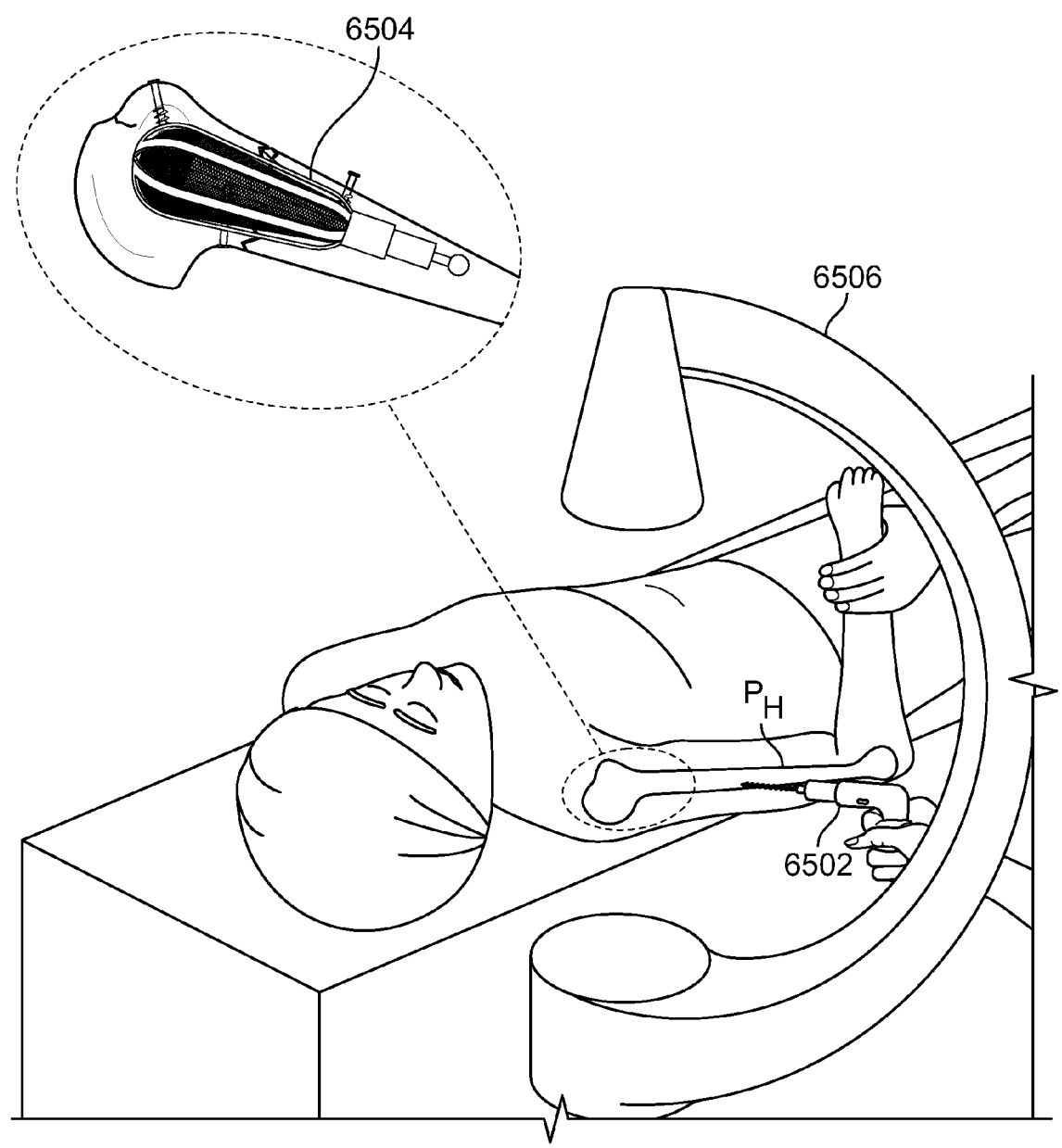
FIG. 65 is a perspective view showing the use of apparatus in accordance with the principles of the invention.

FIG. 65 shows an illustrative scenario for providing access to proximal humerus PH. Introducing instrument 6502 may provide an access hole in proximal humerus PH. Device 6504 may be introduced, positioned, deployed and anchored near the end of proximal humerus PH. Imaging device 6506 may be provided to provide visual information about the location of anatomical features of proximal humerus PH and device 6504.

Figure 66:
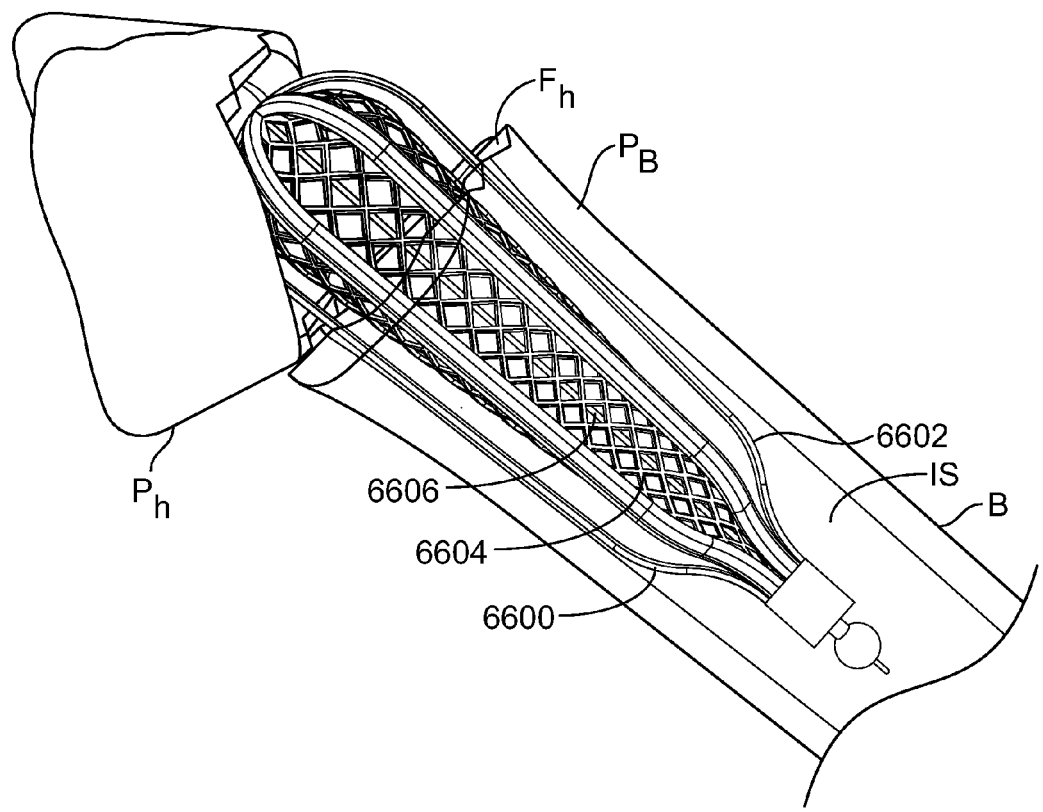
FIG. 66 is a perspective view of apparatus in accordance with the principles of the invention.

FIG. 66 shows an illustrative scenario for deploying illustrative bone fracture repair device 6600 in accordance with the principles of the invention in open fracture $F_h$ of bone B. Device 6600 may include structural cage 6602, anchoring substrate 6604 and central axis member 6606. Device 6600 may be inserted into intramedullary space of bone B via fracture $F_h$. Device 6600 may be inserted in a contracted state. Device 6600 may be inserted in an expanded state.

Figure 67:
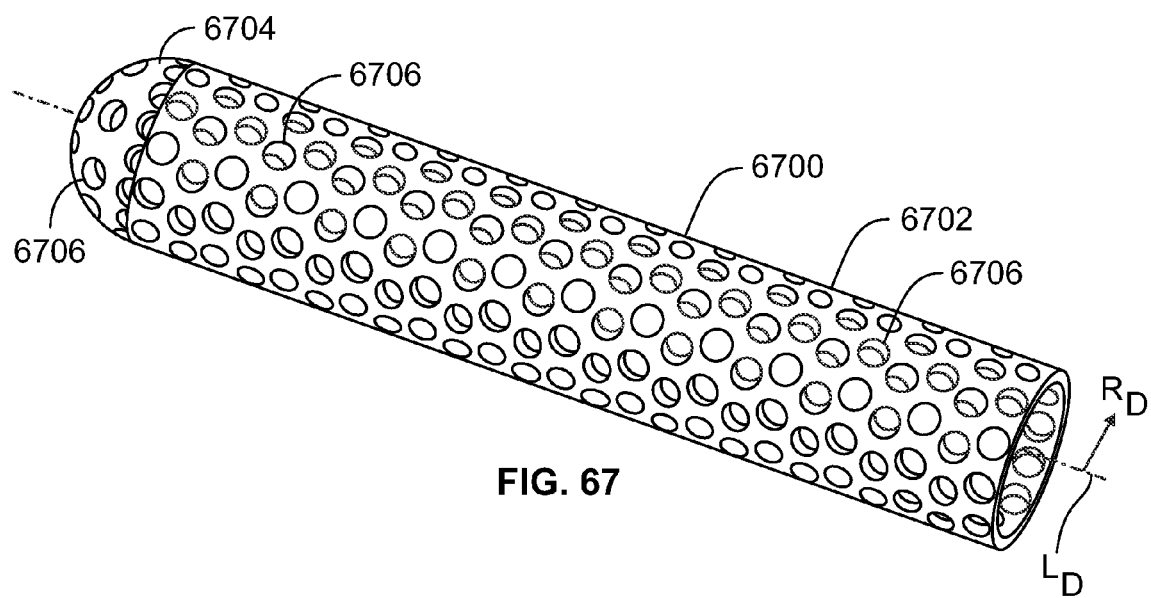
FIG. 67 is a perspective view of apparatus in accordance with the principles of the invention.

FIG. 67 shows illustrative anchoring substrate 6700 that may be used with a fracture repair device in accordance with the principles of the invention. Anchoring substrate 6700 may include elongated portion 6702. Elongated portion 6702 may be terminated with end cap 6704. One or both of elongated portion 6702 and end cap 6704 may include holes 6706. Holes 6706 may be engaged with anchors to hold bone segments in place.

Anchoring substrate 6700 may be used for repairing bones having open fractures such as fracture $F_h$ of bone B as shown in FIG. 66. Anchoring substrate 6700 may be expandable. Anchoring substrate may be non-expandable.

Apparatus and methods described herein are illustrative. Apparatus and methods of the invention may involve some or all of the features of the illustrative apparatus and/or some or all of the steps of the illustrative methods. The steps of the methods may be performed in an order other than the order shown and described herein. Some embodiments of the invention may omit steps shown and described in connection with the illustrative methods. Some embodiments of the invention may include steps that are not shown and described in connection with the illustrative methods.

Figure 68:
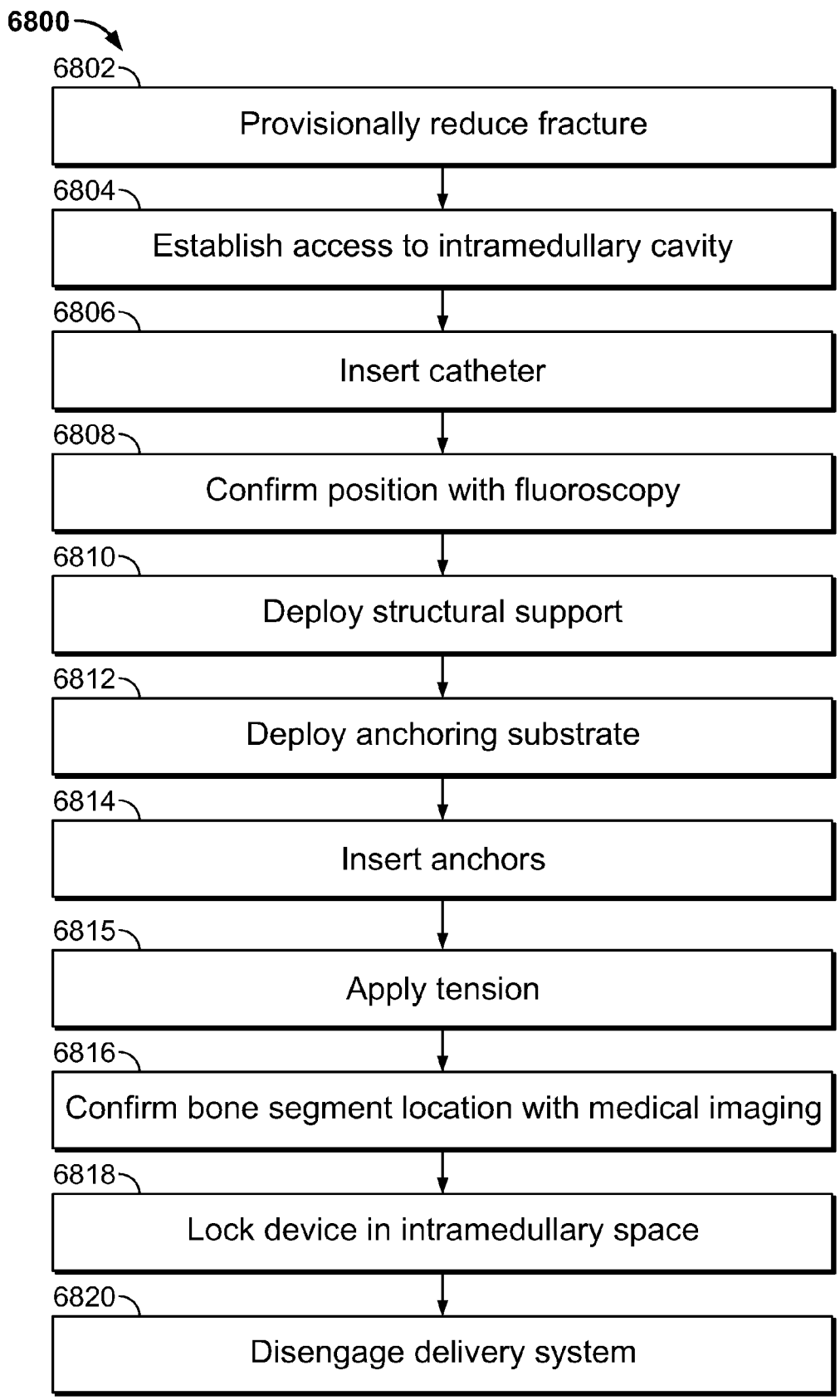
FIG. 68 is an illustrative flow diagram that shows a method in accordance with the principles of the invention.

Processes in accordance with the principles of the invention may include one or more features of the processes illustrated in FIG. 68. Some steps of the processes may be performed in an inpatient setting. Some steps of the processes may be performed in an outpatient setting.

FIG. 68 shows illustrative steps of process 6800 for repairing a fracture. Process 6800 may begin at step 6802. At step 6802, a caregiver may provisionally reduce the fracture. At step 6804, the caregiver may establish access to the intramedullary cavity in the fractured bone. At step 6806, the caregiver may insert a catheter into the fractured bone. At step 6808, the caregiver may confirm positioning of the catheter using fluoroscopy (or any other suitable imaging approach). At step 6810, the caregiver may deploy a structural support such as structural cage 105 (shown in FIG. 1). At step 6812, the caregiver may deploy an anchoring substrate such as anchoring substrate 112 (shown in FIG. 1). At step 6814, the caregiver may insert anchors into the bone segments and anchoring substrate. At step 6815, the caregiver may apply tension. The tension may be applied to one or more of an anchor, an anchoring substrate, a structural support or any of the apparatus shown and described herein using any of the approaches shown and described herein. At step 6816, the caregiver may confirm bone segment location using medical imaging. At step 6818, the caregiver may lock the insert devices in the intramedullary cavity. At step 6820, the inserted devices may be disengaged from the delivery system used to deliver the devices.

There are different combinations of implant sequences. Table 4 shows different illustrative sequences of treatment steps. Other treatment steps and different sequences may also be practiced in accordance with the principles of the invention.

TABLE 4

Illustrative fracture repair sequences.

| Illustrative sequence A | Illustrative sequence B | Illustrative sequence C |
| --- | --- | --- |
| Reduce fracture | Anchor | Manipulate segments |
| Introduce device | Manipulate segments | Engage segments |
| Anchor segment to device | Engage segments | Anchor |
| Tension assembly to finalize reduction | Tension segments | Provide tension to segments |
| Anchor assembly | Anchor or secure segments | Lock assembly |
| Disengage from the assembly | Disengage | Further appropriate steps |
| Further appropriate steps | Further appropriate steps | |

There are numerous other steps that may be included. Different embodiments of the apparatus shown and described herein may be used in conjunction with different steps of process 6800, whether or not shown in FIG. 68 or Table 4. For example, bone cement may be applied, cancellous autograph may be inserted, topical or internal antibiotics may be administered and any other suitable therapies may be used.

Thus, apparatus and methods for fracture repair have been provided. Persons skilled in the art will appreciate that the present invention can be practiced by other than the described embodiments, which are presented for purposes of illustration rather than of limitation. The present invention is limited only by the claims that follow.

What is claimed is:

1. An apparatus for treating a fracture of a bone, the fracture including segments, the bone having an inner cavity, the apparatus comprising:

a structural support for positioning a first of the bone segments relative to a second of the bone segments, the structural support being configured to be deployed in the inner cavity;

an anchoring substrate configured to maintain a position of the first bone segment relative to the second bone segment, the anchoring substrate being configured to be deployed in the inner cavity;

a proximal anchor that is configured to secure a proximal portion of the anchoring substrate to the bone; and, when the proximal anchor has a center axis, a detent configured to fix the distal end of the proximal anchor, with respect to the center axis, to the structural support;

wherein:
the proximal anchor is substantially cylindrical and comprises blades that extend radially outward;
the proximal anchor includes a proximal end and a distal end;
the blades move radially outward when the proximal and distal ends are moved toward each other; and
the proximal end of the proximal anchor is configured to be pushed distally to move the blades radially outward.

2. An apparatus for treating a fracture of a bone, the fracture including segments, the bone having an inner cavity, the apparatus comprising:
a structural support for positioning a first of the bone segments relative to a second of the bone segments, the structural support being configured to be deployed in the inner cavity;
an anchoring substrate configured to maintain a position of the first bone segment relative to the second bone segment, the anchoring substrate being configured to be deployed in the inner cavity;
a proximal anchor that is configured to secure a proximal portion of the anchoring substrate to the bone; and,
when the proximal anchor has a center axis, a detent configured to rotatably fix a distal end of the proximal anchor, with respect to the center axis, to the structural support;
wherein:
the proximal anchor is substantially cylindrical and comprises blades that extend radially outward;
the blades comprise helical portions of the proximal anchor; and
a proximal end of the proximal anchor is configured to be pushed distally and rotated about the center axis to move the blades radially outward while the proximal anchor rotates about the center axis.

3. Apparatus for repairing a fractured bone, the apparatus comprising:
a bone segment support configured to be deployed inside the bone;
an anchoring substrate configured to be deployed inside the bone; and
a relative displacement actuator configured to displace a portion of the anchoring substrate relative to a portion of the bone segment support;
wherein:
the relative displacement actuator has a central axis and comprises:
a first displacing member fixed, with respect to the central axis, to the bone segment support; and
a second displacing member fixed, with respect to the central axis, to the anchoring substrate;
the first displacing member is engaged with the second displacing member such that relative motion, along the central axis, of the first and second displacing members changes the distance, along the central axis, between a portion of the bone segment support and a portion of the anchoring substrate; and
the first displacing member is threadedly engaged with the second displacing member.

4. The apparatus of claim 3 wherein the bone segment support is one of several bone segment supports that form a support cage.

5. The apparatus of claim 3 wherein:
the bone segment support is elongated and comprises along its length a first bone segment support portion and a second bone segment support portion;
the first bone segment support portion has a first bending resistance;
the second bone segment support portion has a second bending resistance; and
the first bending resistance is greater than the second bending resistance.

6. The apparatus of claim 3 wherein rotation of the first displacing member relative to the second displacing member causes displacement, along the central axis, between the portion of the bone segment support and the portion of the anchoring substrate.

* * * * *